(12) United States Patent
Bennani et al.

(10) Patent No.: US 12,203,946 B2
(45) Date of Patent: *Jan. 21, 2025

(54) PREPARATION OF FETAL NUCLEATED RED BLOOD CELLS (NRBCS) FOR DIAGNOSTIC TESTING

(71) Applicant: KELLBENX INCORPORATED, Great River, NY (US)

(72) Inventors: Hassan Bennani, Dix Hills, NY (US); Leonard H. Kellner, Massapequa, NY (US)

(73) Assignee: KELLBENX INCORPORATED, Great River, NY (US)

( * ) Notice: Subject to any disclaimer, the term of this patent is extended or adjusted under 35 U.S.C. 154(b) by 85 days.

This patent is subject to a terminal disclaimer.

(21) Appl. No.: 17/902,095

(22) Filed: Sep. 2, 2022

(65) Prior Publication Data

US 2023/0242881 A1    Aug. 3, 2023

Related U.S. Application Data

(63) Continuation of application No. 17/585,820, filed on Jan. 27, 2022, now abandoned, which is a
(Continued)

(51) Int. Cl.
*G01N 33/80* (2006.01)
*C07K 16/28* (2006.01)
(Continued)

(52) U.S. Cl.
CPC ......... *G01N 33/80* (2013.01); *C07K 16/2881* (2013.01); *C07K 16/2896* (2013.01); *C12Q 1/6806* (2013.01); *C12Q 1/6883* (2013.01);

*G01N 33/54326* (2013.01); *G01N 33/56966* (2013.01); *G01N 33/582* (2013.01);
(Continued)

(58) Field of Classification Search
CPC ............. G01N 33/53; G01N 33/54313; G01N 33/54326; G01N 33/555; G01N 33/56966; G01N 33/6893; G01N 33/80; G01N 2800/385; G01N 2800/387; G01N 33/48; G01N 33/582; G01N 33/6878; C07K 16/2881; C07K 16/2896

See application file for complete search history.

(56) References Cited

U.S. PATENT DOCUMENTS

| 4,111,199 A | 9/1978 | Djerassi |
| 4,744,907 A | 5/1988 | Klimchak |

(Continued)

FOREIGN PATENT DOCUMENTS

| AU | 2015249071 A1 | 11/2015 |
| WO | WO-94/28425 A1 | 12/1994 |

(Continued)

OTHER PUBLICATIONS

U.S. Appl. No. 17/860,226, Bennani, Hassan.
(Continued)

*Primary Examiner* — Gailene Gabel
(74) *Attorney, Agent, or Firm* — Clark & Elbing LLP

(57) ABSTRACT

The disclosure relates to methods of preparation of fetal nucleated red blood cells (NRBCs) from biological samples for diagnostic testing.

16 Claims, 40 Drawing Sheets

Figure 1:
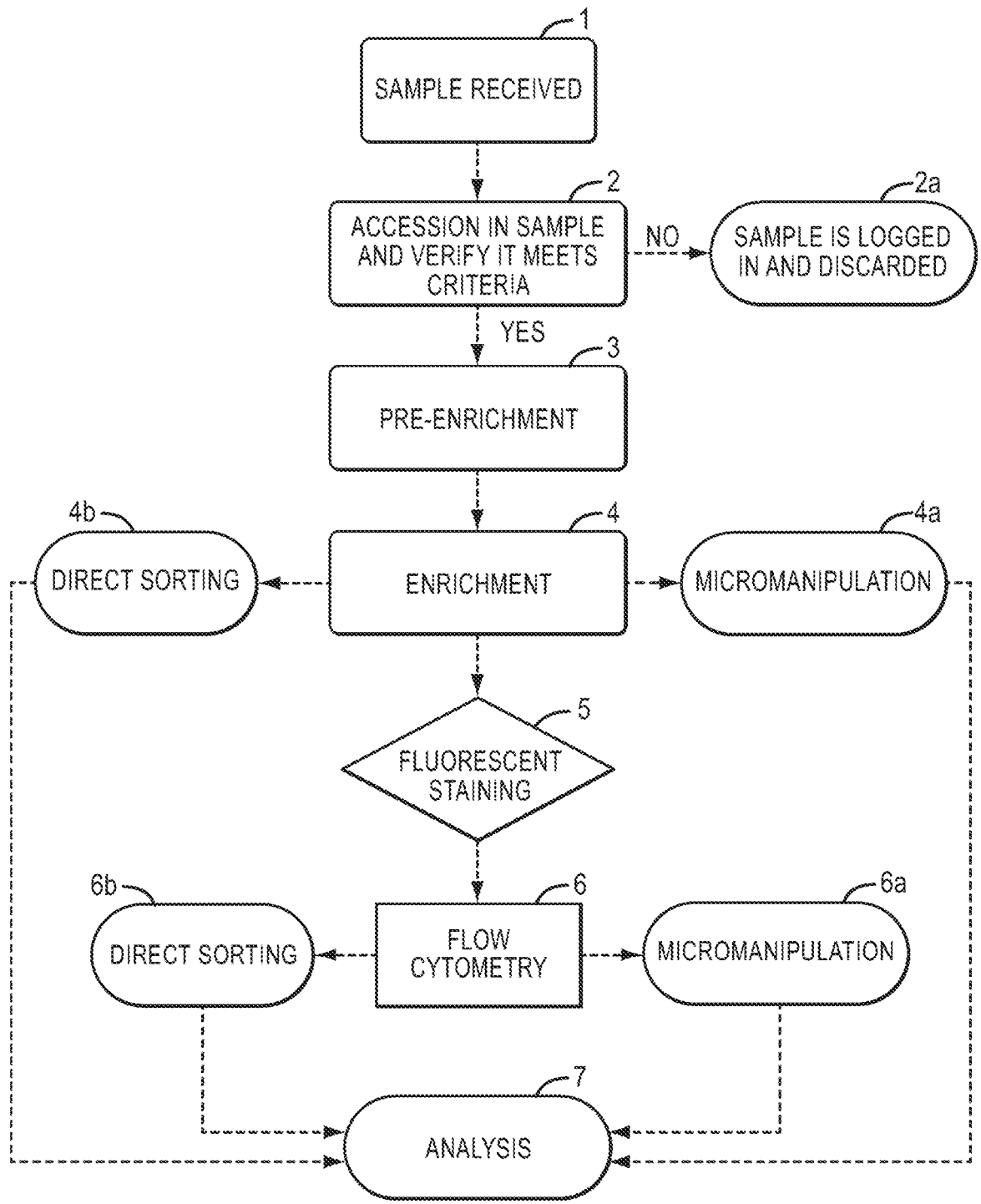

Related U.S. Application Data continuation of application No. 17/347,832, filed on Jun. 15, 2021, now abandoned, which is a continuation of application No. 17/085,070, filed on Oct. 30, 2020, now abandoned, which is a continuation of application No. 16/824,007, filed on Mar. 19, 2020, now abandoned, which is a continuation of application No. 16/237,179, filed on Dec. 31, 2018, now abandoned, which is a continuation of application No. 14/934,382, filed on Nov. 6, 2015, now abandoned, which is a continuation-in-part of application No. 14/710,460, filed on May 12, 2015, now abandoned.

(60) Provisional application No. 61/993,659, filed on May 15, 2014.

(51) Int. Cl.
*C12Q 1/6806* (2018.01)
*C12Q 1/6883* (2018.01)
*G01N 33/543* (2006.01)
*G01N 33/569* (2006.01)
*G01N 33/58* (2006.01)
*G01N 33/68* (2006.01)
*C12N 5/078* (2010.01)

(52) U.S. Cl.
CPC ..... *G01N 33/6878* (2013.01); *G01N 33/6893* (2013.01); *C12N 5/0641* (2013.01); *C12Q 2531/113* (2013.01); *C12Q 2565/501* (2013.01); *C12Q 2600/156* (2013.01); *C12Q 2600/158* (2013.01); *G01N 2800/385* (2013.01); *G01N 2800/387* (2013.01)

(56) References Cited

U.S. PATENT DOCUMENTS

| | | | |
|---|---|---|---|
| 4,765,899 A | 8/1988 | Wells et al. | |
| 5,147,290 A | 9/1992 | Jonsson | |
| 5,486,359 A | 1/1996 | Caplan et al. | |
| 5,545,616 A | 8/1996 | Woodruff | |
| 5,750,339 A * | 5/1998 | Smith | G01N 33/56972 435/7.21 |
| 6,309,606 B1 | 10/2001 | Sitar | |
| 7,232,661 B2 | 6/2007 | Yoon | |
| 7,615,374 B2 | 11/2009 | Vodyanyk et al. | |
| 7,785,865 B2 | 8/2010 | Qinwei | |
| 7,790,463 B2 | 9/2010 | Mor et al. | |
| 7,858,757 B2 * | 12/2010 | Hollmann | G01N 33/56966 435/7.25 |
| 7,892,774 B2 | 2/2011 | Rutanen | |
| 8,137,912 B2 | 3/2012 | Kapur et al. | |
| 8,426,122 B2 | 4/2013 | Parikh et al. | |
| 8,536,312 B2 | 9/2013 | Hollmann et al. | |
| 9,194,871 B2 | 11/2015 | Hollmann et al. | |
| 9,447,467 B2 * | 9/2016 | Allman | G01N 33/483 |
| 9,453,841 B2 | 9/2016 | Hollmann et al. | |
| 10,545,156 B2 | 1/2020 | Equils et al. | |
| 2001/0034037 A1 | 10/2001 | Patel et al. | |
| 2003/0134416 A1 | 7/2003 | Yamanishi et al. | |
| 2003/0170613 A1 | 9/2003 | Straus | |
| 2003/0180762 A1 | 9/2003 | Tuma et al. | |
| 2004/0014063 A1 | 1/2004 | Batteux et al. | |
| 2004/0142463 A1 | 7/2004 | Walker et al. | |
| 2005/0214758 A1 | 9/2005 | Yura et al. | |
| 2006/0051775 A1 | 3/2006 | Bianchi | |
| 2006/0063162 A1 | 3/2006 | Deng | |
| 2006/0105353 A1 * | 5/2006 | Jalal | G01N 33/56966 435/6.12 |
| 2006/0166277 A1 | 7/2006 | Karumanchi et al. | |
| 2007/0161125 A1 | 7/2007 | Rosenfeld et al. | |
| 2007/0178605 A1 | 8/2007 | Mor et al. | |
| 2007/0238655 A1 | 10/2007 | Bucki et al. | |
| 2007/0264675 A1 | 11/2007 | Toner et al. | |
| 2007/0275418 A1 | 11/2007 | Hollmann et al. | |
| 2008/0057505 A1 | 3/2008 | Lin et al. | |
| 2009/0226397 A1 | 9/2009 | Carter | |
| 2010/0137263 A1 | 6/2010 | Smith | |
| 2010/0159506 A1 | 6/2010 | Parikh et al. | |
| 2010/0178650 A1 | 7/2010 | Karsten et al. | |
| 2010/0178656 A1 | 7/2010 | Buffiere et al. | |
| 2010/0233696 A1 | 9/2010 | Joseph et al. | |
| 2010/0255479 A1 | 10/2010 | Mikolajczyk et al. | |
| 2010/0285581 A1 | 11/2010 | Hauch et al. | |
| 2010/0304978 A1 | 12/2010 | Deng et al. | |
| 2011/0028341 A1 | 2/2011 | Wang et al. | |
| 2011/0110931 A1 | 5/2011 | Matsui | |
| 2011/0117575 A1 | 5/2011 | Buehring et al. | |
| 2012/0021508 A1 | 1/2012 | Parikh et al. | |
| 2012/0107413 A1 | 5/2012 | Lim et al. | |
| 2012/0238469 A1 | 9/2012 | Equils et al. | |
| 2013/0122492 A1 | 5/2013 | Khosravi et al. | |
| 2013/0130265 A1 | 5/2013 | Parikh et al. | |
| 2013/0130266 A1 | 5/2013 | Stone | |
| 2013/0137137 A1 | 5/2013 | Brody et al. | |
| 2014/0051598 A1 | 2/2014 | Equils et al. | |
| 2014/0154704 A1 | 6/2014 | Hollmann et al. | |
| 2014/0193375 A1 | 7/2014 | Zeigler et al. | |
| 2014/0315748 A1 | 10/2014 | Khosravi et al. | |
| 2015/0133332 A1 | 5/2015 | Khosravi et al. | |
| 2015/0330979 A1 | 11/2015 | Bennani et al. | |
| 2016/0039932 A1 | 2/2016 | Hollmann et al. | |
| 2016/0069891 A1 | 3/2016 | Equils et al. | |
| 2016/0130553 A1 | 5/2016 | Bennani et al. | |
| 2017/0322960 A1 | 11/2017 | Glebe et al. | |
| 2018/0038871 A1 | 2/2018 | Equils et al. | |
| 2018/0120295 A1 | 5/2018 | Sitar | |
| 2018/0292405 A1 | 10/2018 | Bennani et al. | |
| 2019/0153392 A1 | 5/2019 | Sitar | |
| 2019/0376033 A1 | 12/2019 | Bennani et al. | |
| 2020/0325476 A1 | 10/2020 | Derosa et al. | |
| 2021/0072227 A1 | 3/2021 | Sitar | |
| 2022/0349906 A1 | 11/2022 | Bennani | |
| 2022/0389384 A1 | 12/2022 | Sitar | |
| 2023/0242881 A1 | 8/2023 | Bennani et al. | |
| 2023/0258634 A1 * | 8/2023 | Bennani | C12N 5/0641 435/7.25 |
| 2023/0324383 A1 | 10/2023 | Hollmann et al. | |
| 2024/0085439 A1 * | 3/2024 | Bennani | G01N 1/34 |

FOREIGN PATENT DOCUMENTS

| | | |
|---|---|---|
| WO | WO-96/07097 A1 | 3/1996 |
| WO | WO-1999/023471 A1 | 5/1999 |
| WO | WO-2000/060351 A1 | 10/2000 |
| WO | WO-2002/055985 A2 | 7/2002 |
| WO | WO-02/101387 A2 | 12/2002 |
| WO | WO-2003/031938 A2 | 4/2003 |
| WO | WO-2004/076653 A1 | 9/2004 |
| WO | WO-2005/100401 A2 | 10/2005 |
| WO | WO-2007/065438 A2 | 6/2007 |
| WO | WO-07/112514 A1 | 10/2007 |
| WO | WO-08/056114 A1 | 5/2008 |
| WO | WO-2009/009769 A2 | 1/2009 |
| WO | WO-2009/035447 A1 | 3/2009 |
| WO | WO-09/134452 A2 | 11/2009 |
| WO | WO-2010/012002 A1 | 1/2010 |
| WO | WO-2010/085815 A1 | 7/2010 |
| WO | WO-2010/121294 A1 | 10/2010 |
| WO | WO-2011/014741 A1 | 2/2011 |
| WO | WO-2011/071893 A1 | 6/2011 |
| WO | WO-2011/089603 A1 | 7/2011 |
| WO | WO-2012/125641 A1 | 9/2012 |
| WO | WO-2013/074520 A2 | 5/2013 |
| WO | WO-2015/175562 A1 | 11/2015 |
| WO | WO-2016/118484 A1 | 7/2016 |
| WO | WO-2016/178931 A1 | 11/2016 |
| WO | WO-2017/176969 A1 | 10/2017 |
| WO | WO-2020/223596 A1 | 11/2020 |

(56) References Cited

OTHER PUBLICATIONS

Aguilar-Valles et al., "Attenuated fever in rats during late pregnancy is linked to suppressed interleukin-6 production after localized inflammation with turpentine," Journal of Physiology. vol. 583 (Pt 1), pp. 391-403 (Jun. 2007).

Alvarerz et al., "Development, characterization, and use of monoclonal antibodies made to antigens expressed on the surface of fetal nucleated red blood cells," Clin. Chem., 45:1614-1620, 1999.

Anker et al., "Isolation of Mesenchymal Stem Cells of Fetal or Maternal Origin from Human Placenta," Stem Cells. 22:1338-1345 (2004) (9 pages).

Barshtein et al., "Kinetics of Linear Rouleaux Formation Studied by Visual Monitoring of Red Cell Dynamic Organization," Biophysical Journal. 78(5):2470-2474 (2000).

Bates et al., "Aberrant cytokine production by peripheral blood mononuclear cells in recurrent pregnancy loss?," Human Reproduction. vol. 17, No. 9, pp. 2439-2444 (2002).

Bianchi et al., "Erythroid-Specific Antibodies Enhance Detection of Fetal Nucleated Erythrocytes in Maternal Blood," Prenatal Diagnosis, 13:293-300, 1993.

Bianchi et al., "Fetal Cells in the maternal circulation: feasibility for prenatal diagnosis," Br. J. Haematology, 105:574-583, 1999.

Bianchi et al., "Fetal gender and aneuploidy detection using fetal cells in maternal blood: analysis of NIFTY I data," National Institute of Child Health and Development Fetal Cell Isolation Study. Prenat Diagn. 22(7):609-15 (Jul. 2002).

Bianchi et al., "Isolation of fetal DNA from nucleated erythrocytes in maternal blood," Proc Natl Acad Sci U S A. 87(9):3279-83 (May 1990).

Blanchard et al., English language translation "Caracterisation d'anticorps monoclonaux murins diriges contre les erythrocytes foetaux," Revue francaise de transfusion et d'hemobiologie 35:239-254, (32 pages) (1992).

Busch et al., "Enrichment of fetal cells from maternal blood by high gradient magnetic cell sorting (double MACS) for PCT-based genetic analysis," Prenat Diagn. 14(12):1129-40 (Dec. 1994).

Calabrese et al., "Detection of chromosomal aneuploidies in fetal cells isolated from maternal blood using single-chromosome dual-probe FISH analysis," Clin Genet., doi: 10.1111/j.1399-0004.2011.01775.x, pp. 1-9 (2011).

Campagnoli et al. Identification of mesenchymal stem/progenitor cells in human first-trimester fetal blood, liver, and bone marrow. Blood, 98(8):2396-2402 (2001).

Chan et al., "First trimester embryo-fetoscopic and ultrasound-guided fetal blood sampling for ex vivo viral transduction of cultured human fetal mesenchymal stem cells," Human Reproduction. 23(11):2427-2437, doi:10.1093/humrep/den302 (2008).

Chan et al., "Human Fetal Mesenchymal Stem Cells as Vehicles for Gene Delivery," Stem Cells. 23:93-102 (2005) (11 pages).

Chan et al., "Prenatal transplantation of mesenchymal stem cells to treat osteogenesis imperfecta," Frontiers in Pharmacology—Integrative and Regenerative Pharmacology. 5(223): 1-6, doi: 10.3389/fphar.2014.00223 (2014).

Chen et al., "Immunomodulatory properties of human adult and fetal multipotent mesenchymal stem cells," Journal of Biomedical Science. 18:49, pp. 1-11, http://www.jbiomedsci.com/content/18/1_/49_<http://www.jbiomedsci.com/content/18/1%20/49> (2011).

Choolani et al., "Fetal therapy: 2020 and beyond," Prenat. Diagn. 30:699-701, DOI: 10.1002/pd.2527 (2010) (3 pages).

Christensen et al., "Studies on the isolation and identification of fetal nucleated red blood cells in the circulation of pregnant women before and after chorion villus sampling," Fetal Diagnosis and Therapy, Karger, Basel, CH, vol. 18, No. 5 (2003) (9 pages).

Curry et al., "First-trimester maternal plasma cytokine levels, prepregnancy body mass index, and spontaneous preterm delivery," Acta Obstet. Gynecol. Scand. vol. 88, No. 2, pp. 332-342, ePub 88: 332-42 (Jan. 2009).

Curry et al., "Mid-pregnancy maternal plasma levels of interleukin 2, 6, and 12, tumor necrosis factor-alpha, inteferon-gamma, and granulocyte-macrophage colony-stimulating factor and spontaneous preterm delivery," Acta Obstet. Gynecol. Scand., vol. 86, No. 9, pp. 1103-1110 (2007).

Demaria et al., "Improved fetal nucleated erythrocyte sorting purity using intracellular antifetal hemoglobin and Hoechst 33342," Cytometry. 25(1):37-45 (Sep. 1996).

Diamandis et al., "Circulating Cancer Cells and Their Clinical Applications," Clinical Chemistry. 57: 11, 1478-1484 (2011).

Fofie et al., "Pregnancy Influences the Plasma Cytokine Response to Response to Intraperitoneal Administration of Bacterial Endotoxin in Rats," Experimental Physiology. vol. 90, No. 1, pp. 95-101, Jan. 2005 (ePub Oct. 2004) (7 pages).

Hashii et al., "Peripheral blood mononuclear cells stimulate progesterone production by luteal cells derived from pregnant and non-pregnant women: possible involvement of interleukin-4 and interleukin-10 in corpus luteum function and differentiation," Human Reproduction. vol. 13, No. 10, pp. 2738-2744 (1998).

Hass et al., "Different populations and sources of human mesenchymal stem cells (MSC): A comparison of adult and neonatal tissue-derived MSC," Cell Communication and Signaling. 9:12, pp. 1-14, <http://www.biosignaling.com/contenU9/1/12> (2011).

Hennerbichler et al., "Fetal nucleated red blood cells in peripheral blood of pregnant women: detection and determination of location on a slide using laser-scanning cytometry," Pren at Diagn. 23:710-715 (2003).

Hirvonen et al., "Production of a Recombinant Antibody Specific for i Blood Group Antigen, a Mesenchymal Stem Cell Marker," BioResearch Open Access. 2(5):336-345, DOI:10.1089/biores.2013.0026 (2013).

Huang et al., "Industrial production of recombinant therapeutics in *Escherichia coli* and its recent advancements," J Ind Microbial Biotechnol. 39(3):383-99 (Mar. 2012).

Huang, Zhouwei et al., "Novel approaches to manipulating foetal cells in the maternal circulation for non-invasive prenatal diagnosis of the unborn child," J. Cell BioChem. 112: pp. 1475-1485 (2011), DOI: 10.1002/jcb.23084 (Apr. 18, 2011) (Abstract Only).

Huie et al., "Antibodies to human fetal erythroid cells from a nonimmune phage antibody library," Proc. Natl. Acad. Sci. USA, 98:2682-2687, 2001.

Kalinka et al., "Interleukin-1 beta and interleukin-1 receptor antagonist gene polymorphisms and the risk of spontaneous preterm delivery in the population of Polish women," Arch Perinatal. Med. vol. 14, No. 4, pp. 33-36 (2008).

Kavanagh, D.M. et al., "Current and emerging techniques of fetal cell separation from maternal blood," Journal of Chromatography. B, 878 pp. 1905-1911 (2010).

Kruse et al., "Prospective, serial investigations of in-vitro lymphocyte cytokine production, CD62L expression and proliferative response to microbial antigens in women with recurrent miscarriage," Human Reproduction. 18(11):2465-2472 (2003).

Kwok et al., "Maternal plasma or human serum albumin in wash buffer enhances enrichment and ex vivo expansion of human umbilical cord blood CD34 + cells," British Journal of Haematology. 137(5):468-474, XP055431138 (2003).

Lange et al., "Accelerated and Safe Expansion of Human Mesenchymal Stromal Cells in Animal Serum-Free Medium for Transplantation and Regenerative Medicine," J. Cell. Physiol. 213: pp. 18-26 (2007).

Lapierre et al., "Cord blood vol. reduction using an automated system (Sepax) vs. a semi-automated system (Optipress II) and a manual method (hydroxyethyl starch sedimentation) for routine cord blood banking: a comparative study," Cytotherapy. vol. 9(2): 165-9, (2007) downloaded from <http://www.ncbi.nlm.nih.gov/pubmed/17453968> on Mar. 20, 2015 (5 pages).

Le Blanc et al., "Fetal mesenchymal stem-cell engraftment in bone after in utero transplantation in a patient with severe osteogenesis imperfecta," Transplantation. 79(11):1607-14, downloaded from <http://www.ncbi.nlm.nih.gov/pubmed/15940052>, on Sep. 14, 2015 (2005).

Li et al., "Therapeutic potential of in utero mesenchymal stem cell (MSCs) transplantation in rat foetuses with spina bifida aperta," J. Cell. Mol. Med. 16(7):1606-1617, doi:10.1111/j.1582-4934.2011.01470.x (2012).

(56) References Cited

OTHER PUBLICATIONS

Lin et al., "Stem cell therapy: an exercise in patience and prudence," Phil Trans R Soc B. 368:20110334, pp. 1-14, <http://dx.doi.org/10.1098/rstb.2011.0334> (2012).
Lok et al., "Leukocyte Activation and Circulating Leukocyte-Derived Microparticles in Preeclampsia," American Journal of Reproductive Immunology. vol. 61, pp. 346-359 (2009).
Maes et al., "Immune activation in the early puerperium is related to postpartum anxiety and depressive symptoms," Psychoneuroendocrinology. vol. 25, pp. 121-137 (2000).
Makhseed M et al., "Pro-inflammatory Maternal Cytokine Profile in Preterm Delivery," Obstetrics. vol. 58, No. 11 (2003) (pp. 700-719).
Marzi et al., "Characterization of type 1 and type 2 cytokine production profile in physiologic and pathologic human pregnancy," Clinical & Experimental Immunology. 106(1): pp. 127-133 (Oct. 1, 1996).
Matalka et al., "Stress-Induced versus Preovulatory and Pregnancy Hormonal Levels in Modulating Cytokine Production following Whole Blood Stimulation," Neuroimmunomodulation. 12(6):366-74 (2005).
Menon et al., "Differences in the Placental Membrane Cytokine Response: A Possible Explanation for the Racial Disparity in Preterm Birth," Am J Reprod Immunol. 56: pp. 112-118 (2006).
Migliaccio et al., "Human Embryonic Hemopoiesis—Kinetics of Progenitors and Precursors Underlying the Yolk Sac --> Liver Transition," J. Clin. Invest. 78:51-60 (1986).
Muller, I. et al., "Retrieval and Perfect Hashing Using Fingerprinting," J. Gudmundsson and J. Katajainen (Eds.), SEA 2014: Experimental Algorithms, Springer International Publishing, Copenhagen, Denmark, Jun. 29-Jul. 1, 2014, (19 pages).
Munoz et al., "Sedimentation method for preparation of postoperatively salvaged unwashed shed blood in orthopaedic surgery," British Journal of Anaesthesia. 105(4):457-65 (2010).
O'Donoghue et al., "Identification of fetal mesenchymal stem cells in maternal blood: implications for non-invasive prenatal diagnosis," Molecular Human Reproduction. 9(8):497-502, DOI:10.1093/molehr/gag063 (2003).
Pepe et al., "Limitations of the Odds Ratio in Gauging the Performance of a Diagnostic, Prognostic, or Screening Marker," American Journal of Epidemiology. vol. 159(9), pp. 882-890 (2004).
Peters et al., "Efficient Generation of Multipotent Mesenchymal Stem Cells from Umbilical Cord Blood in Strama-Free Liquid Culture," PLoS ONE. 5(12): e15689, pp. 1-14. doi: 10.1371/journal.pone.0015689 (2010).
Purwosunu et al., "Clinical potential for noninvasive prenatal diagnosis through detection of fetal cells in maternal blood," Taiwan J Obstet Gynecol. 45(1):10-20 (Mar. 2006).
Ralston et al., "Estrogen inhibits release of tumor necrosis factor from peripheral blood mononuclear cells in postmenopausal women," Journal of Bone and Mineral Research. vol. 5, No. 9, pp. 983-988 (1990).
Reid et al., "The Blood Group Antigen Factsbook," (2nd Ed.) Elsevier Academic Press, London. 271-488, 2004.
Robertson et al., "Essential Role for IL-10 in Resistance to Lipopolysaccharide-Induced Preterm Labor in Mice," J. Immunol. 177: pp. 4888-4896 (2006) (10 pages).
Romero et al., "The natural interleukin-1 receptor antagonist in the fetal, maternal, and amniotic fluid compartments: the effect of gestational age, fetal gender, and intrauterine infection," Am. Jour. of Obstet. and Gynecology. 171 (4):912-921. (Abstract Only) (1994).
Romero et al., "The natural interleukin-1 receptor antagonist prevents interleukin-1 induced preterm delivery in mice," Am. Jour. of Obstet. and Gynecology. 167(4)(1): pp. 1041-1045 (Abstract Only) (Oct. 1992).
RosetteSep™., "Human Mesenchymal Stem Cell Enrichment Cocktail—Immunodensity Negative Selection Cocktail," Stemcell™ Technologies. downloaded from <http://www.stemcell.com/en/Products/All-Products/RosetteSep-Human-Mesenchymal-Stem-Cell-Enrichment-Cocktail.aspx> on Aug. 26, 2015 (2015) (3 pages).
Saliem et al., "Isolation and Characterization of Mesenchymal Stem Cells from Human Fetal Liver; Potential Candidates for Replacement Therapy in Liver Disease," J Liver: Dis Transplant. 1(2): 1-9, <http://dx.doi.org/10.4172/2325-9612.1000102> (2012).
Schaub et al., "TLR2 and TLR4 stimulation differentially induce cytokine secretion in human neonatal, adult, and murine mononuclear cells," Journal of Interferon & Cytokine Research. vol. 24(9), pp. 543-552 (2004) (17 pages).
Schlafer DH et al., "Effect of *Salmonella* Endotoxin Administered to the Pregnant Sheep at 133-142 Days Gestation on Fetal Oxygenation, Maternal and Fetal Adrenocorticotropic Hormone and Cortisol, and Maternal Plasma Tumor Necrosis Factor α Concentrations[1]," Biol of Repro. 50: pp. 1297-1302 (1994) (6 pages).
Sekizawa et al., "Development of noninvasive fetal DNA diagnosis from nucleated erythrocytes circulating in maternal blood," Prenat. Diagn. 27:846-848 (2007).
Sekizawa et al., "Fetal cell recycling: Diagnosis of gender and RhD genotype in the same fetal cell retrieved from maternal blood," Am J Obstet Gynecol. 181(5 Pt 1):1237-42 (Nov. 1999).
Simone, Nicole L. et al., "Technical Advance, Sensitive Immunoassay of Tissue Cell Proteins Procured by Laser Capture Microdissection," American Journal of Pathology. vol. 156, No. 2 (Feb. 2000) (8 pages).
Sitar et al., "Fetal Erythroblast Isolation Up to Purity from Cord Blood and Their Culture In Vitro," Cytometry. 35:337-345 (1999) (9 pages).
Sitar et al., "Physical Procedures For The Separation of Blood and Marrow Cells," Haematologica. 74:95-111 (1989).
Sitar et al., "Simultaneous fetal cell detection and genetic diagnosis by immuniphenotype and chromosomal fluorescence in situ hybridization (FISH)," American Journal of Obstetrics and Gynecology. 208(1):S246 (Jan. 2013) (1 page).
Sitar et al., "The use of non-physiological conditions to isolate fetal cells from maternal blood," Experimental Cell Research. 302:153-161 (2005).
Skogstrand et al., "Simultaneous measurement of 25 inflammatory markers and neurotrophins in neonatal dried blood spots by imunoassay with xMAP technology," Clin Chem., Oct. 2005, vol. 51, No. 10, pp. 1854-1866 (2005).
stemcell.com, Tissue Culture Reagents: HetaSep™ Product Datasheet [online], [Retrieved on Jun. 15, 2017, from <http://www.veritastk.co.jp/attached/1527/07086_07906-PIS.pdf>] (2009) (2 pages).
Talasaz, Amir Ali H. et al., "Isolating highly enriched populations of Circulating epithelial cells and other rare cells from blood using a magnetic sweeper device," Proc. Natl. Acad. Sci. USA. (Mar. 10, 2009), vol. 106, No. 10, pp. 3970-3975 (2009).
Tanavde et al., "Erythrocyte depletion of human umbilical cord blood using dextran sedimentation," Indian J. Med. Res. 106:16-9 (1997), English Abstract Only (1 page).
Thurm et al., "Measurement of cytokine production using whole blood," Curr. Protoc. Immunology. Chapter 7: Unit 7.18B (2005) (12 pages).
Tiblad et al., "Fetal stem-cell transplantation," Best Practice & Research Clinical Obstetrics and Gynaecology. 22(1): pp. 189-201, doi: 10.1016/j.bpobgyn.2007.07.007 (2008) (13 pages).
Tsang et al., "Dextran sedimentation in a semi-closed system for the clinical banking of umbilical cord blood," Transfusion. vol. 41 (3):344-52 (Mar. 2001), downloaded from <http://www.ncbi.nlm.nih.gov/pubmed/11274588> on Mar. 20, 2015 (9 pages).
Tulp et al., "A Separation Chamber to Sort Cells, Nuclei, and Chromosomes at Moderate g Forces. II. Studies on Velocity Sedimentation and Equilibrium Density Centrifugation of Mammalian Cells," Analytical Biochemistry. Vol. 117:354-365 (1981) (12 pages).
Vassiliadis et al., "Serum Levels of Pro- and Anti-Inflammatory Cytokines in Non-Pregnant Women, During Pregnancy. Labour and Abortion," Mediators of Inflammation. vol. 7, pp. 69-72 (1998).
Wachi et al., "Studies on preliminary concentration methods for recovery of fetal nucleated red blood cells in maternal blood," Congenit Anom (Kyoto). 44(4):196-203 (Dec. 2004).
Wang et al., "Fetal nucleated erythrocyte recovery: Fluorescence activated cell sorting-based positive selection using anti-gamma

(56) References Cited

OTHER PUBLICATIONS globin versus magnetic activated cell sorting using anti-CD45 depletion and anti-gamma globin positive selection," Cytometry. 39(3):224-30 (Mar. 2000).

Wetta et al., "168: Impaired anti-inflammatory response in women with a prior spontaneous preterm birth," American Journal of Obstetrics and Gynecology. 199(6): vol. 199, No. 6. p. S59 (Dec. 1, 2008).

Zheng et al., "Flow sorting of fetal erythroblasts using intracytoplasmic anti-fetal haemoglobin: preliminary observations on maternal samples," Prenat Diagn. 15(10):897-905 (Oct. 1995) (9 pages).

Zhu et al., "Detecting Cytokine Release from Single Human T-cells," NIH Public Access Author Manuscript, Anal. Chem. 81(19): 8150-B156, doi: 10.1021/ac901390j (Oct. 1, 2009) (15 pages).

Zhu et al., "Placental mesenchymal stem cells of fetal and maternal origins demonstrate different therapeutic potentials," Stem Cell Research & Therapy. 5(48):1-10, <http://stemcellres.com/content/5/2/48> (2014).

Zimmerman, Silke, "Development of a fetal specific antibody to characterize fetal erythroid cells". University of Hannover, 2004 (94 pages).

Zimmermann et al., "Unique monoclonal antibodies specifically bind surface structures on human fetal erythroid blood cells," Exp Cell Res. 319(17):2700-7 (Oct. 2013).

\* cited by examiner

Gates and Statistics

| Name | Events | %Parent | %Total |
|---|---|---|---|
| ☐ All Events | 1,009,737 | 0.00% | 100.00% |
| ☐ Lymphocytes + Monocytes | 648,019 | 64.18% | 64.18% |
| ☐ CD235a + | 878 | 0.14% | 0.09% |
| ☐ Triple Positive | 509 | 57.97% | 0.05% |

| Name | Events | %Parent | %Total |
|---|---|---|---|
| ☐ All Events | 151,921 | 0.00% | 100.00% |
| ☐ Lymphocytes + Monocytes | 93,554 | 61.58% | 61.58% |
| ☐ CD235a + | 44 | 0.05% | 0.03% |
| ☐ Triple Positive | 40 | 90.91% | 0.03% |

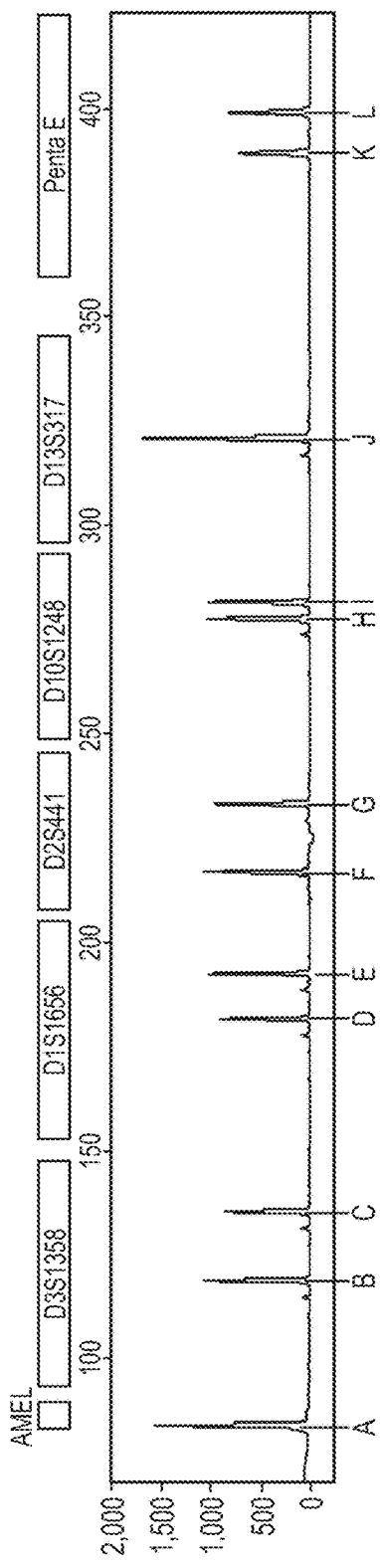
FIG. 19A Maternal gDNA
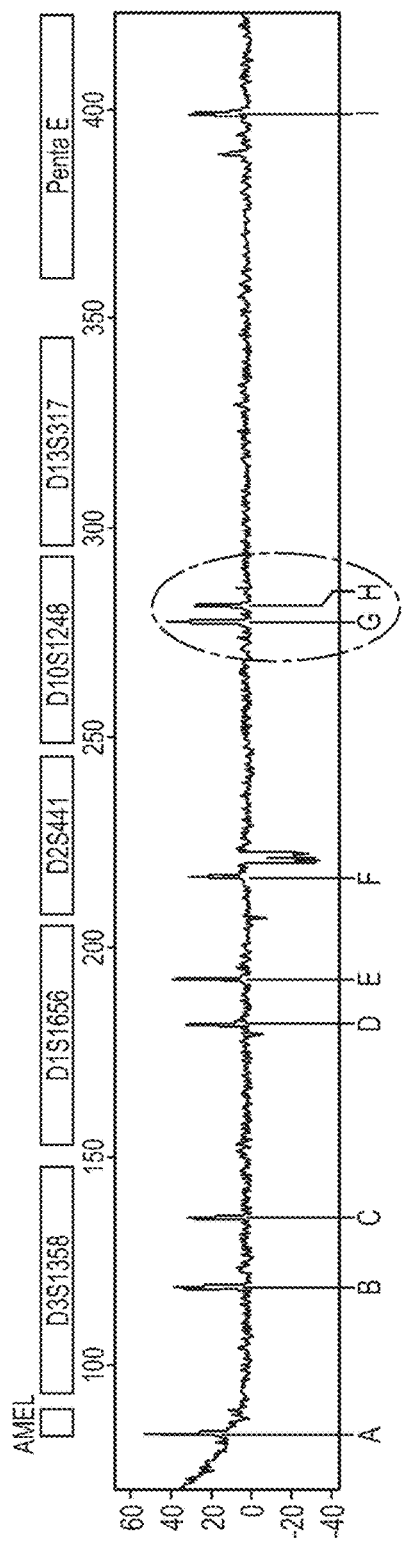
FIG. 19B Sample
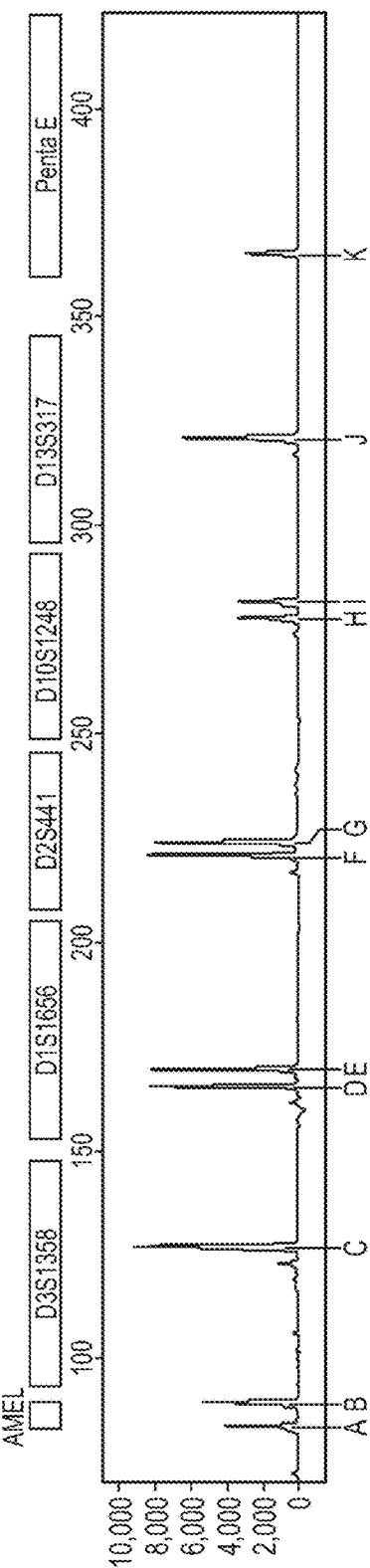
FIG. 19C Paternal gDNA

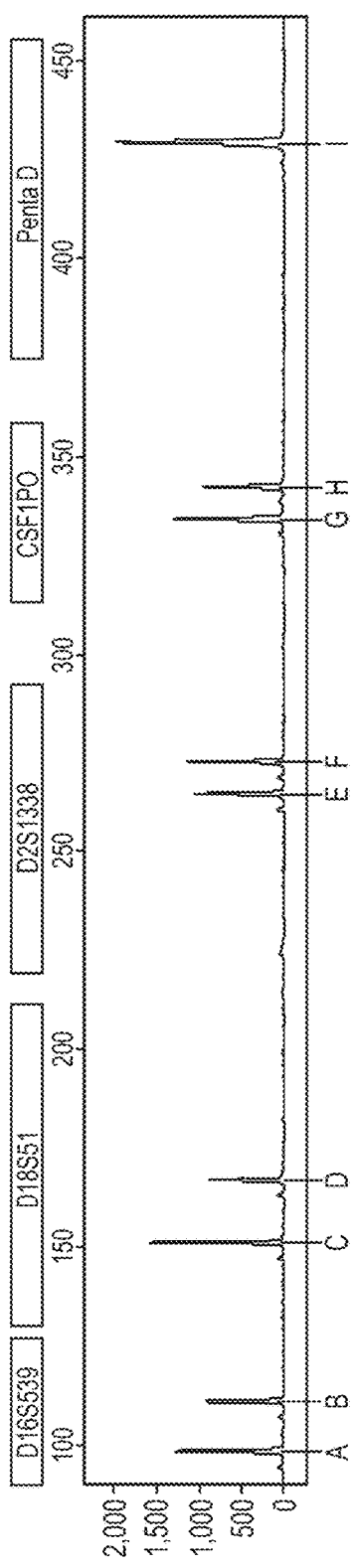
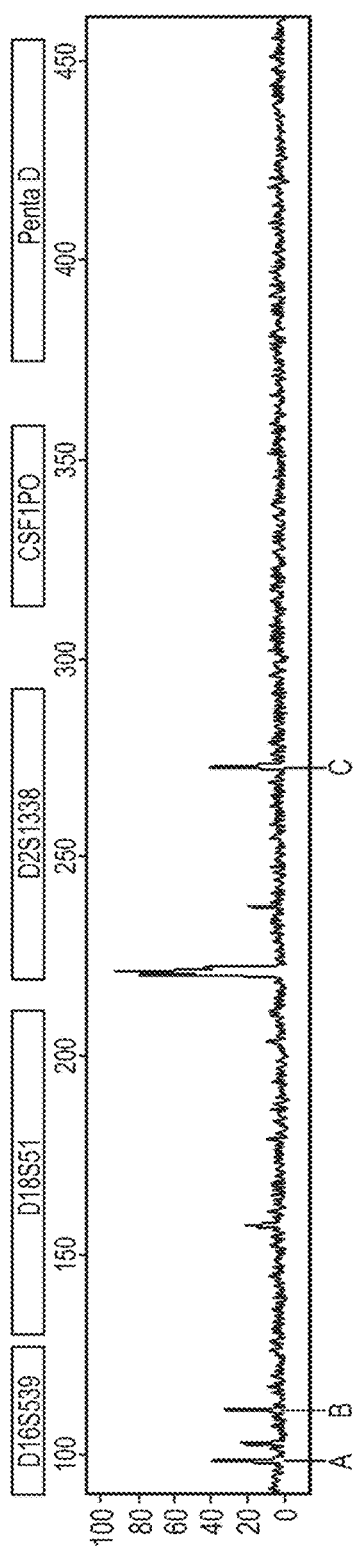
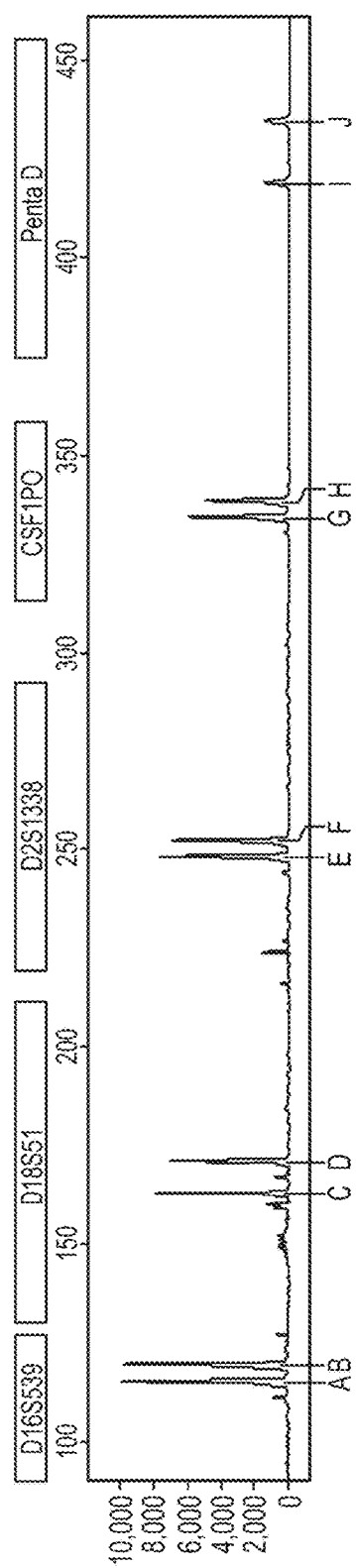

Maternal gDNA

Sample

Paternal gDNA

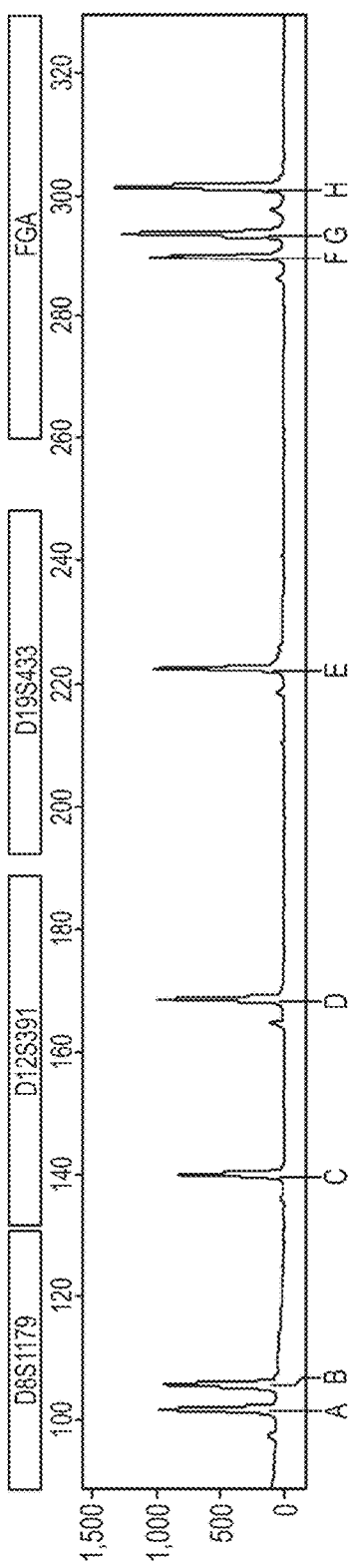
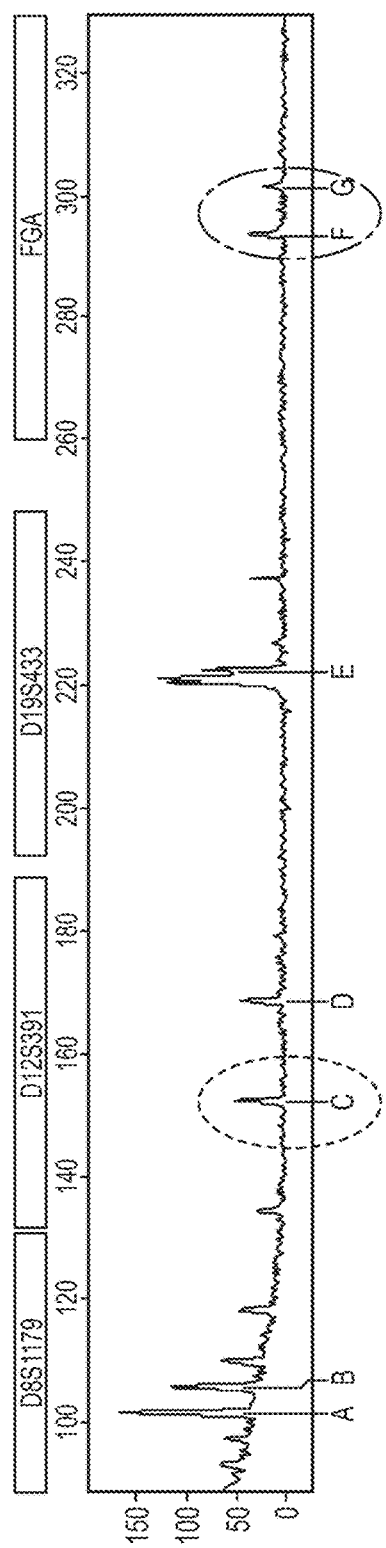
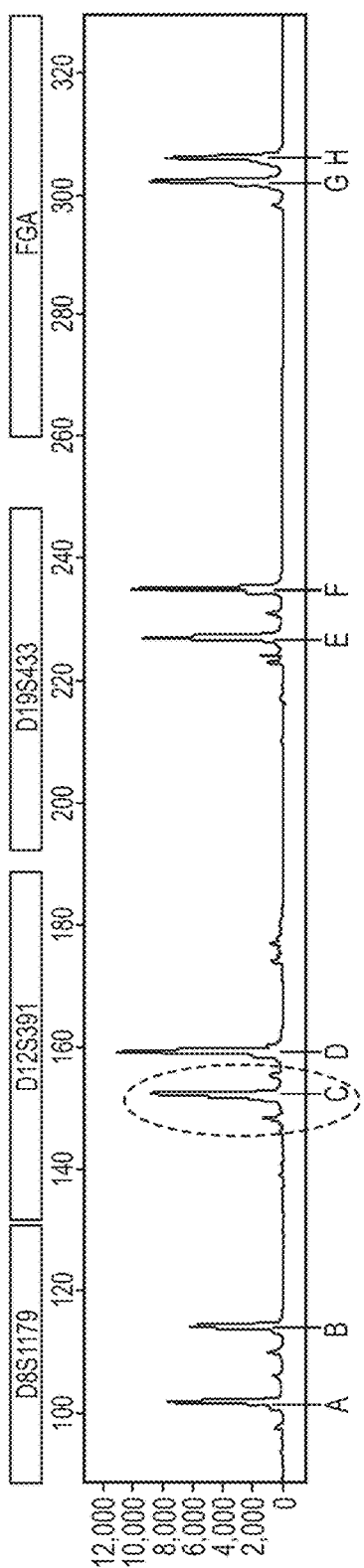
FIG. 22A Maternal gDNA
FIG. 22B Sample
FIG. 22C Paternal gDNA

PREPARATION OF FETAL NUCLEATED RED BLOOD CELLS (NRBCS) FOR DIAGNOSTIC TESTING

1. CROSS REFERENCE TO RELATED APPLICATIONS

The application is a continuation of U.S. application Ser. No. 17/585,820, filed Jan. 27 2022, which is a continuation of U.S. application Ser. No. 17/347,832, filed Jun. 15, 2021, now abandoned, which is a continuation of U.S. application Ser. No. 17/085,070, filed Oct. 30, 2020, now abandoned, which is a continuation of U.S. application Ser. No. 16/824,007 filed Mar. 19 2020, which is a continuation of U.S. application Ser. No. 16/237,179, filed Dec. 31, 2018, now abandoned, which is a continuation of U.S. application Ser. No. 14/934,382, filed Nov. 6, 2015, now abandoned, which is a continuation in part of U.S. application Ser. No. 14/710,460, filed May 12, 2015, now abandoned, which claims the priority benefit of U.S. provisional application No. 61/993,659, filed May 15, 2014, the contents of which are incorporated herein in their entireties by reference thereto.

2. BACKGROUND

The practice of prenatal diagnosis to detect possible chromosomal and genetic abnormalities of the fetus enables parents and caregivers to initiate monitoring of predispositions and early treatment of diseases or conditions. The practice of prenatal diagnosis has been established to detect possible chromosomal and genetic abnormalities of the fetus, thus enabling informed decisions by the parents and the care givers. Among various chromosomal abnormalities compatible with life (aneuploidy 21, 18, 13, X, Y), Down syndrome, caused by the presence of all or part of an extra copy chromosome 21, is the most common genetic cause of mental retardation and the primary reason for women seeking prenatal diagnosis (Pierce B. Genetics: A conceptual approach (W.H. Freeman and company, 2008), 3d edition; Driscoll and Gross, 2009, N Engl J Med. 360:2556-62). Cytogenetic disorders reportedly occur in about 1% of live births, 2% of pregnancies in women older than 35 years, and in approximately 50% of spontaneous first trimester miscarriage (Thompson and Thompson Genetics in Medicine, sixth edition, chapter 9). The incidence of single gene defects in a population of one million live births is reportedly about 0.36% (Thompson and Thompson Genetics in Medicine, sixth edition, chapter 9).

The preferred first trimester screening, involving quantification from serum of PAPP-A (pregnancy-associated plasma-protein-A), free β-Hcg (free β-human chorionic gonadotrophins), and ultrasound examination of nuchal translucency, has a Down syndrome detection rate of about 90%, but at the expense of a significant 5% false positive rate (Nicolaides et al., 2005, Ultrasound Obstet Gynecol 25:221-26). A meta-analysis of first trimester screening studies (Evans et al., 2007, Am J Obstet Gynecol 196:198-05) concluded that in practice the achievable sensitivity might be significantly lower (about 80-84%) than reported.

Definitive detection of chromosomal abnormalities and single gene disorders is possible by karyotype analysis of fetal tissues obtained by chorionic villus sampling, amniocentesis or umbilical cord sampling. To minimize risks of conditions such as Down syndrome, these tests are offered to women identified by a set of screening criteria as having the highest risk for fetal chromosomal abnormalities. This group generally includes pregnancies with maternal age of 35 or older and abnormal responses to ultrasound examinations of the fetus and/or maternal serum marker screening tests performed during first and/or second trimesters of pregnancy (Nicolaides et al., 2005, Ultrasound Obstet Gynecol 25:221-26). However, these procedures are highly invasive, require skilled professionals, and are prone to significant risk of fetal loss (up to 1%) and/or maternal complications (Mujezinovic et al., 2007, Obstet Gynecol 110:687-94; Tabor et al., 1986, Lancet 1:1287-93; Buscaglia et al., 1996, Prenat Diagn 16:375-76). A guideline by the American College of Obstetricians and Gynecologists (ACOG) advising its members to test all expected mothers for genetic abnormalities (ACOG Practice bulletin Clinical Management Guidelines for Ob-Gyns, No. 7, January 2007) is an indication of the unmet need for non-invasive technologies that could safely lead to specific diagnosis of fetal genetic status.

For several decades, the search for non-invasive alternatives has focused on isolation, identification, and subsequent analysis of fetal genetic materials that normally cross the placental barrier into maternal circulation. Since the pioneering reports on detection of fetal cells in 1893 and later of fetal cell-free DNA and in maternal blood (see Table 1 of Purwosunu et al., 2006, Taiwanese J. Obstet Gynecol 45(1): 10-20, two promising approaches based on analysis of fetal cells or cell free fetal genetic materials has received tremendous interest.

"Cell-free" fetal DNA is relatively abundant in maternal blood, constituting 5-10% of the total cell-free DNA in maternal plasma (Hahn et al., 2011, Expert Reviews in Molecular Medicine 13:e16). Cell-free DNA-based prenatal testing, which become viable with the advent of next generation sequencing techniques, first became commercially available in the U.S. in 2011, and at least four such assays are currently commercialized. To date cell-free DNA testing methods permit gender identification, aneuploidy detection and mutations present in paternal DNA, but not more refined genetic analyses, such as detection of microdeletions or microinsertions (see, e.g., Simpson, 2013, Fertility and Sterility 99:1124-1134). Moreover, inaccurate test results, including false positives, though infrequent, have been reported (see Simpson, 2013, Fertility and Sterility 99(4): 1124-1134; Dugo et al., 2014, J Prenat Med. 8(1-2):31-35).

In comparison to cell-free fetal DNA or RNA, intact fetal cells can provide access to complete fetal genetic materials important for detection of chromosomal abnormalities as well as a more complete assessment of fetal genetic status (Huang et al., 2011, J Cell Biochem. 112:1475-85). A number of significant challenges have hampered development of reliable fetal cell isolation methods. The major limitation for isolation is the low number of circulating fetal nucleated cells in maternal blood, with estimates ranging from 1-2 fetal cells per mL of maternal blood (Bianchi et al., 1997, Am J Hum Genet 61(4):822-829) to 2-6 per mL of maternal blood (Krabchi et al., 2001, Clin Genet 60:145-150), although the numbers have been reported to be up to six-fold greater in aneuploidy pregnancies (Krabchi et al., 2006, Clin Genet 69:145-154 and Bianchi et al., 1997, Am J Hum Genet 61(4):822-829). To put this number into perspective, the ratio of fetal cells to maternal cells in blood has been estimated at 1 in $10^5$ to 1 in $10^9$ (see Purwosunu et al., 2006, Taiwanese J. Obstet Gynecol 45(1):10-20; Simpson, 2013, Fertility and Sterility 99(4):1124-1134), and for each 1-6 fetal cells in 1 mL of maternal blood there are approximately $4.2\text{-}5.4 \times 10^9$ adult red blood cells, $1.16\text{-}8.3 \times 10^3$ neutrophils, $2\text{-}9.5 \times 10^5$ monocytes, $1\text{-}4.8 \times 10^6$ lymphocytes, $1.33\text{-}3.33 \times 10^8$ platelets, up to $4.5 \times 10^5$ eosinophils and up to 2×10⁵ basophils (numbers taken from Uthman, Blood Cells and the CBC, which can be accessed at web2.iadfw.net/uthman/blood_cells.html).

Among variety of fetal cells in maternal blood (trophoblasts, lymphocytes, nucleated red blood cells, and hematopoietic stem cells; see Bianchi, 1999, Br J Haematol 105:574-83), nucleated red blood cells (NRBCs), known also as erythroblasts, have most of the desired characteristics for a reliable prenatal assay. Fetal NRBCs (fNRBCs) have limited life span and proliferative capacity (and therefore do not persist from one pregnancy to another), are mononucleated, carry a representative complement of fetal chromosomes, and are consistently present in maternal blood (Huang et al., 2011, J Cell Biochem. 112:1475-85; Kavanagh et al., 2010, J Chromat B 878:1905-11; Bianchi, 1999, Br J Haematol 105:574-83; Choolani et al., 2003, Mol Hum Repro 9:227-35; Bianchi and Lo, 2010, in Genetic Disorders and the Fetus: Diagnosis, Prevention and Treatment, Sixth Edition, Ch. 30, pp. 978-1000 (Milunsky and Milunsky eds.)). Studies of fetal erythropoiesis have identified two distinct processes, occurring initially in yolk sack (primitive erythropoiesis, producing primitive erythroblasts) and subsequently in fetal liver and bone marrow (producing definitive erythroblasts) (Huang et al., 2011, J Cell Biochem. 112:1475-85). Both primitive and definitive erythroblasts have been detected in maternal circulation, with primitive erythroblasts being the predominant first trimester cell type that is progressively replaced by the definitive type that persists until term (Huang et al., 2011, J Cell Biochem. 112:1475-85; Choolani et al., 2003, Mol Hum Repro 9:227-35).

The most extensive study of fetal cells in maternal blood was the multi-year, multi-center NIFTY Trial, which was designed to evaluate the utility and feasibility of isolating fetal cells to diagnose fetal abnormalities. The four centers involved attempted to isolate fetal cells from maternal blood and analyze the isolated cells by fluorescent in situ hybridization (FISH) with chromosome-specific probes (Bianchi et al., 2002, Prenat Diagn 22:609-615). The four centers, designated A, B, C and D, all used density gradient separation as a preliminary step to deplete maternal cells and then used different methods to obtain fetal cells for FISH. At center A, density separation was followed by cell fixation, negative selection by MACS using anti-CD14 and anti-CD15 antibodies, and FACS using anti-HbF (fetal hemoglobin). At center B, density gradient separation was followed by cell fixation and simultaneous negative and positive selection using FACS with anti-HbF antibodies for positive selection and anti-CD45 or anti-HbA (adult hemoglobin) for negative selection. At center C, density gradient separation was followed by negative selection by MACS using anti-CD14 and anti-CD45 antibodies, FACS using anti-CD71 antibodies, and cell fixation. At center D, density gradient separation was followed by cell fixation and positive selection using MACS with anti-CD71 antibodies. The general detection rate of X and Y chromosomes in male fetal cells was only 41.1% of cases, and the false positive rate (i.e., detection of X and Y chromosomes in female fetal cells) was 11.1%. The overall detection rate of aneuploidies was 74.4%, with a false positive rate estimated to be between 0.6% and 4.1%. See Bianchi et al., 2002, Prenat Diagn 22:609-615. The MACS-based methods were said to provide better recovery and detection than FACS-based methods (Bianchi and Lo, 2010, in Genetic Disorders and the Fetus: Diagnosis, Prevention and Treatment, Sixth Edition, Ch. 30, pp. 978-1000 (Milunsky and Milunsky eds.)). One of the NIFTY Trial's contributors stated that the approach "was laborious, lacked consistent recovery, and had an unacceptable non-informative rate." Simpson, 2013, Fertility and Sterility 99(4):1124-1134.

A variety of other approaches have to been utilized to isolate fetal cells, including centrifugation, filtration, lateral displacement, magnetophoresis, lectin-binding, dielectrophoresis, micromanipulation and laser capture, and microdissection. Higher throughput methods, such as microelectronic mechanical systems (MEMS) and automated cell enrichment methods, have also been utilized (Kavanagh et al., 2010. J Chromat B 878:1905-11; Kilpatrick et al., 2004, J Obstet Gynecol 190:1571-81; Seppo et al., 2008, Prenat Diagn 28:815-21; Talasaz et al., 2009, PANS 106:3970-75, 2009; Kumo et al., 2010, 14th International Conference on Miniaturized Systems for Chemistry and Life Sciences. 3-7 Oct. 2010, Groningen, The Netherlands; pp. 1583-1585; Cheng et al., 2011, J Clin Lab Anal 25:1-7; Choolani et al., 2012, Best Practice & Research Clinical Obstetrics and Gynaecology 26:655-667). These too have provided inconsistent results (Simpson, 2013, Fertility and Sterility 99(4): 1124-1134).

Thus, a need for simple reliable fetal cell isolation technology that permits downstream genetic analysis of fetal DNA still exists.

3. SUMMARY

The present disclosure is based on the development of isolation techniques that permit enrichment and isolation of fetal nucleated red blood cells (fNRBCs) from a mixed cell population in which the fNRBCs are a vast minority. Accordingly, the present disclosure provides cell preparations highly enriched for fNRBCs and methods of producing such enriched cell populations.

The present disclosure is based, in part, on the use of positive selection methods, typically carried out in a fluid medium, to enrich for (and optionally isolate) fNRBCs from a biological sample, such as maternal blood or an fNRBC-enriched cell fraction of maternal blood. The maternal blood is typically drawn in the time period starting at around four weeks of gestation.

The positive selection methods, which typically include one or more positive immunoselection based steps, can be used in conjunction with one or more other methods that deplete other cell types, e.g., maternal lymphocytes or red blood cells, from the biological sample. Such other methods include negative selection and cell density separation techniques.

Typically, the negative selection methods entail one or more negative immunoselection steps utilizing an antibody that does not specifically bind to fNRBCs but binds to one or more other cell types that may be present in the biological sample.

Once a preparation of cells enriched in fNRBCs is made, the preparation itself can be subject to diagnostic testing, or additional isolation techniques (e.g., micromanipulation) can be utilized to select individual fNRBCs for diagnostic testing. One or more of the fNRBCs can be subject to a validation technique, such as short tandem repeat ("STR") analysis, to confirm the identity of the cell as a fetal cell.

In some aspects, the present disclosure provides a method for preparing fNRBCs, comprising subjecting a biological sample comprising fNRBCs to positive selection. The positive selection preferably includes positive immunoselection and optionally one or more additional positive selection criteria. The positive immunoselection typically comprises the steps of: (a) contacting the biological sample with one or more positive immunoselective antibodies (e.g., one, two, three or more positive immunoselective antibodies) in a fluid medium, wherein the positive immunoselective antibody selectively binds to fNRBCs relative to one or more other cell types in the biological sample; and (b) selecting cells bound to said positive immunoselective antibody/antibodies. Illustrative embodiments of positive selection into which the foregoing positive selection steps can be incorporated are described in Sections 5.3, 6, 7.3 and 7.5.

In certain aspects, at least one positive immunoselective antibody binds an antigen present on the surface of fNRBC nucleated precursor cells but does not bind CD71 or other surface antigens present on adult erythroid cells. In some embodiments, the positive immunoselective antibody is 4B9 or an antibody that competes with 4B9 for binding to the surface of fNRBC nucleated precursor cells. Other markers for positive selection can include glycophorin A (also known as CD235a), CD36, CD71, and nuclear stains (e.g., Hoechst 33342, LDS751, TO-PRO, DC-Ruby, and DAPI). Multiple positive selection processes can be used, e.g., positive selection using MACS followed by positive selection using FACS, each utilizing one, two, three or even more positive selection (e.g., positive immunoselection) reagents such as antibodies against the markers or the nuclear stains identified above.

The positive selection can be used in conjunction with negative selection, typically negative immunoselection. Negative immunoselection can comprise the steps of: (a) contacting the biological sample with a negative immunoselective antibody in a fluid medium, wherein the negative immunoselective antibody selectively binds other cells in the biological sample relative to fNRBCs; and (b) selecting cells not bound to said negative immunoselective antibody. Illustrative embodiments of negative selection into which the foregoing negative selection steps can be incorporated are described in Sections 5.3, 6, 7.2 and 7.5.

The negative selection, if carried out, can be performed before, after or concurrently with the positive selection. One or more negative immunoselective antibodies can be used, preferably against one or more haematopoietic cell surface markers. Exemplary cell surface markers include: (a) a T-lymphocyte cell surface marker such as CD3, CD4 or CD8; (b) a B-lymphocyte cell surface marker such as CD19, CD20, or CD32; (c) a pan lymphocyte marker such as CD45; (d) an NK cell surface marker such as CD56; (e) a dendritic cell surface marker such as CD11c or CD23; and (f) a macrophage or monocyte cell surface marker such as CD14 or CD33. In particular embodiments, two, three, four, five or even more negative immunoselective antibodies are used, in one, two or more negative selection processes.

The immunoselection step can utilize magnetic separation, e.g., using antibody-coated magnetic beads, or flow cytometry. Flow cytometric techniques can provide accurate separation via the use of, e.g., fluorescence activated cell sorters, which can have varying degrees of sophistication, such as multiple color channels, low angle and obtuse light scattering detecting channels, impedance channels, etc. Accordingly, as used herein, the term "flow cytometry" encompasses fluorescent activated cell sorting (FACS).

To improve enrichment for fNRBCs, a pre-enrichment process, such as density separation, can be used, prior to positive selection. Exemplary pre-enrichment processes are described in Sections 5.2 and 7.1.

Once a preparation of cells enriched in fNRBCs is made, the preparation itself can be subject to a diagnostic assay, or additional isolation techniques (e.g., micromanipulation, capture of the cells on a solid surface) can be utilized to select individual fNRBCs or pools of fNRBCs for diagnostic testing. In some embodiments, the additional isolation techniques (e.g., micromanipulation) can take advantage of the fluorescent labels utilized to enrich the cells, the presence of hemoglobin in the fNRBCs (detectable by a Soret band filter) and fNRBC morphological features (Huang et al., 2011, J Cell Biochem. 112:1475-85; Choolani et al., 2003, Mol Hum Repro 9:227-35). Exemplary approaches for micromanipulation are described in Sections 5.4 and 7.6.

The present disclosure further provides preparations of fNRBCs prepared or obtainable by the methods described herein, including individual fNRBCs or groups of fNRBCs isolated by the methods described herein. In some embodiments, the disclosure provides a FACS-sorted cell population containing fNRBCs. Exemplary FACS sorted populations are described in Section 5.5.

The fNRBCs can be used in fetal diagnostic testing, e.g., for determining the presence of a multiple pregnancy or a fetal abnormality. Examples of abnormalities that can be tested for include trisomy 13, trisomy 18, trisomy 21, Down syndrome, neuropathy with liability to pressure palsies, neurofibromatosis, Alagille syndrome, achondroplasia, Huntington's disease, alpha-mannosidosis, beta-mannosidosis, metachromatic leucodystrophy, von Recklinghausen's disease, tuberous sclerosis complex, myotonic dystrophy, cystic fibrosis, sickle cell disease, Tay-Sachs disease, beta-thalassemia, mucopolysaccharidoses, phenylketonuria, citrullinuria, galactosemia, galactokinase and galactose 4-epimerase deficiency, adenine phosphoribosyl, transferase deficiency, methylmalonic acidurias, proprionic acidemia, Farber's disease, fucosidosis, gangliosidoses, gaucher's disease, I cell disease, mucolipidosis III, Niemann-Pick disease, sialidosis, Wolman's disease, Zellweger syndrome, cystinosis, factor X deficiency, ataxia telangiectasia, Bloom's syndrome, Robert's syndrome, xeroderma pigmentosum, fragile (X) syndrome, sex chromosome aneuploidy, Klinefelter's Syndrome, Turner's syndrome, XXX syndrome, steroid sulfatase deficiency, microphthalmia with linear skin defects, Pelizaeus-Merzbacher disease, testis-determining factor on Y, ornithine carbamoyl transferase deficiency, glucose 6-phosphate dehydrogenase deficiency, Lesch-Nyhan syndrome, Anderson-Fabry disease, hemophilia A, hemophilia B, Duchenne type muscular dystrophy, Becker type muscular dystrophy, dup(17)(p11.2p11.2) syndrome, 16p11.2 deletion, 16p11.2 duplication, Mitochondrial defect, dup(22)(q11.2q11.2) syndrome, Cat eye syndrome, Cri-du-chat syndrome, Wolf-Hirschhorn syndrome, Williams-Beuren syndrome, Charcot-Marie-Tooth disease, chromosome rearrangements, chromosome deletions, Smith-Magenis syndrome, Velocardiofacial syndrome, DiGeorge syndrome, 1p36 deletion, Prader-Willi syndrome, Azospermia (factor a), Azospermia (factor b), Azospermia (factor c), spina bifida, anencephaly, neural tube defect, microcephaly, hydrocephaly, renal agenesis, Kallmann syndrome, Adrenal hypoplasia, Angelman syndrome, cystic kidney, cystic hygroma, fetal hydrops, exomphalos and gastroschisis, diaphragmatic hernia, duodenal atresia, skeletal dysplasia, cleft lip, cleft palate, argininosuccinicaciduria, Krabbe's disease, homocystinuria, maple syrup urine disease, 3-methylcrotonyl coenzyme A, carboxylase deficiency, Glycogenoses, adrenal hyperplasia, hypophosphatasia, placental steroid sulphatase deficiency, severe combined immunodeficiency syndrome, T-cell immunodeficiency, Ehlers-Danlos syndrome, osteogenesis imperfect, adult polycystic kidney disease, Fanconi's anemia, epidermolysis bullosa syndromes, hypohidrotic ectodermal dysplasia, congenital nephrosis (Finnish type) and multiple endocrine neoplasia.

The diagnostic assay can be a nucleic acid (e.g., DNA or RNA) assay, a protein (e.g., antibody-based) assay, or a histology assay, or a combination thereof. Examples of DNA assays include FISH, PCR and DNA sequencing assays. Examples of RNA assays include RT-PCR assay and FISH assays. To facilitate access to the nucleic acid, the fNRBCs can be lysed or permeabilized prior to carrying out the diagnostic test. The DNA, RNA and protein assays can be performed on a microarray. Exemplary techniques for molecular diagnostic testing are described in Section 5.7.

The diagnostic assay can be preceded, accompanied or followed by a molecular validation technique to confirm the identity of the cell or cell population being diagnosed as fetal cell(s). Exemplary validation techniques are described in Section 5.6.

The methods described herein can be performed once or multiple times during a given pregnancy, e.g., to confirm a particular diagnosis or to detect changes in the pregnancy or the condition of the fetus.

Kits useful for practicing the methods of the disclosure are described in Section 5.8.

4. BRIEF DESCRIPTION OF THE FIGURES

FIG. 1: FIG. 1 shows an exemplary fNRBC isolation and downstream analysis work flow. For the fNRBC isolation, a preferred work flow includes isolation of mononuclear cells from maternal blood on a cell density gradient as described in Section 7.1, utilizing positive selection (e.g., enriching for 4B9 positive cells using magnetic activated cell sorting) as described in Section 7.3 (with or without the negative selection, e.g., CD45 depletion step, of Section 7.2, which is optional), and sorting for CD235+, nuclear-stained, 4B9-positive cells. Following enrichment of fNRBC, individual cells can be selected, e.g., on the basis of morphology or staining as described in this application for downstream cytogenetic and/or molecular analysis, according to the methods described herein. The workflows can be adapted to take advantage of any of the combination protocols outlined in Section 7.

Figure 2:
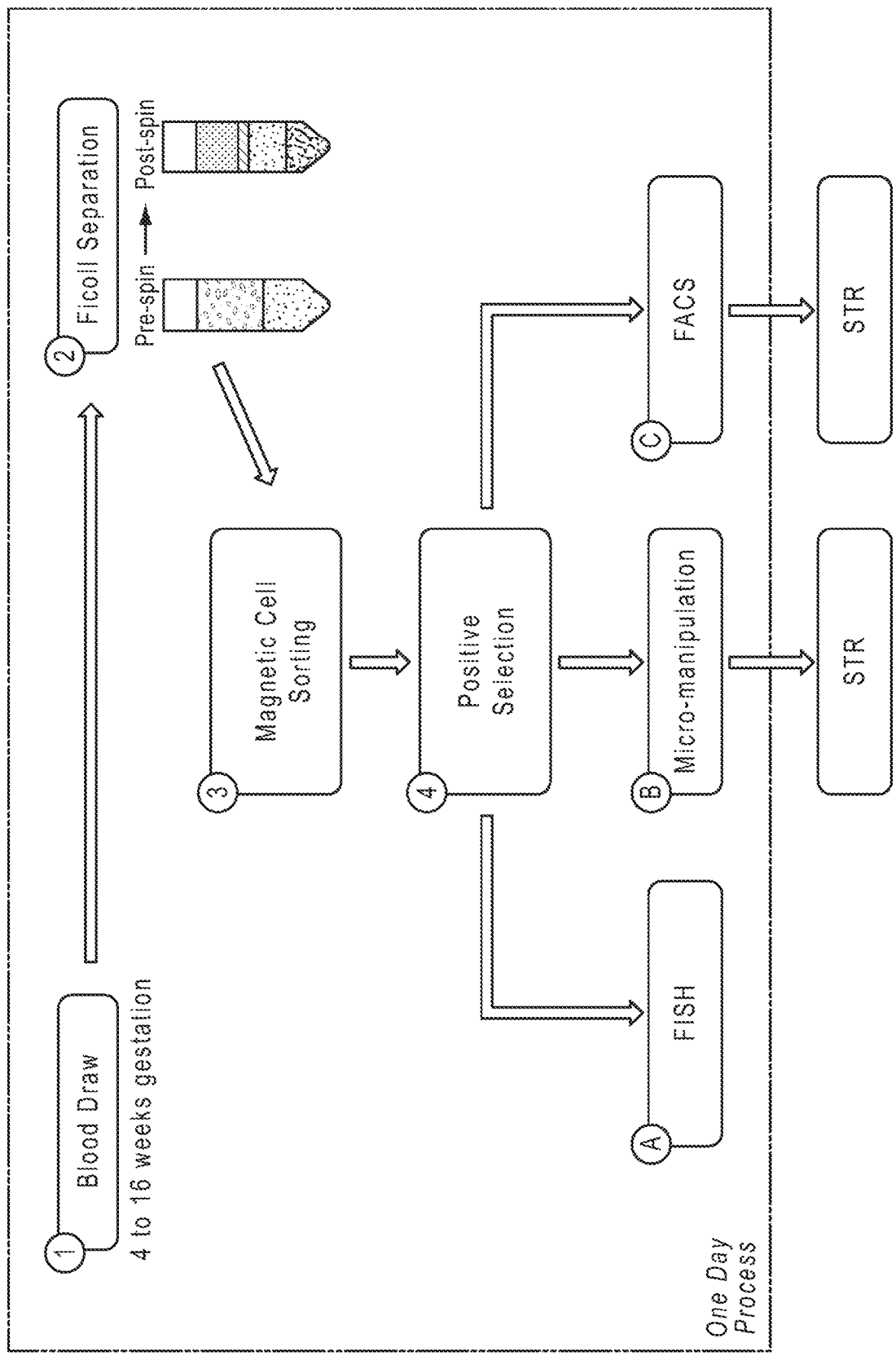

FIG. 2: FIG. 2 shows specific embodiments of the workflows outlined in FIG. 1.

Figure 3A:
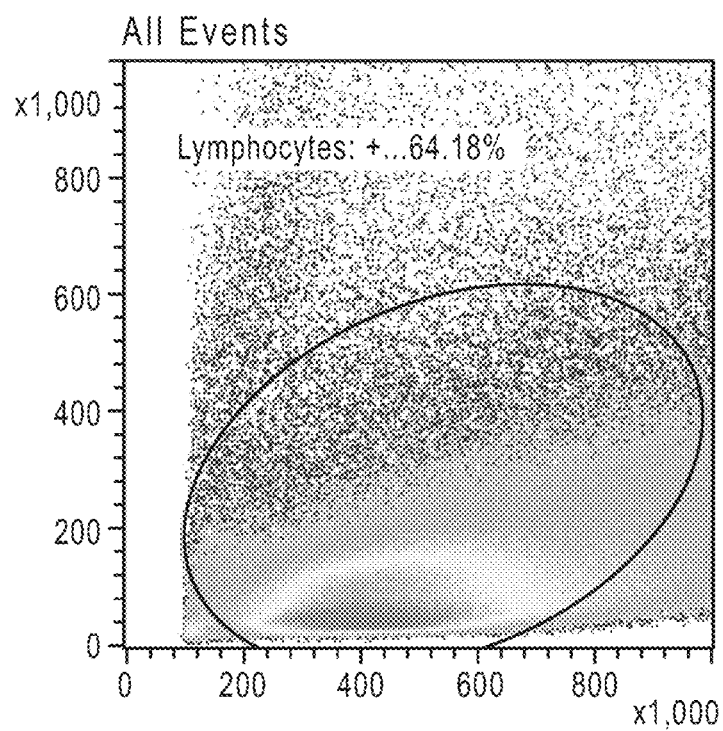
Figure 3B:
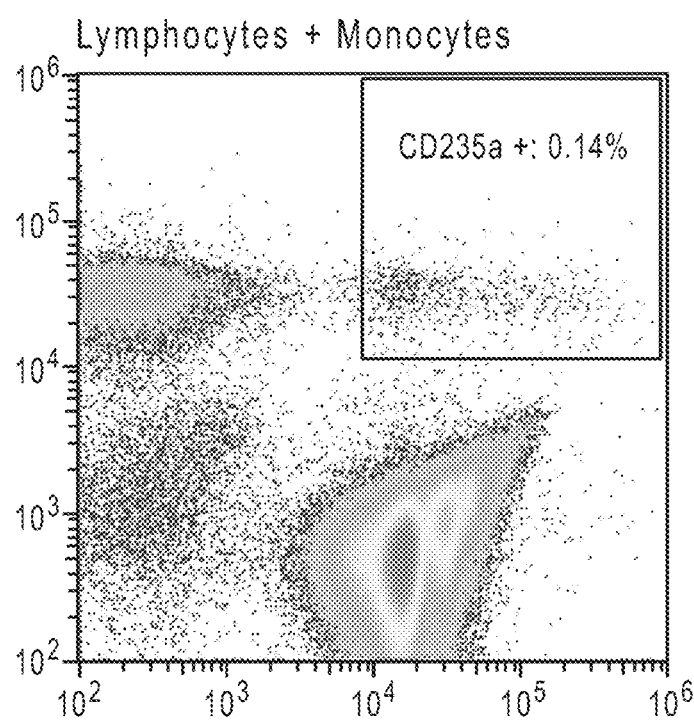
Figures 3C, 3D:
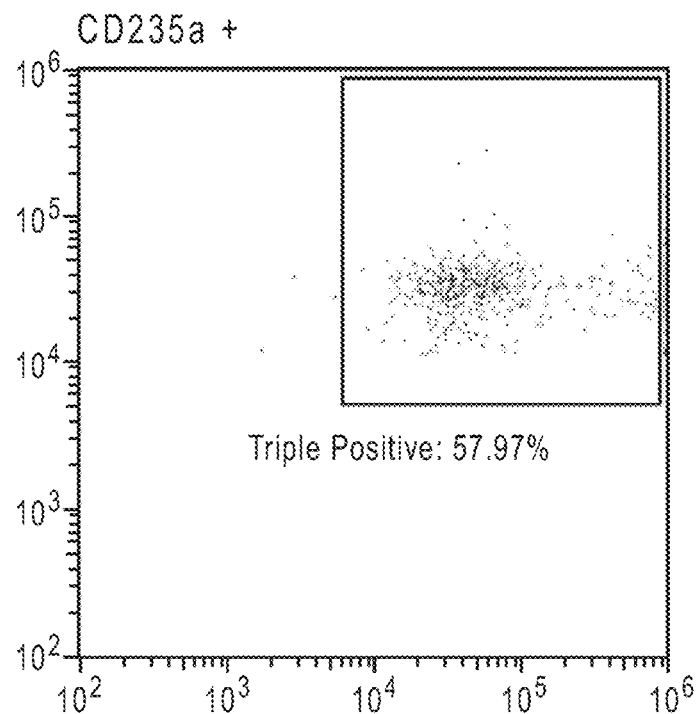

FIGS. 3A-3D: FIGS. 3A-3D show an exemplary FACS dataset utilizing the methods disclosed herein to isolate fNRBCs from maternal blood. FIG. 3A shows the correlated measurements of FSC (X axis) and BSC (Y axis) using light scattering properties of the cell to differentiate cell types. FIG. 3B is a sub-gate of the lymphocytes and monocytes. The X axis represents CD235a staining and the Y axis represents DC-Ruby staining. The upper right quadrant contains events that are nuclear DC-Ruby and CD235a PE (glycophorin-a) positive. FIG. 3C is a sub-gate of the CD235a+ region. The X axis represents AF 488 staining and the Y axis represents DC-Ruby staining. The upper right quadrant contains events that are positive for nuclear DC-Ruby and 4B9 AF 488. These cells can be sorted for downstream analysis, for example directly into a PCR tube for nucleic acid amplification or on a slide for micromanipulation. FIG. 3D shows an exemplary distribution of cells selected at the different gating levels shown in FIGS. 3A-C.

Figure 4:
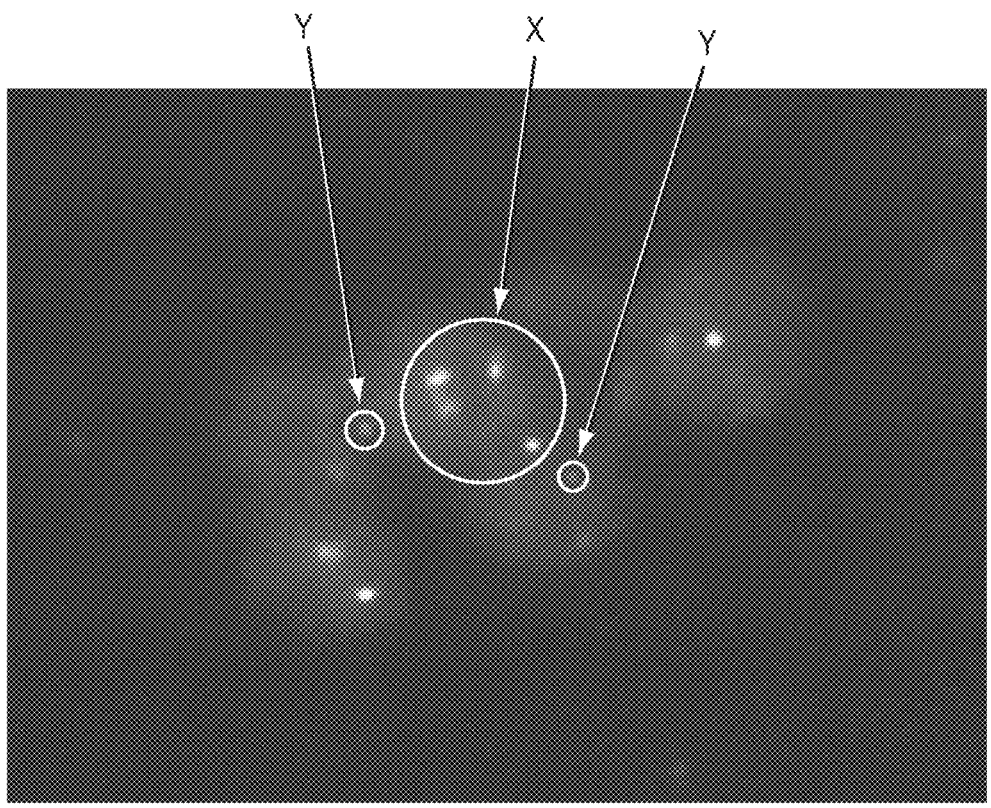

FIG. 4: fNRBCs analyzed by fluorescence in-situ hybridization (FISH) using X and Y chromosomal hybridization probes and counterstained with DAPI.

Figure 5:
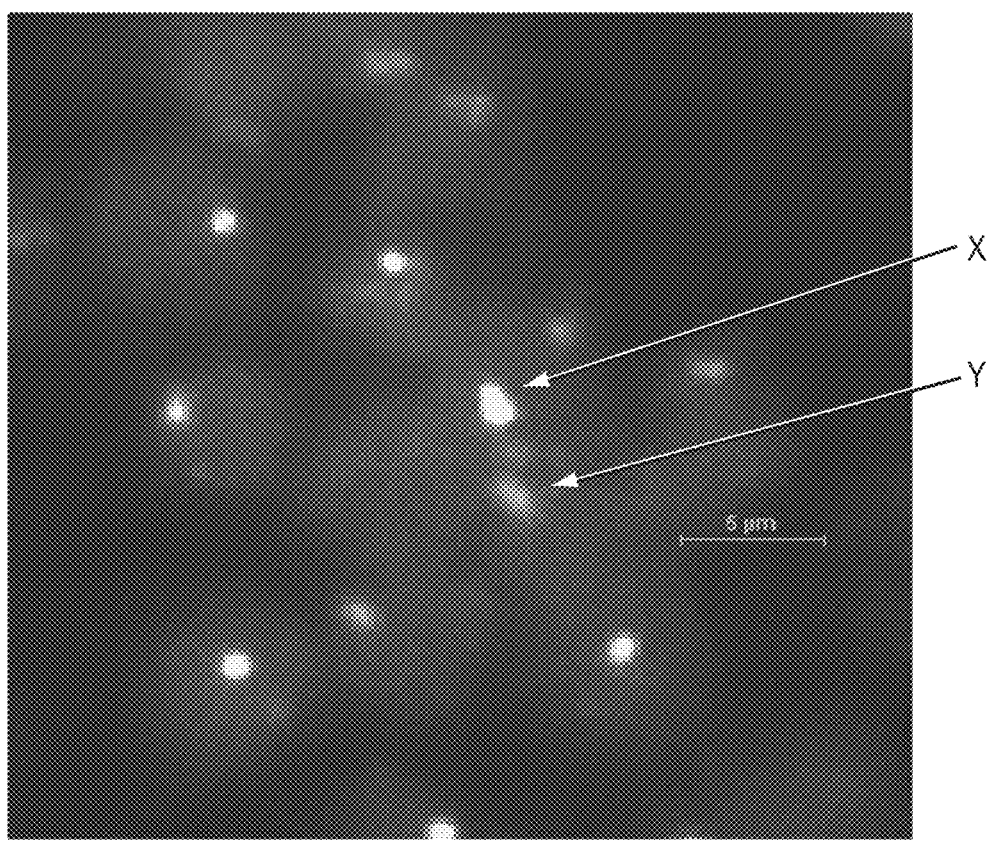

FIG. 5: Cells isolated from peripheral blood of a female pregnant with a male fetus. Cells were hybridized with X and Y probes and counterstained with a nuclear stain, DAPI.

Figure 6:
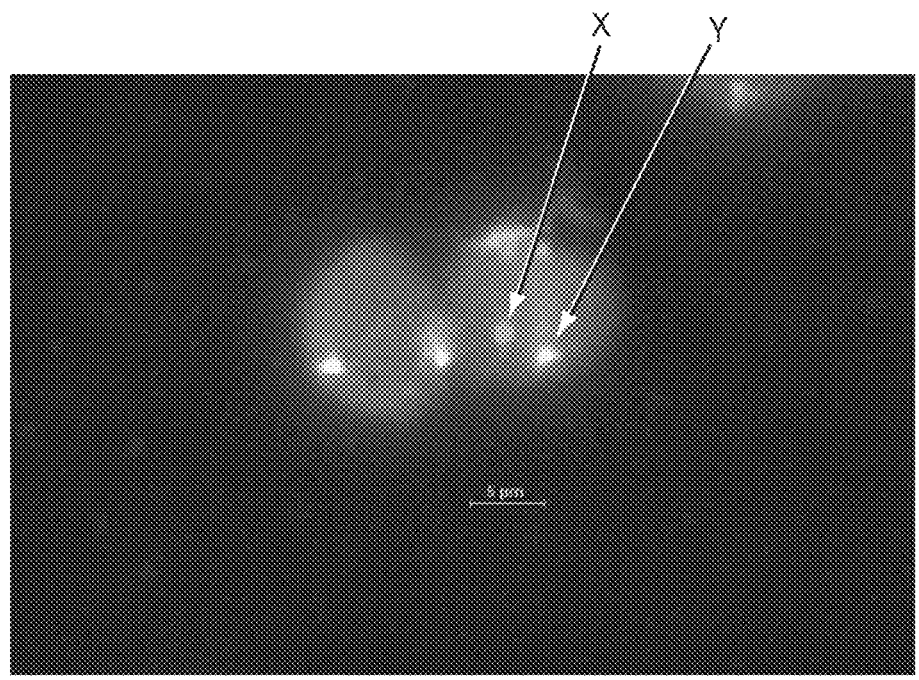

FIG. 6: Cells isolated from peripheral blood of a female pregnant with a male fetus. Cells were hybridized with X and Y probes and counterstained with a nuclear stain, DAPI.

Figure 7A:
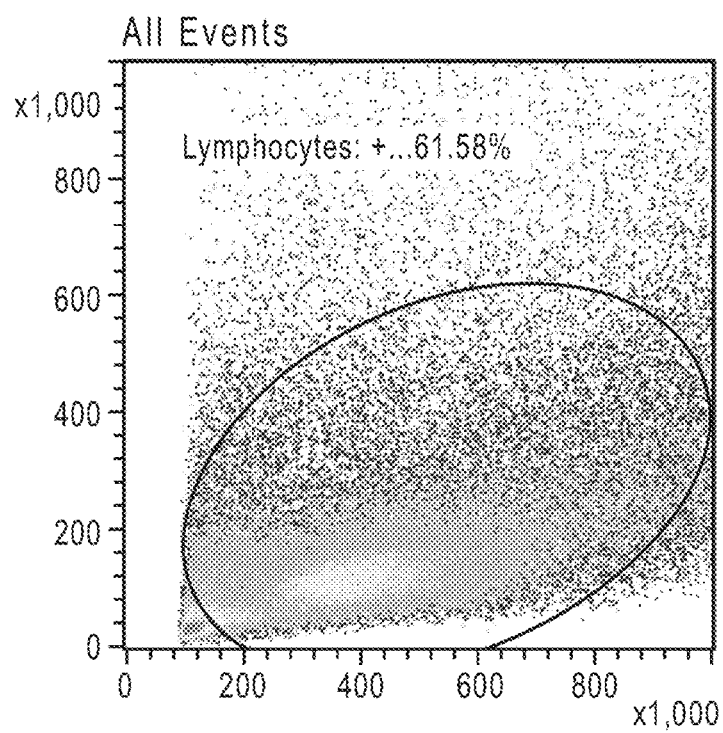
Figure 7B:
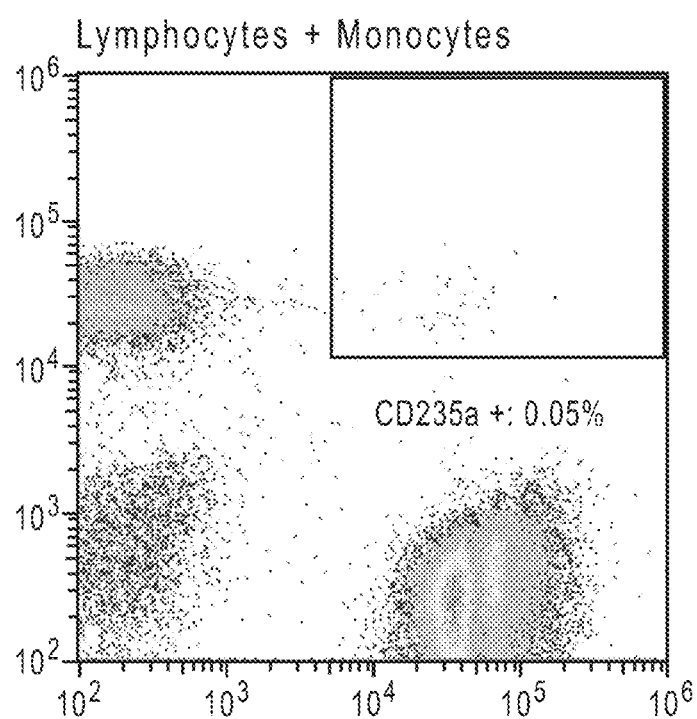
Figures 7C, 7D:
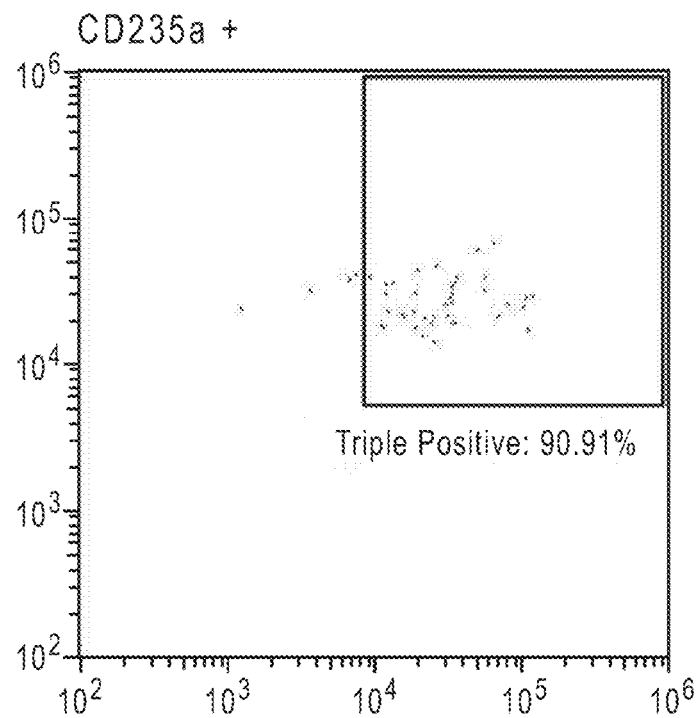

FIGS. 7A-D: FIG. 7A shows the correlated measurements of FSC (X axis) and BSC (Y axis) using light scattering properties of the cell to differentiate cell types. FIG. 7B is a sub-gate of the lymphocytes and monocytes. The X axis represents CD235a staining and the Y axis represents DC-Ruby staining. The upper right quadrant contains events that are nuclear DC-Ruby and CD235a PE (glycophorin-a) positive. FIG. 7C is a sub-gate of the CD235a+ region. The X axis represents AF 488 staining and the Y axis represents DC-Ruby staining. The upper right quadrant contains events that are positive for nuclear DC-Ruby and 4B9 AF 488. FIG. 7D is the statistics for each different level of gating.

Figure 8A:
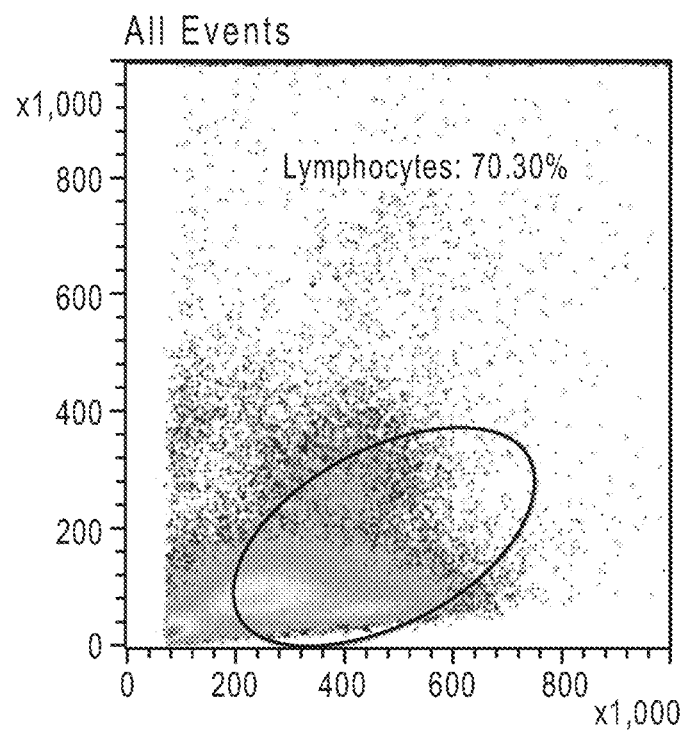
Figure 8B:
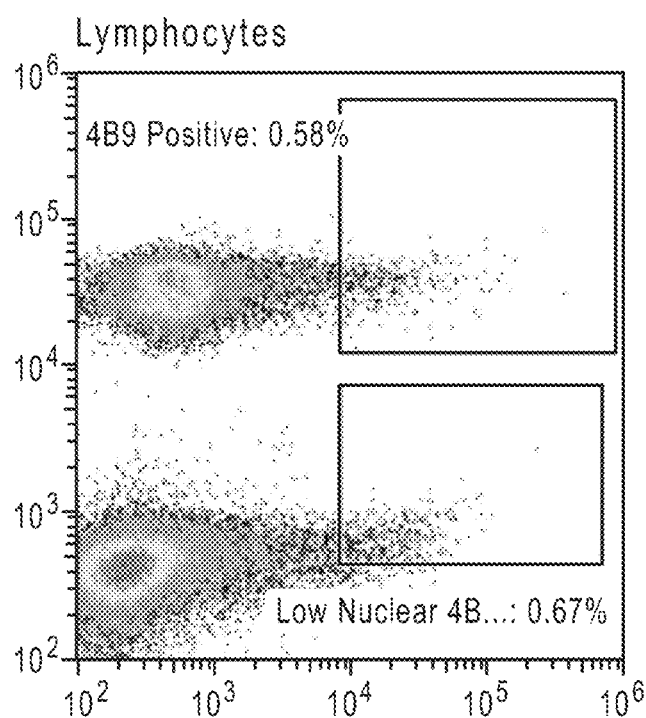

FIGS. 8A-B: FIG. 8A shows the correlated measurements of FSC (X axis) and BSC (Y axis) using light scattering properties of the cell to differentiate cell types of 4B9 negative cell fraction sorted by fluorescence activated cell sorting (FACS). FIG. 8B shows the FACS sub-gate of lymphocytes from 4B9 negative cell fraction. The X axis represents AF 488 staining and the Y axis represents DC-Ruby staining.

Figure 9A:
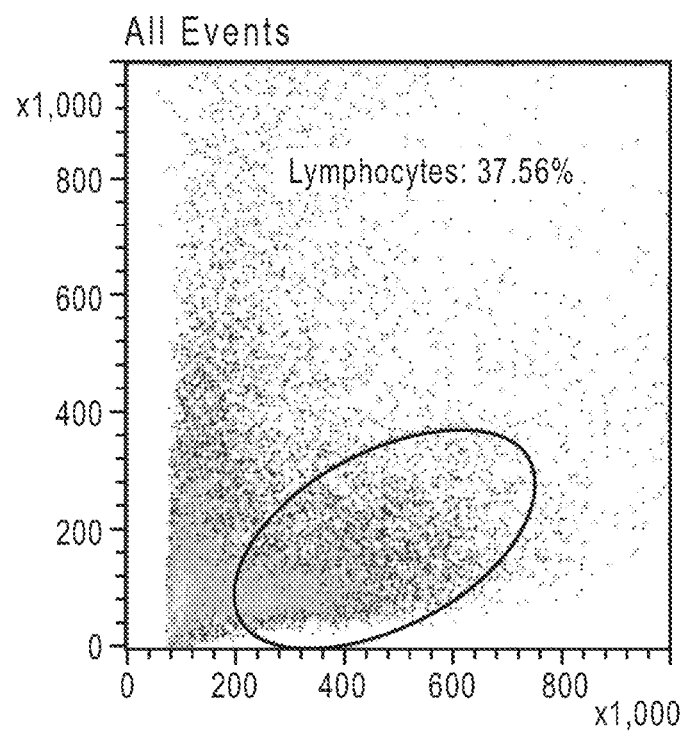
Figure 9B:
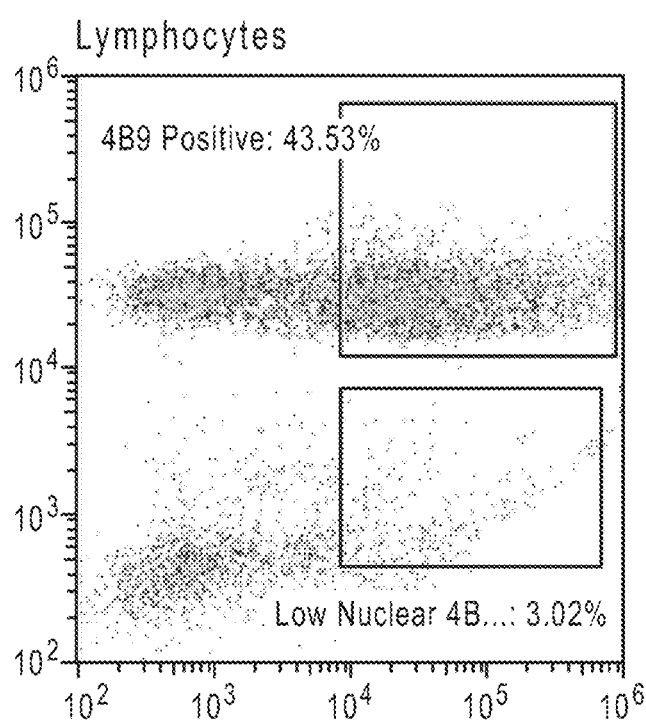

FIGS. 9A-9B: FIG. 9A shows the correlated measurements of FSC (X axis) and BSC (Y axis) using light scattering properties of the cell to differentiate cell types of 4B9 positive cell fraction sorted by fluorescence activated cell sorting (FACS). FIG. 9B shows the FACS sub-gate of lymphocytes from 4B9 positive cell fraction. The X axis represents AF 488 staining and the Y axis represents DC-Ruby staining.

Figure 10A:
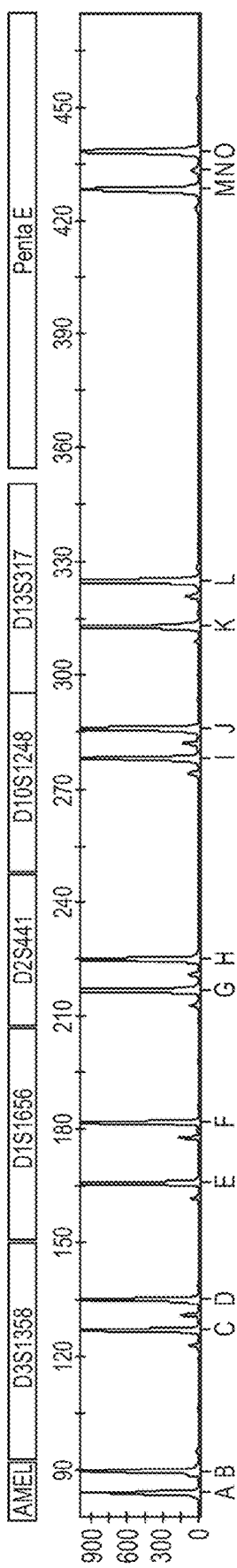
Figure 10B:
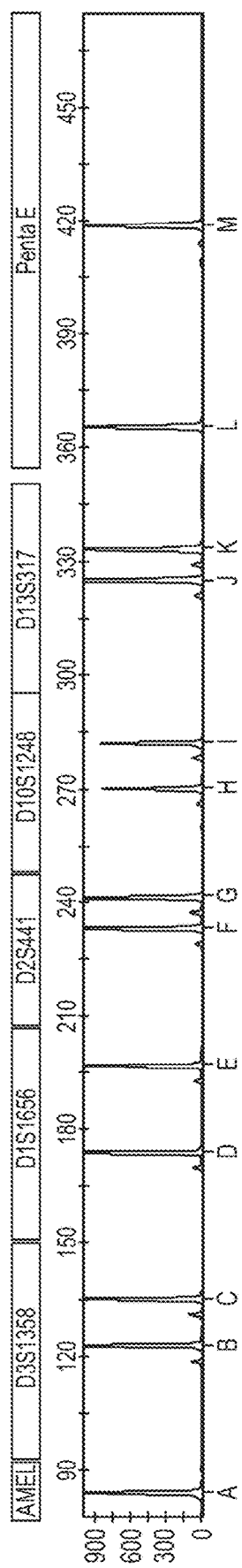
Figure 10C:
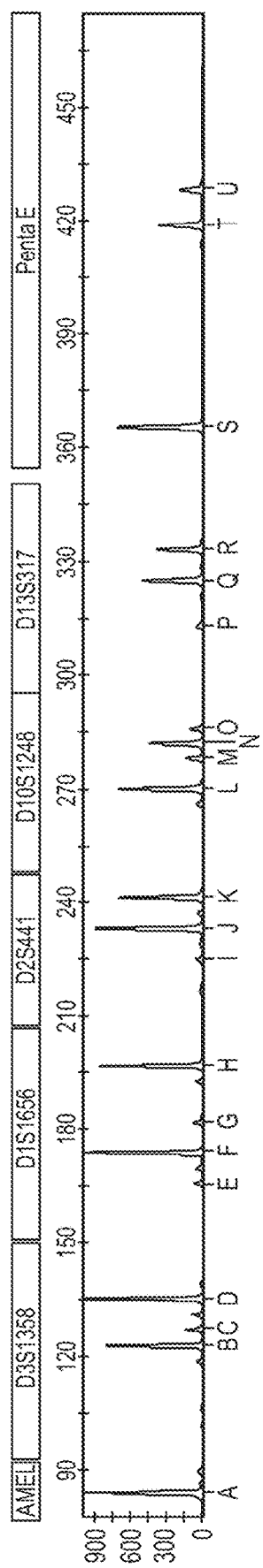

FIGS. 10A-C: Capillary electrophoresis of STR products from spiked mixture of fetal liver cells in male blood. FIG. 10A shows FAM analysis of purified male genomic DNA. FIG. 10B shows FAM analysis of purified DNA from female fetal liver cells. FIG. 10C shows FAM analysis of FACS sorted 4B9 positive fraction after enrichment.

Figure 11A:
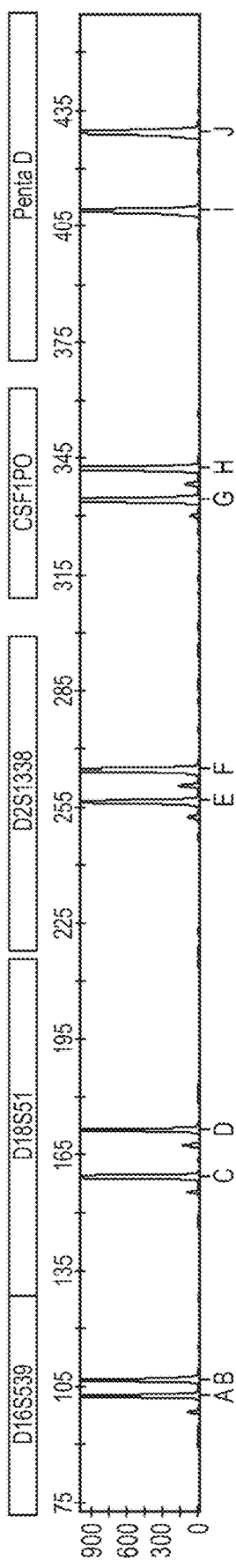
Figure 11B:
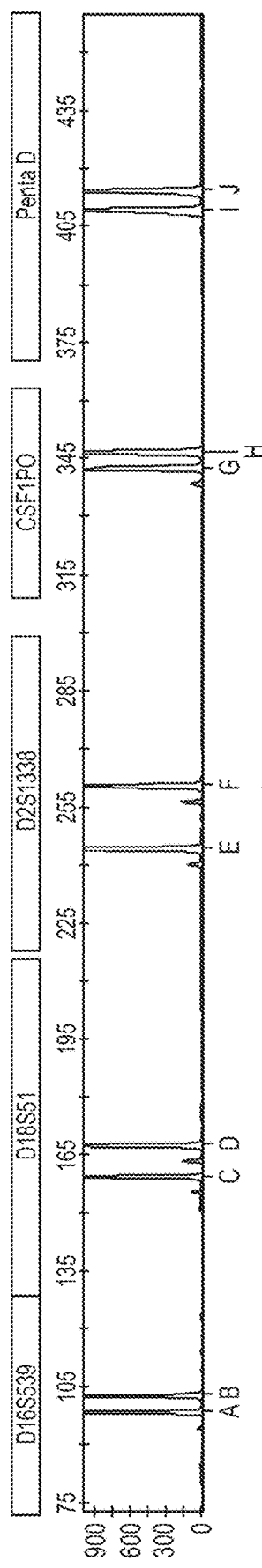
Figure 11C:
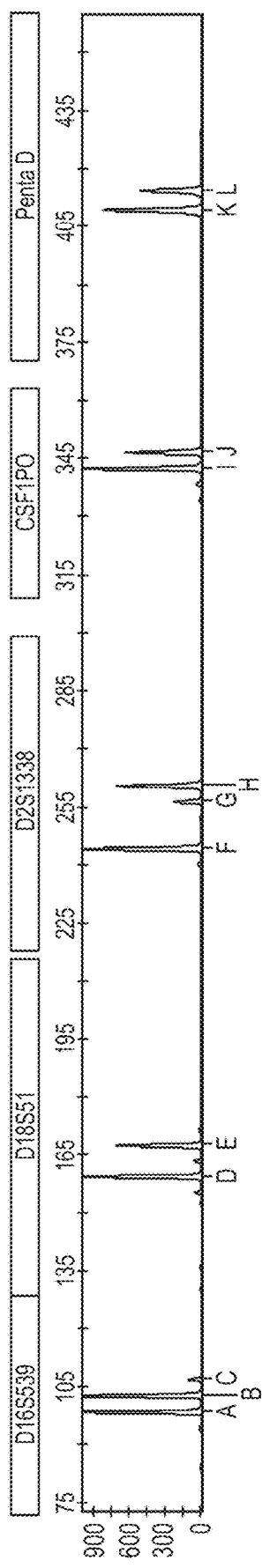

FIGS. 11A-C: Capillary electrophoresis of STR products from spiked mixture of fetal liver cells in male blood. FIG. 11A shows VIC analysis of purified male genomic DNA. FIG. 11B shows VIC analysis of purified DNA from female fetal liver cells. FIG. 11C shows VIC analysis of FACS sorted 4B9 positive fraction after enrichment.

Figure 12A:
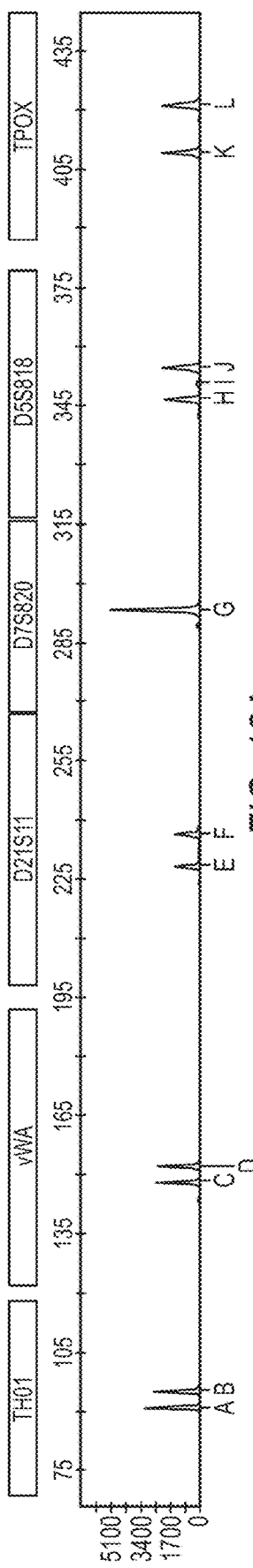
Figure 12B:
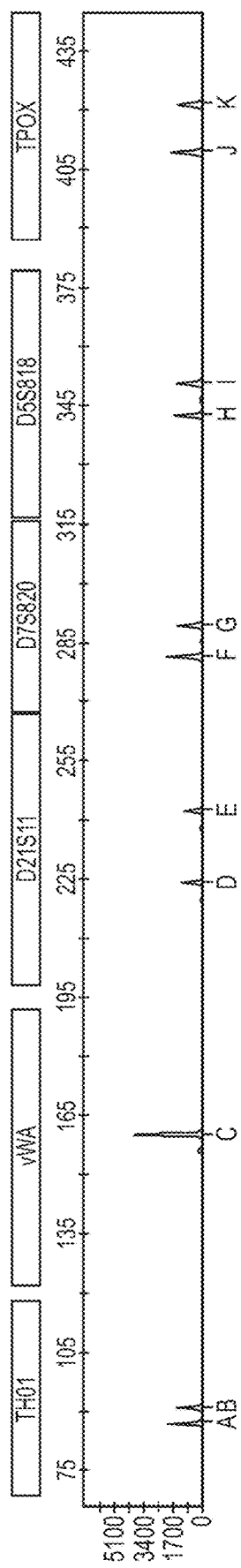
Figure 12C:
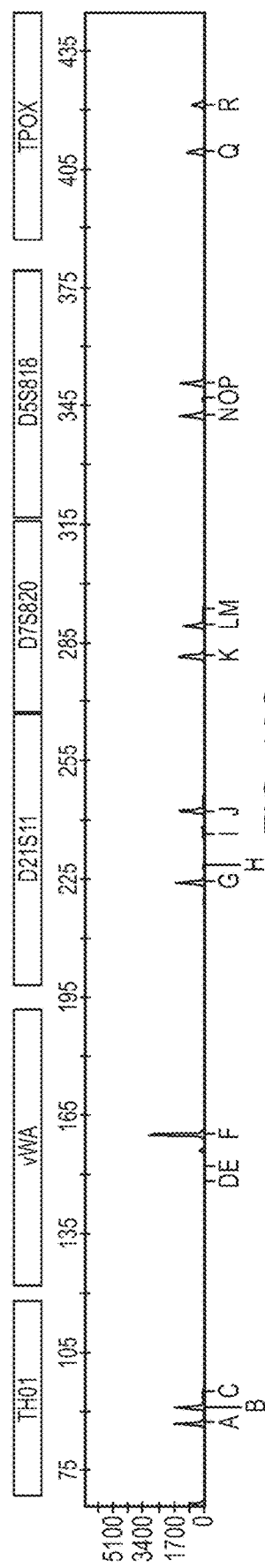

FIGS. 12A-C: Capillary electrophoresis of STR products from spiked mixture of fetal liver cells in male blood. FIG. 12A shows NED analysis of purified male genomic DNA. FIG. 12B shows NED analysis of purified DNA from female fetal liver cells. FIG. 12C shows NED analysis of FACS sorted 4B9 positive fraction after enrichment.

Figure 13A:
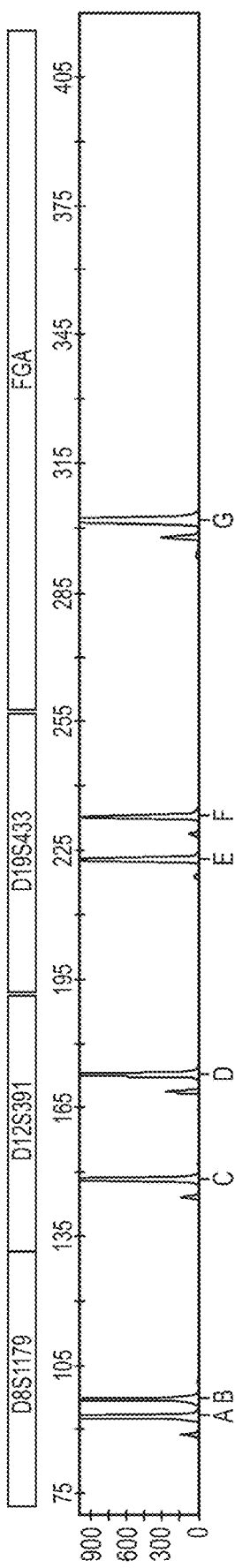
Figure 13B:
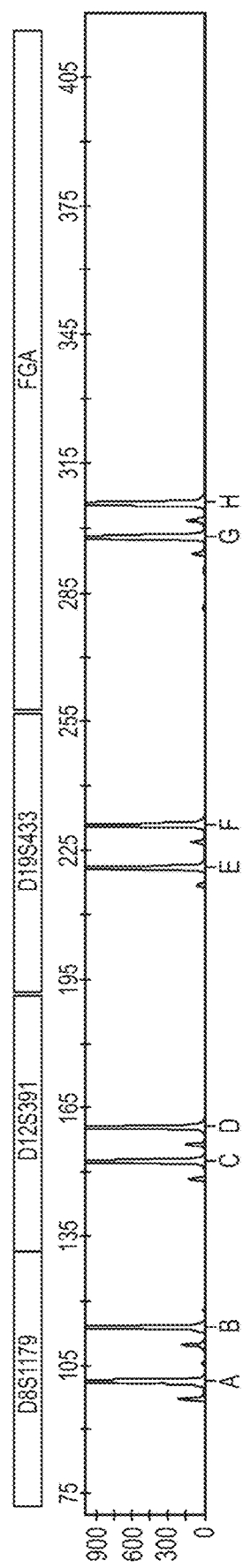
Figure 13C:
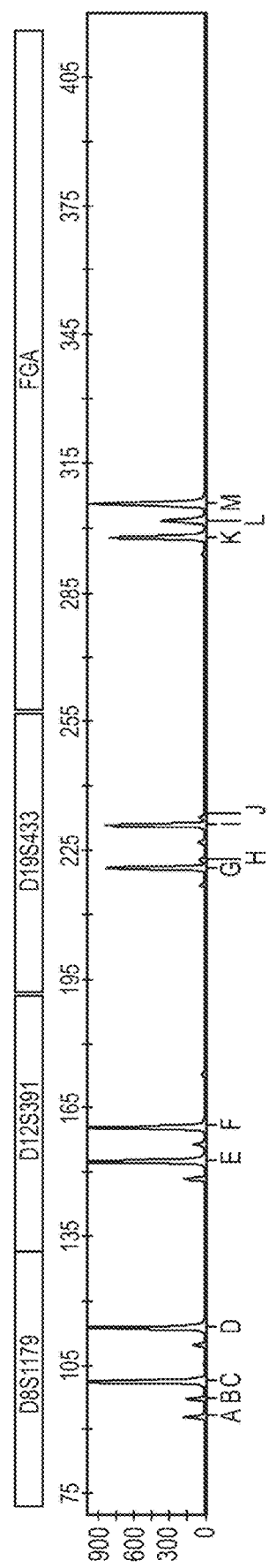

FIGS. 13A-C: Capillary electrophoresis of STR products from spiked mixture of fetal liver cells in male blood. FIG. 13A shows PET analysis of purified male genomic DNA. FIG. 13B shows PET analysis of purified DNA from female fetal liver cells. FIG. 13C shows PET analysis of FACS sorted 4B9 positive fraction after enrichment.

Figure 14:
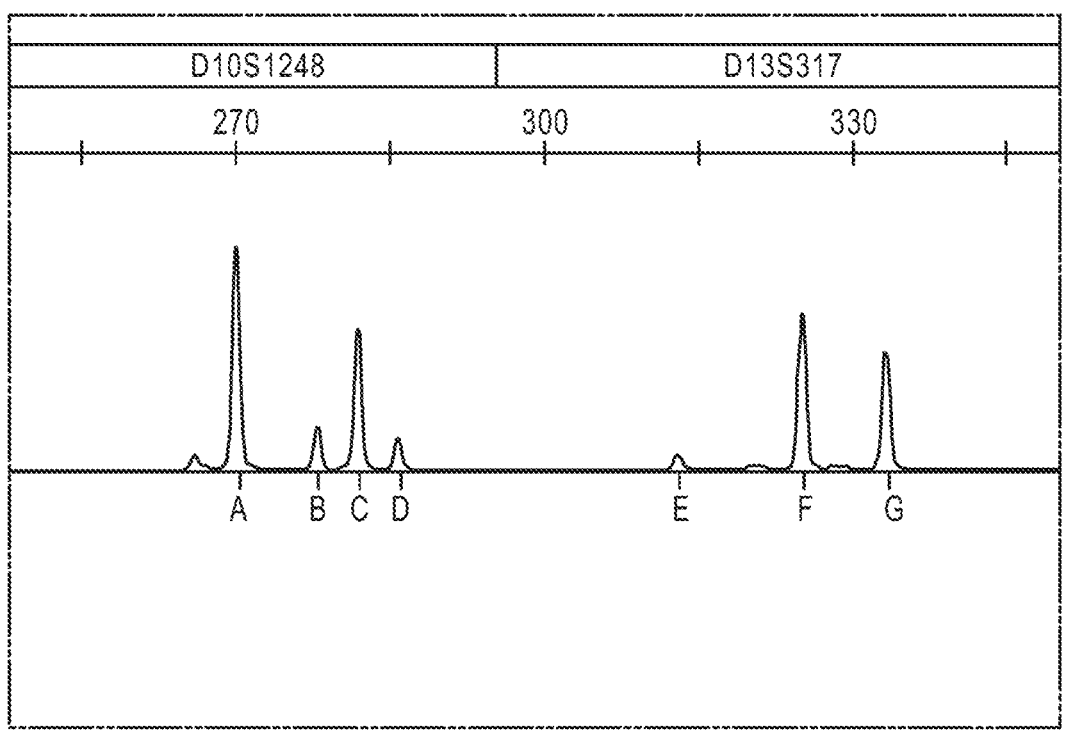

FIG. 14: Isolated capillary electrophoresis of FAM STR products from 4B9 positive fraction of spiked mixture of fetal liver cells in male blood: Panels shows two major contributor alleles (A, C) and two minor alleles (B, D) of D10S1248 marker; and two major contributor alleles (F, G) and one minor allele (E) of D13S317 marker.

Figure 15A:
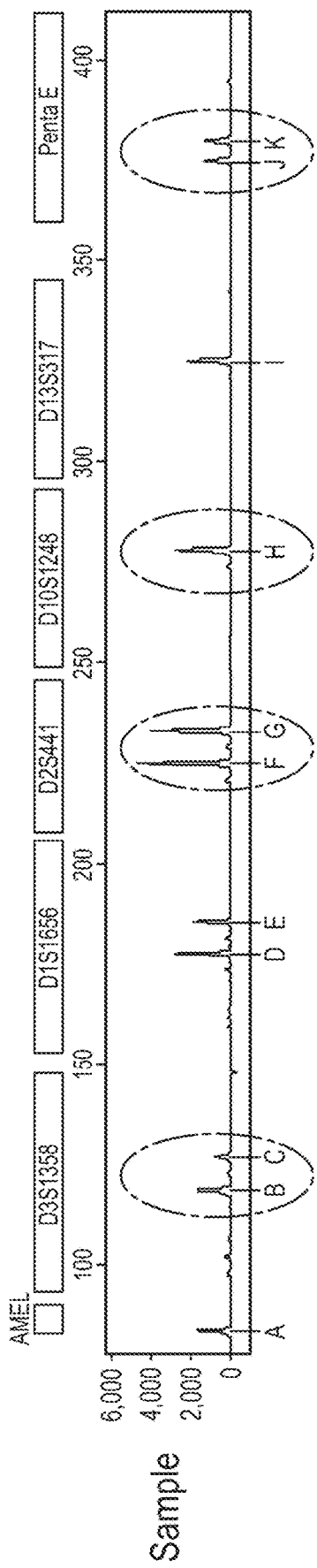
Figure 15B:
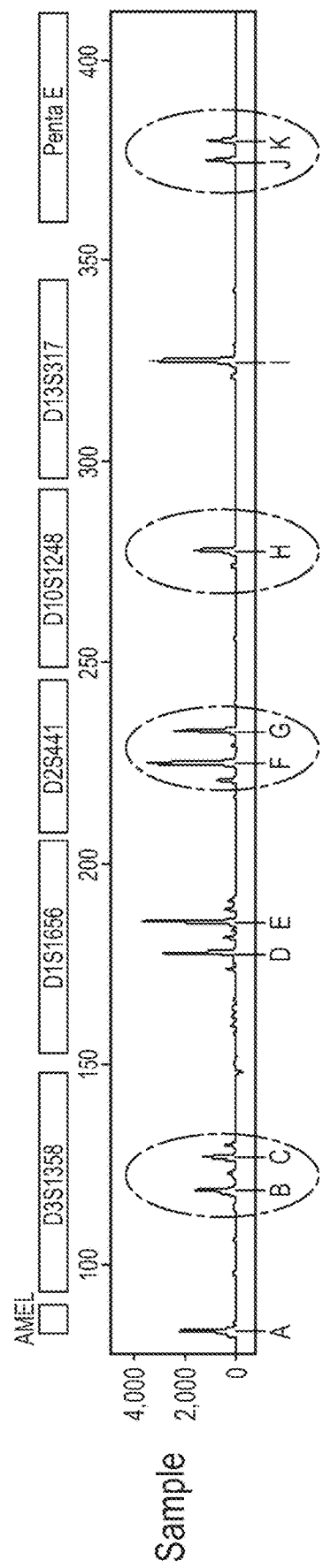
Figure 15C:
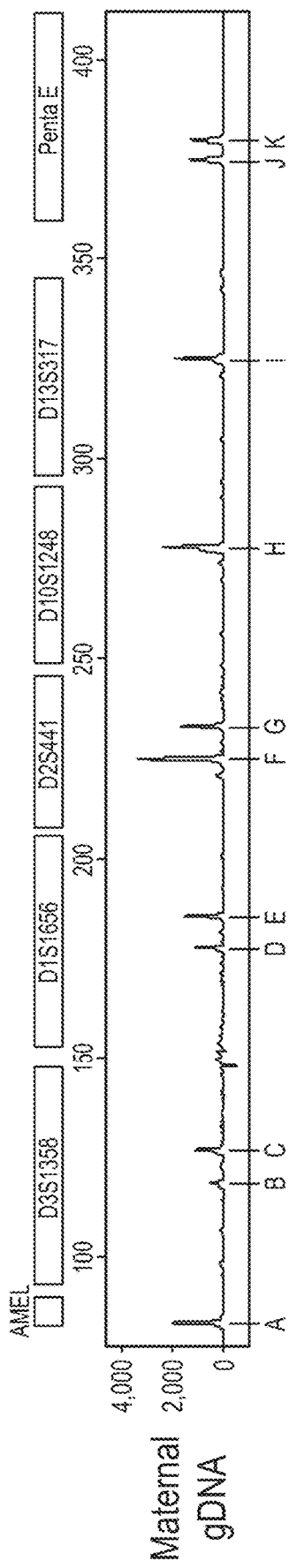
Figure 15D:
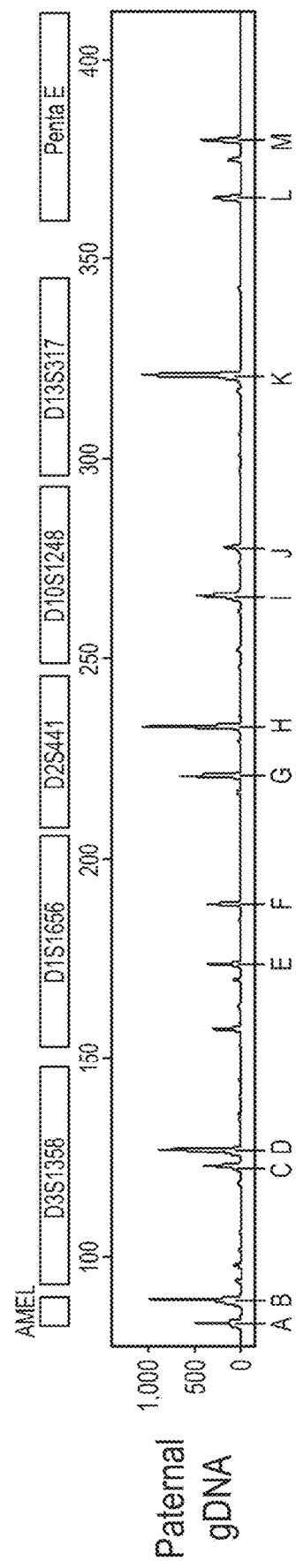

FIGS. 15A-D: Capillary electrophoresis of STR products from 4B9 cells isolated from peripheral blood of woman 7 weeks pregnant with a male fetus. FIG. 15A and FIG. 15B each show FAM analysis of sample cells. FIG. 15C shows FAM analysis of maternal genomic DNA. FIG. 15D shows FAM analysis of paternal genomic DNA. Circles formed by alternating dashes and dots identify alleles found in both the maternal and paternal profiles.

Figure 16A:
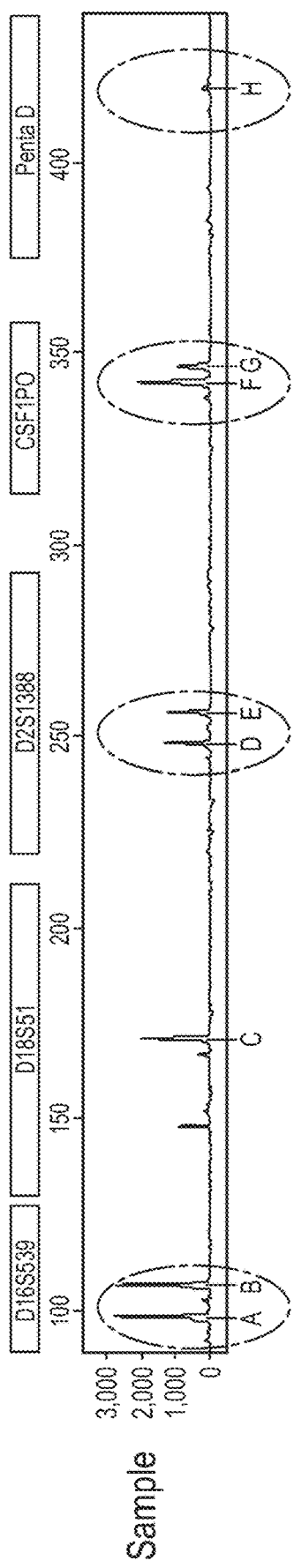
Figure 16B:
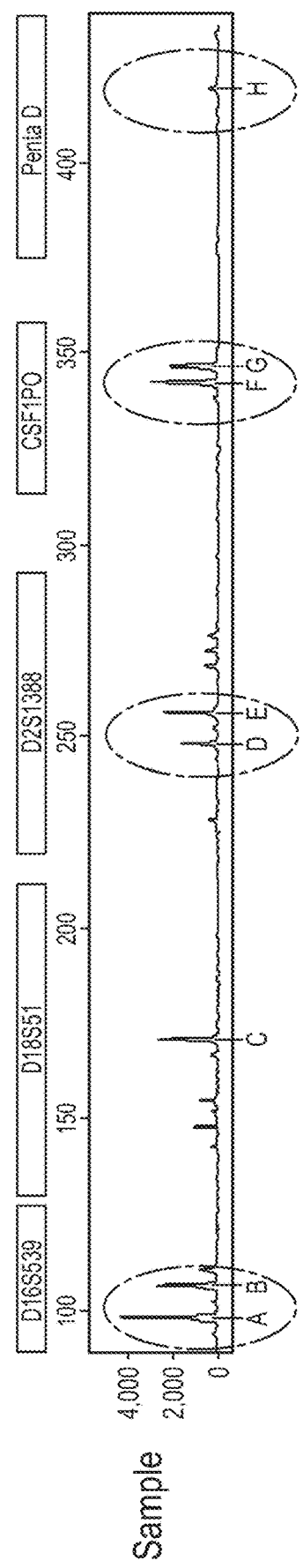
Figure 16C:
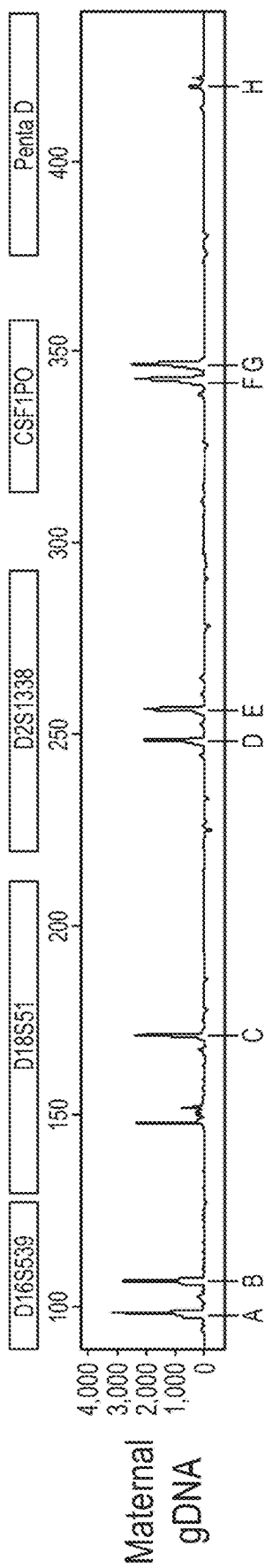
Figure 16D:
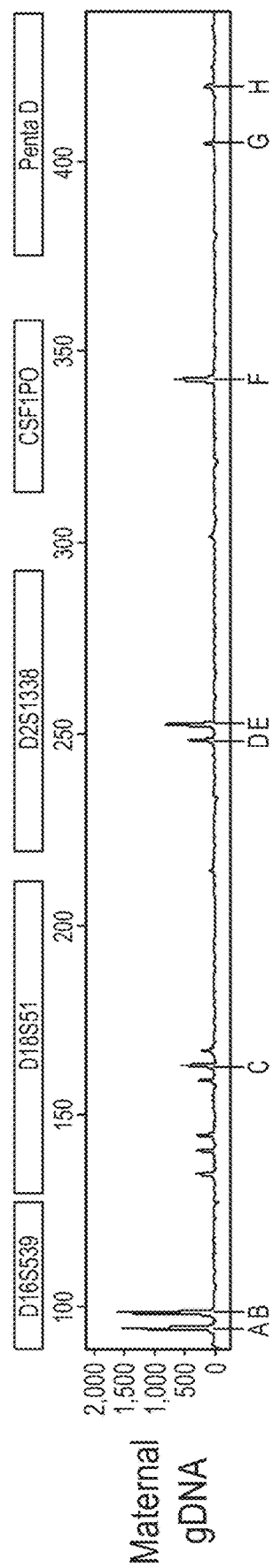

FIGS. 16A-D: Capillary electrophoresis of STR products from 4B9 cells isolated from peripheral blood of woman 7 weeks pregnant with a male fetus. FIG. 16A and FIG. 16B each show VIC analysis of sample cells. FIG. 16C shows VIC analysis of maternal genomic DNA. FIG. 16D shows VIC analysis of paternal genomic DNA. Circles formed by alternating dashes and dots identify alleles found in both the maternal and paternal profiles.

Figure 17A:
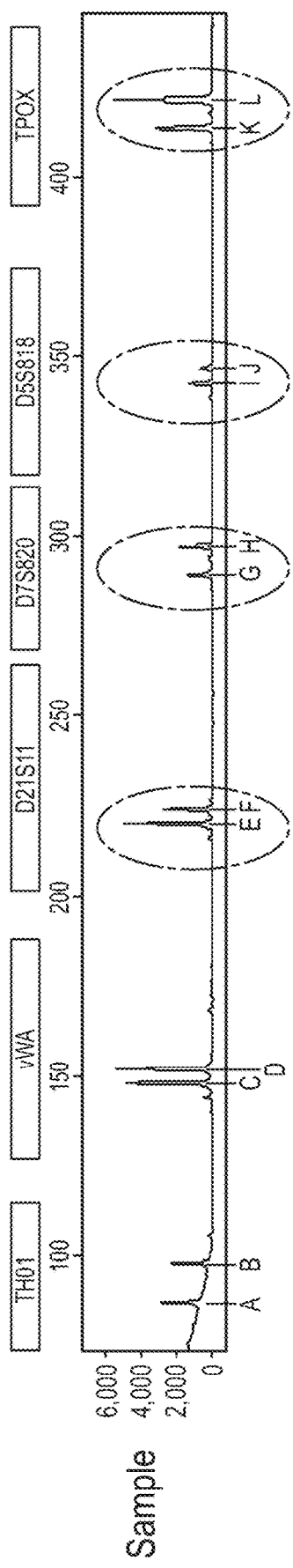
Figure 17B:
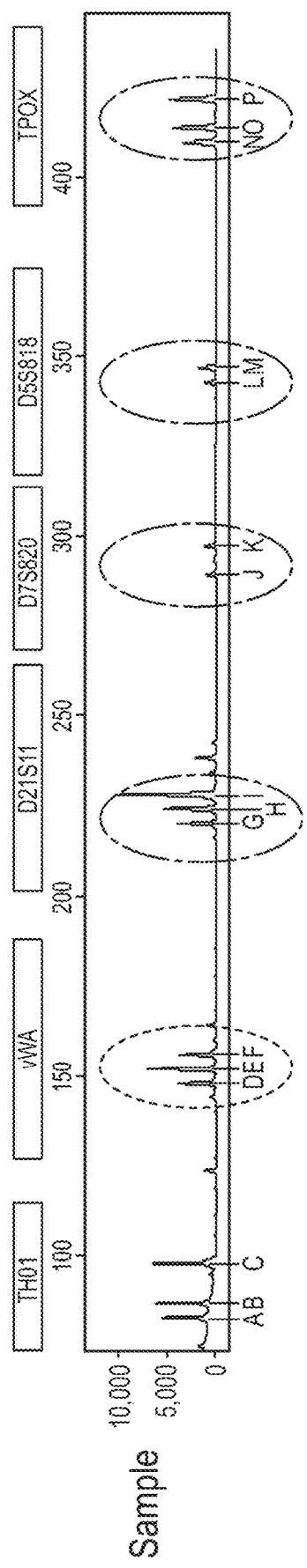
Figure 17C:
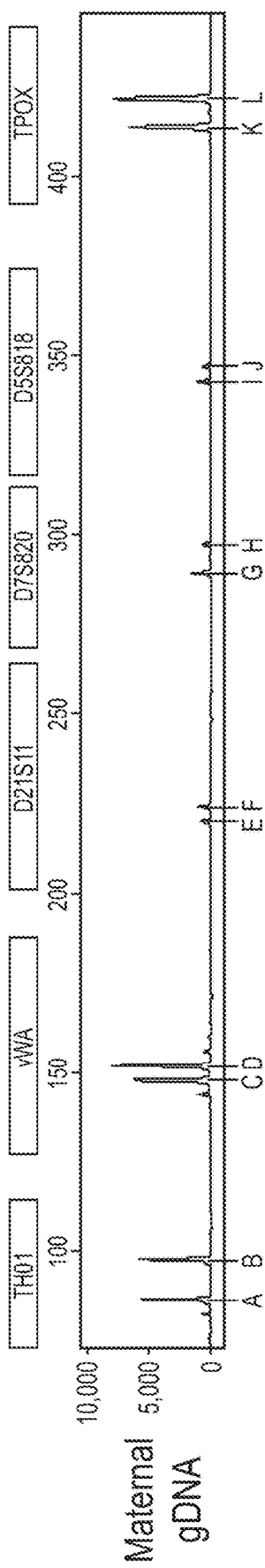
Figure 17D:
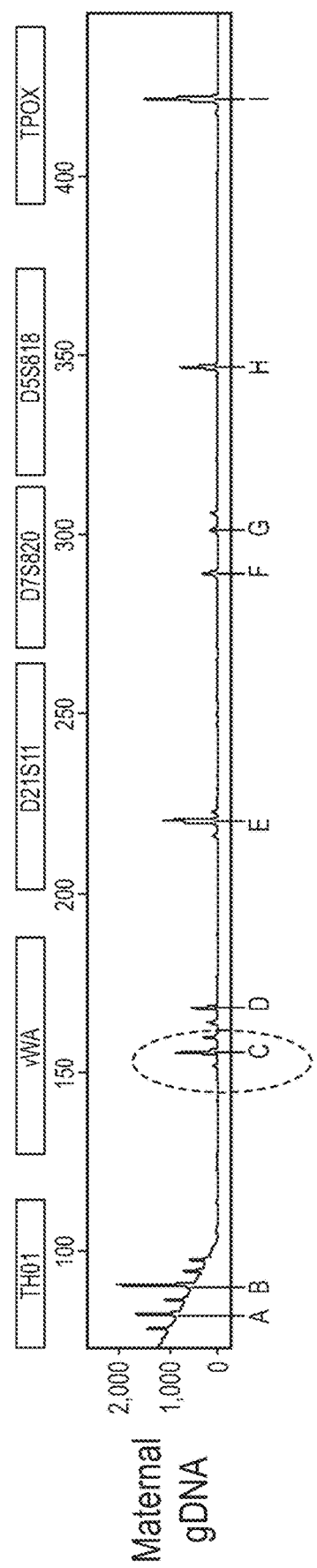

FIGS. 17A-D: Capillary electrophoresis of STR products from 4B9 cells isolated from peripheral blood of woman 7 weeks pregnant with a male fetus. FIG. 17A and FIG. 17B each show NED analysis of sample cells. FIG. 17C shows NED analysis of maternal genomic DNA. FIG. 17D shows NED analysis of paternal genomic DNA. Circles formed by alternating dashes and dots identify alleles found in both the maternal and paternal profiles. Circles formed by even short dashes identify alleles found only in the paternal profile.

Figure 18A:
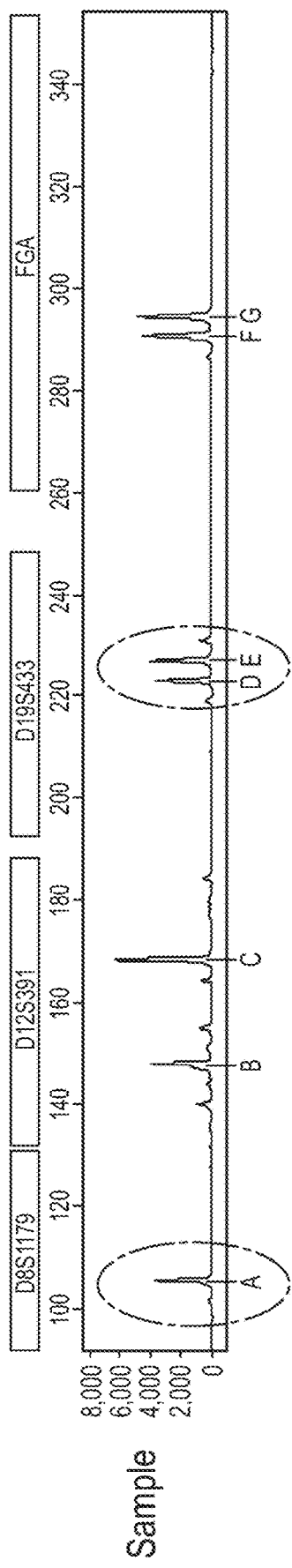
Figure 18B:
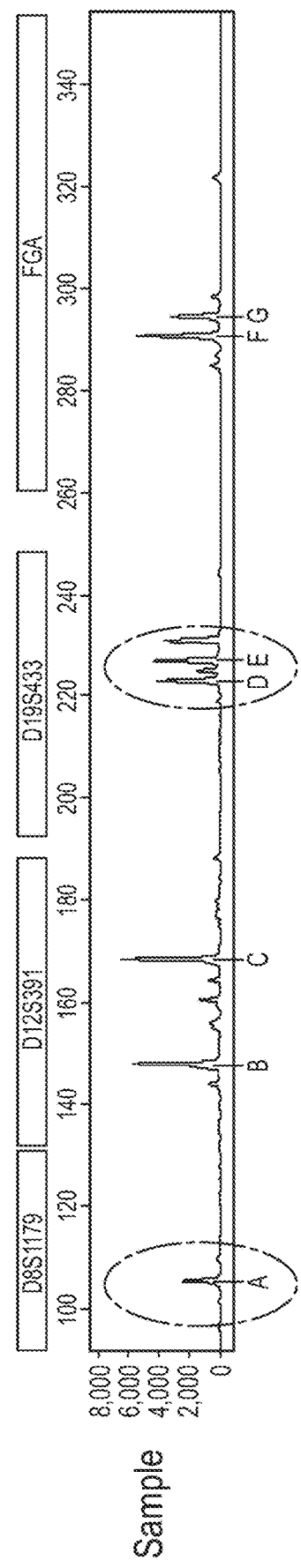
Figure 18C:
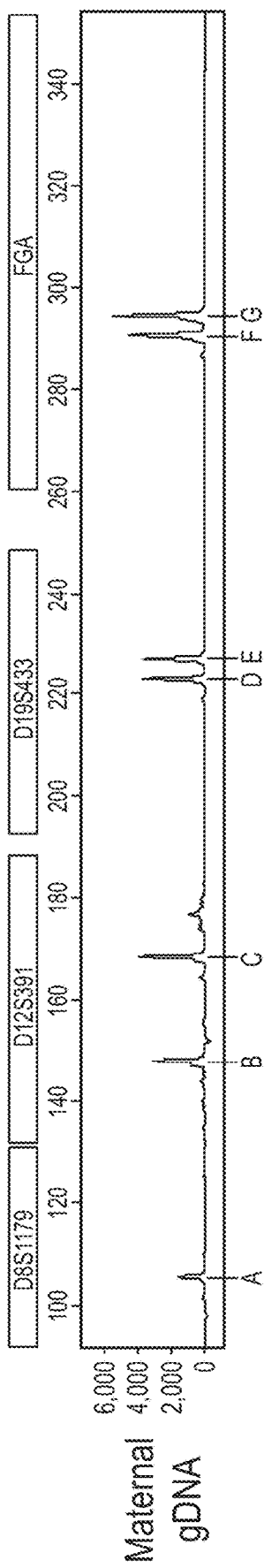
Figure 18D:
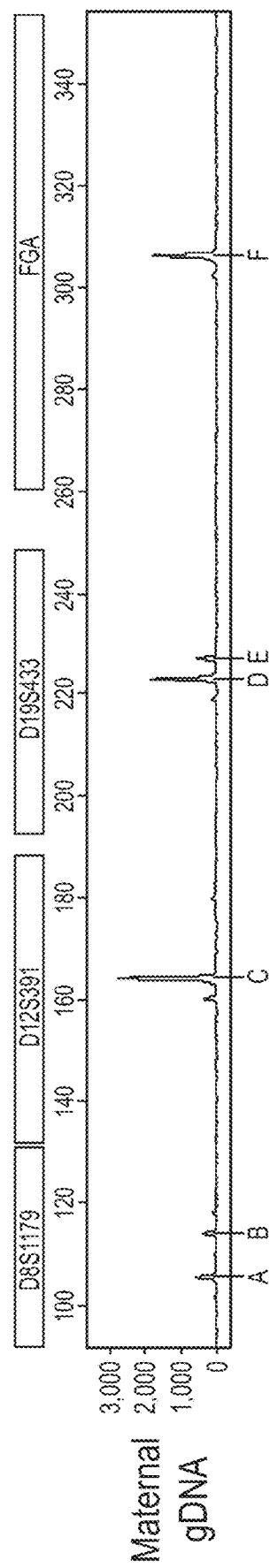

FIGS. 18A-D: Capillary electrophoresis of STR products from 4B9 cells isolated from peripheral blood of woman 7 weeks pregnant with a male fetus. FIG. 18A and FIG. 18B each show PET analysis of sample cells. FIG. 18C shows PET analysis of maternal genomic DNA. FIG. 18D shows PET analysis of paternal genomic DNA. Circles formed by alternating dashes and dots identify alleles found in both the maternal and paternal profiles. Circles formed by even short dashes identify alleles found only in the paternal profile.

FIGS. 19A-C: Capillary electrophoresis of STR products from 4B9 cells isolated from peripheral blood of woman 9 weeks pregnant with a male fetus. FIG. 19A shows FAM analysis of maternal genomic DNA. FIG. 19B shows FAM analysis of sample cells. FIG. 19C shows FAM analysis of paternal genomic DNA. Circles formed by alternating dashes and dots identify alleles found in both the maternal and paternal profiles.

FIGS. 20A-C: Capillary electrophoresis of STR products from 4B9 cells isolated from peripheral blood of woman 9 weeks pregnant with a male fetus. FIG. 20A shows VIC analysis of maternal genomic DNA. FIG. 20B shows VIC analysis of sample cells. FIG. 20C shows VIC analysis of paternal genomic DNA.

Figure 21A:
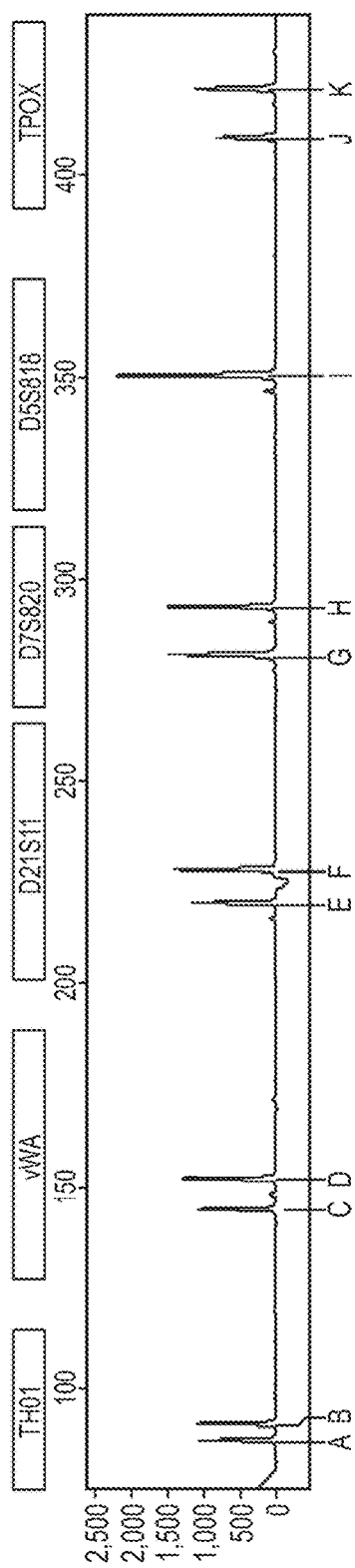
Figure 21B:
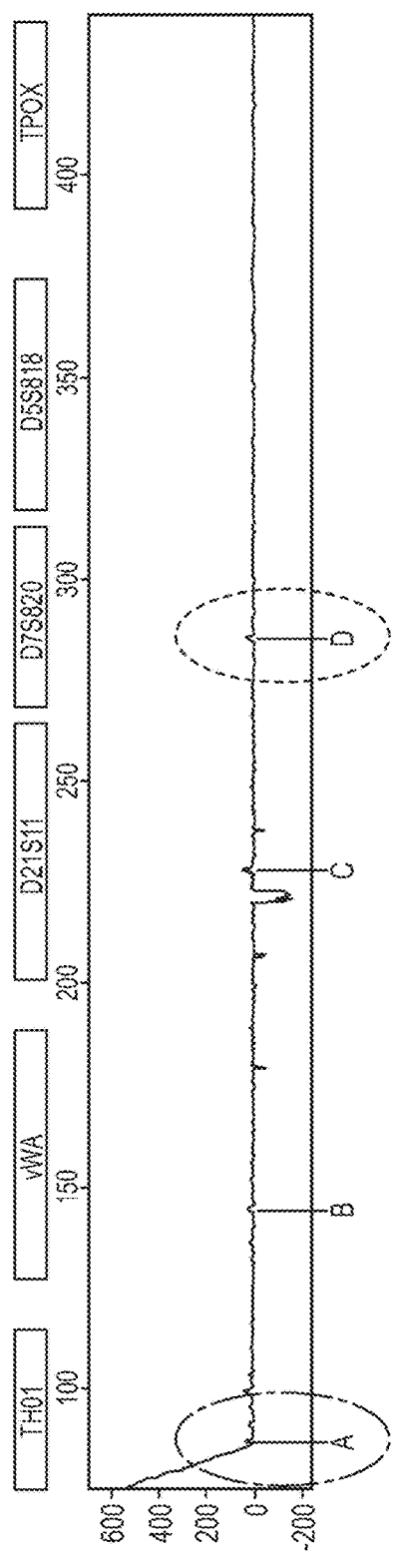
Figure 21C:
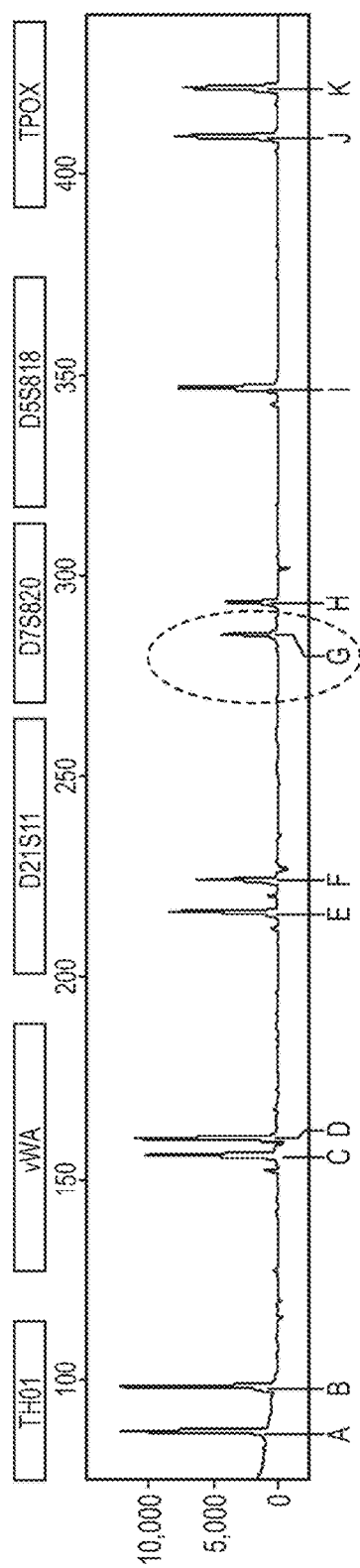

FIGS. 21A-C: Capillary electrophoresis of STR products from 4B9 cells isolated from peripheral blood of woman 9 weeks pregnant with a male fetus. FIG. 21A shows NED analysis of maternal genomic DNA. FIG. 21B shows NED analysis of sample cells. FIG. 21C shows NED analysis of paternal genomic DNA. Circles formed by alternating dashes and dots identify alleles found in both the maternal and paternal profiles. Circles formed by even short dashes identify alleles found only in the paternal profile.

FIGS. 22A-C: Capillary electrophoresis of STR products from 4B9 cells isolated from peripheral blood of woman 9 weeks pregnant with a male fetus. FIG. 22A shows PET analysis of maternal genomic DNA. FIG. 22B shows PET analysis of sample cells. FIG. 22C shows PET analysis of paternal genomic DNA. Circles formed by alternating dashes and dots identify alleles found in both the maternal and paternal profiles. Circles formed by even short dashes identify alleles found only in the paternal profile.

Figure 23A:
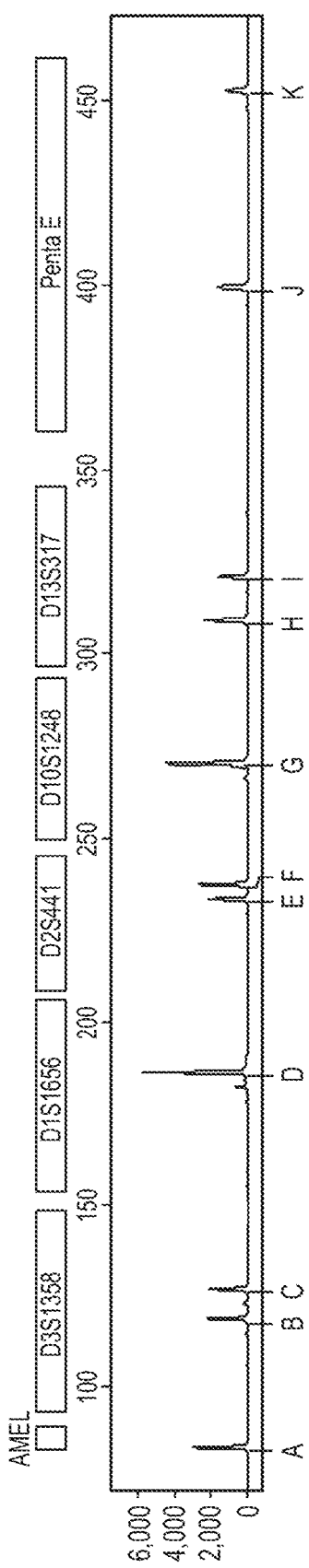
Figure 23B:
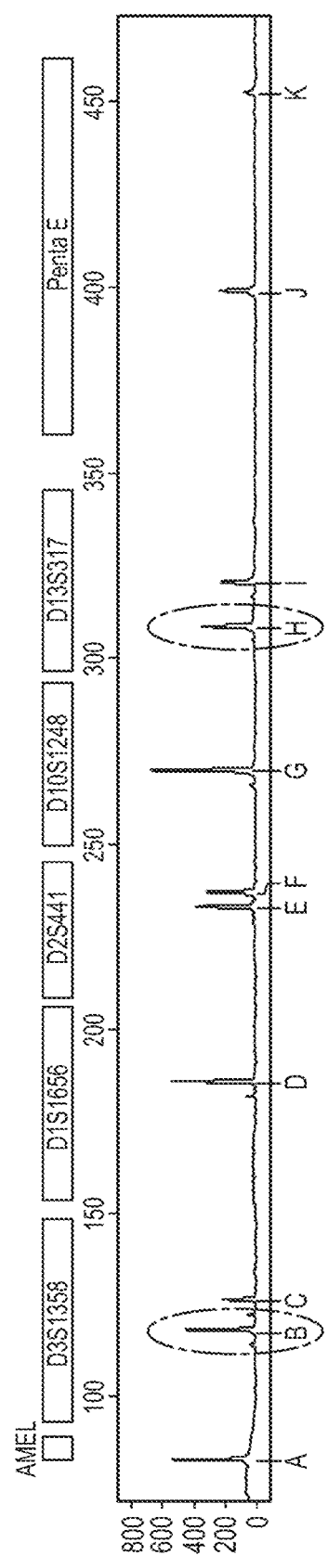
Figure 23C:
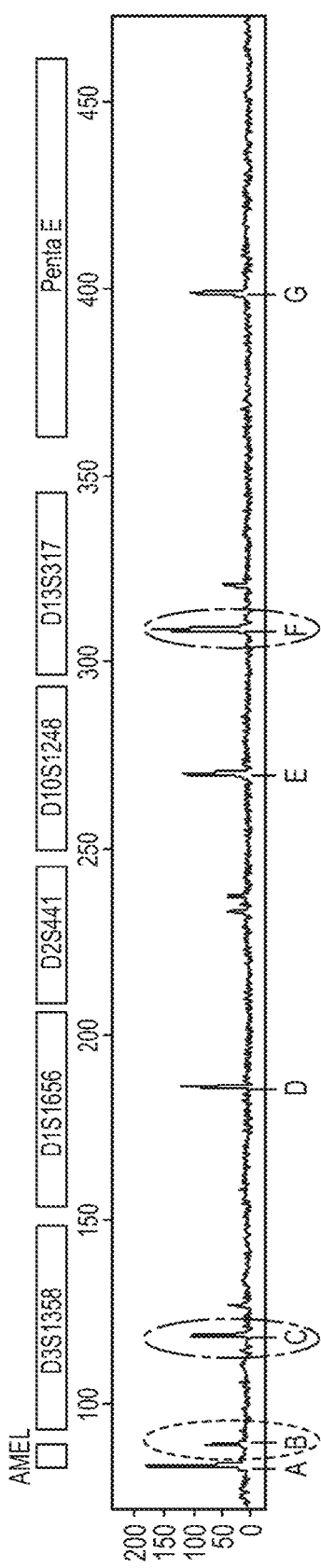
Figure 23D:
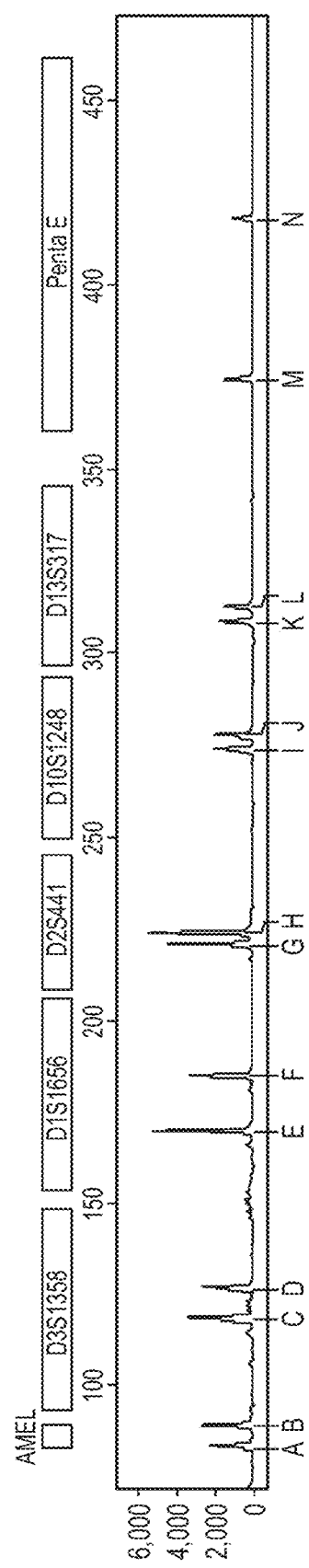

FIGS. 23A-D: Capillary electrophoresis of STR products from 4B9 cells isolated from peripheral blood of woman 12 weeks pregnant with a male fetus. FIG. 23A shows FAM analysis of maternal genomic DNA. FIG. 23B and FIG. 23C each show FAM analysis of sample cells. FIG. 23D shows FAM analysis of paternal genomic DNA. Circles formed by alternating dashes and dots identify alleles found in both the maternal and paternal profiles. Circles formed by even short dashes identify alleles found only in the paternal profile.

Figure 24A:
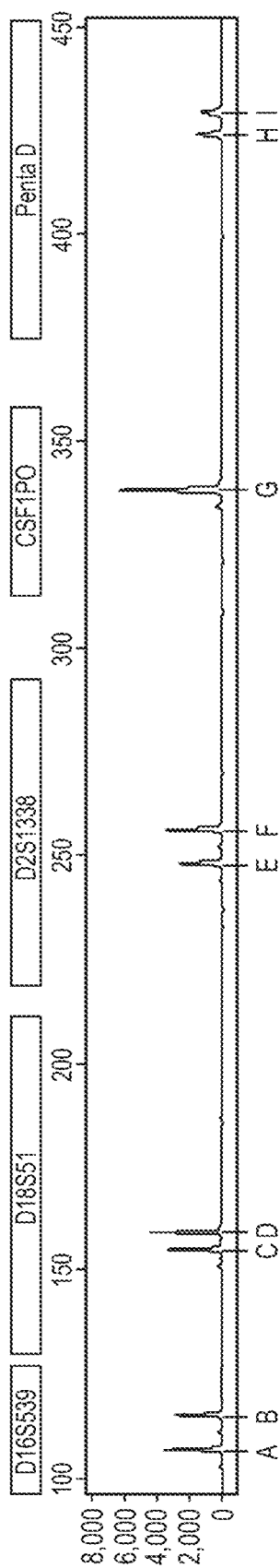
Figure 24B:
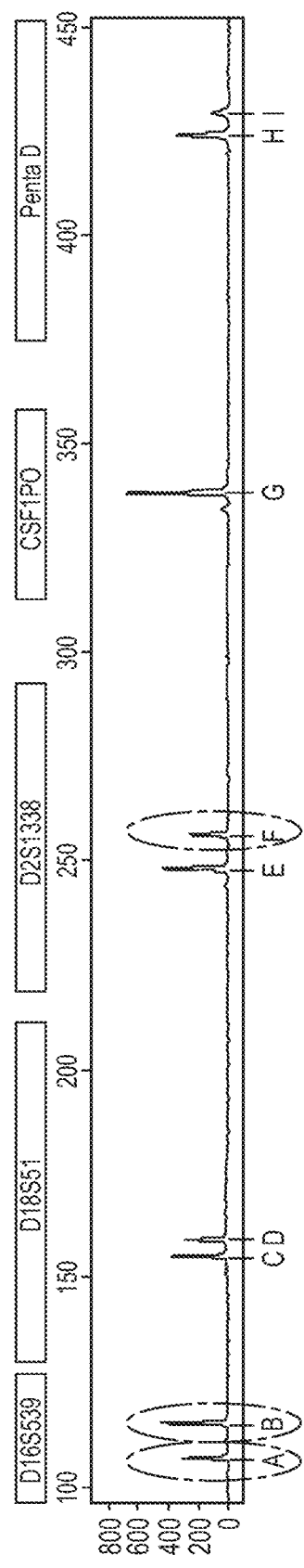
Figure 24C:
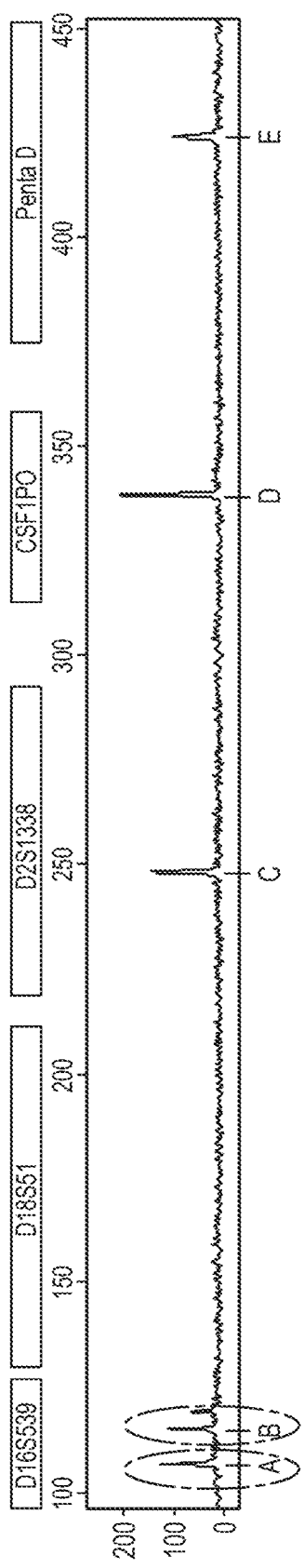
Figure 24D:
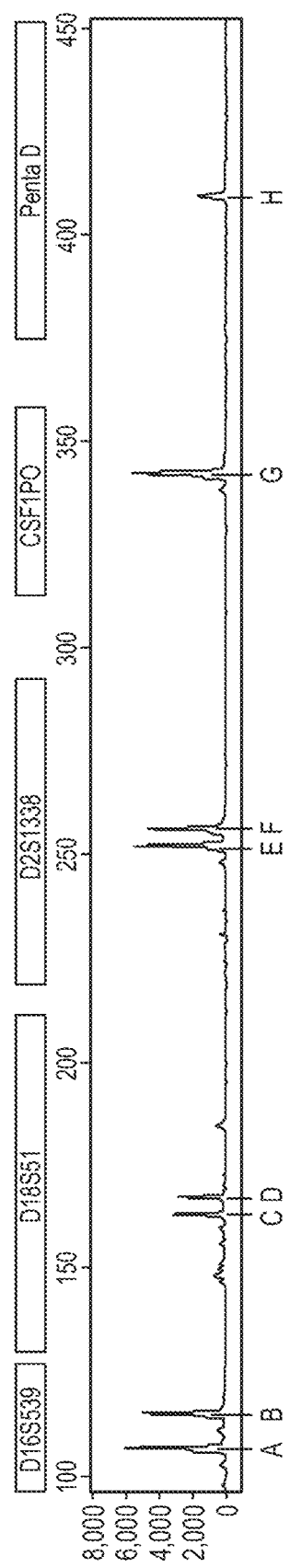

FIGS. 24A-D: Capillary electrophoresis of STR products from 4B9 cells isolated from peripheral blood of woman 12 weeks pregnant with a male fetus. FIG. 24A shows VIC analysis of maternal genomic DNA. FIG. 24B and FIG. 24C each show VIC analysis of sample cells. FIG. 24D shows VIC analysis of paternal genomic DNA. Circles formed by alternating dashes and dots identify alleles found in both the maternal and paternal profiles.

Figure 25A:
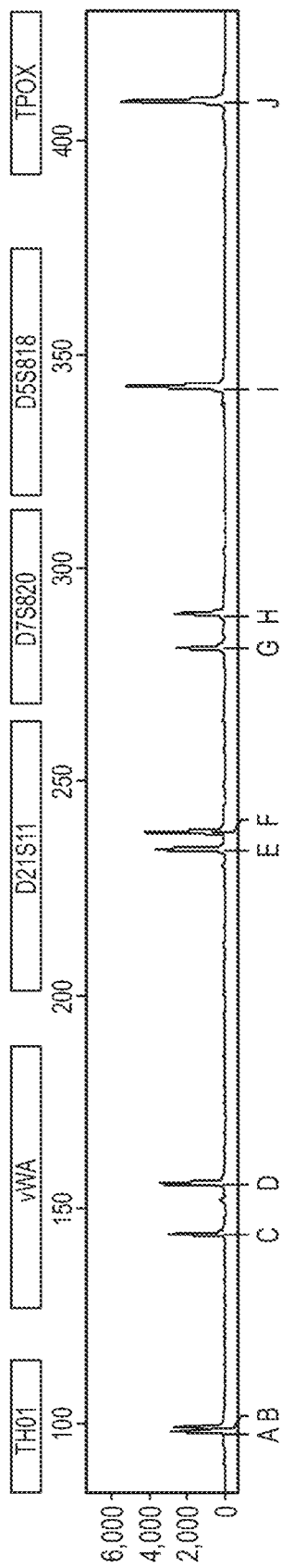
Figure 25B:
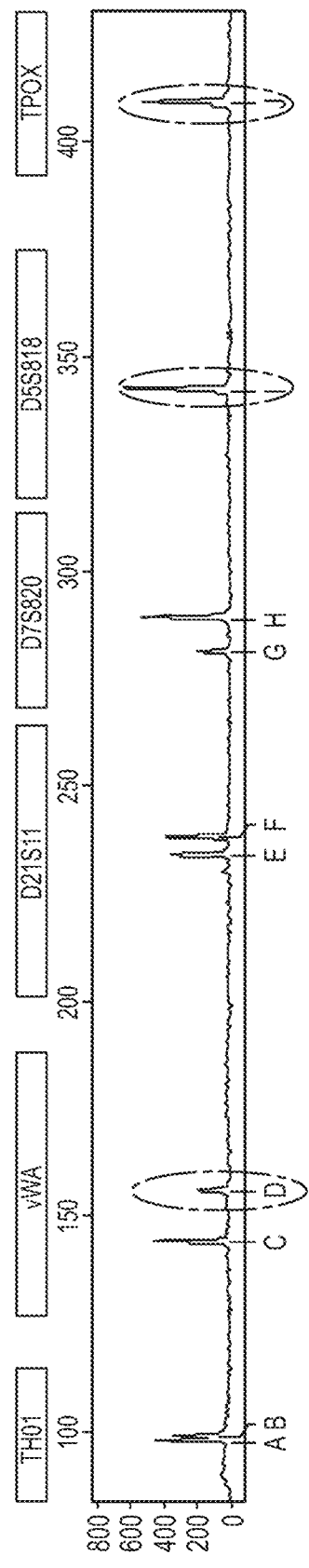
Figure 25C:
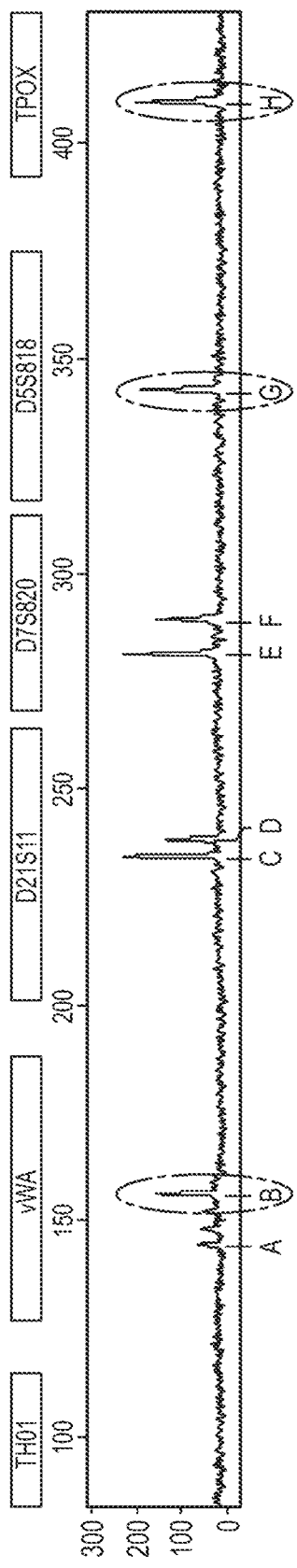
Figure 25D:
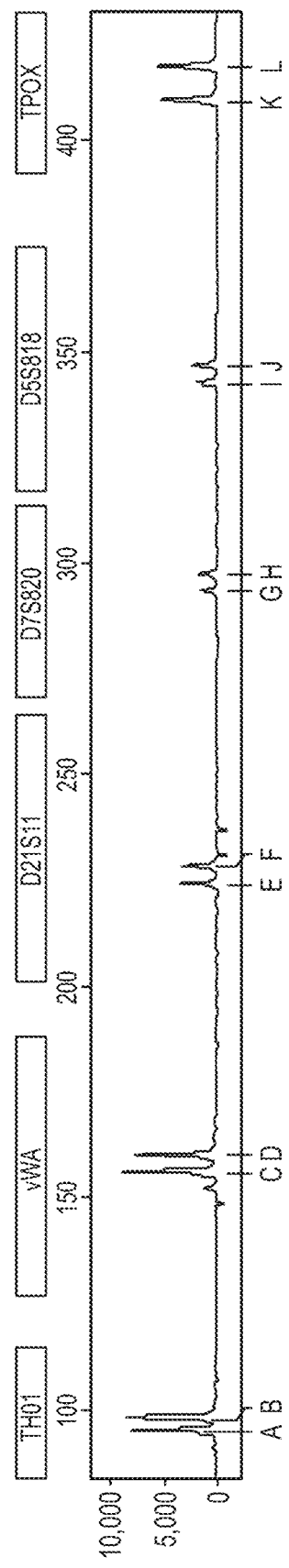

FIGS. 25A-D: Capillary electrophoresis of STR products from 4B9 cells isolated from peripheral blood of woman 12 weeks pregnant with a male fetus. FIG. 25A shows NED analysis of maternal genomic DNA. FIG. 25B and FIG. 25C each show NED analysis of sample cells. FIG. 25D shows NED analysis of paternal genomic DNA. Circles formed by alternating dashes and dots identify alleles found in both the maternal and paternal profiles.

Figure 26A:
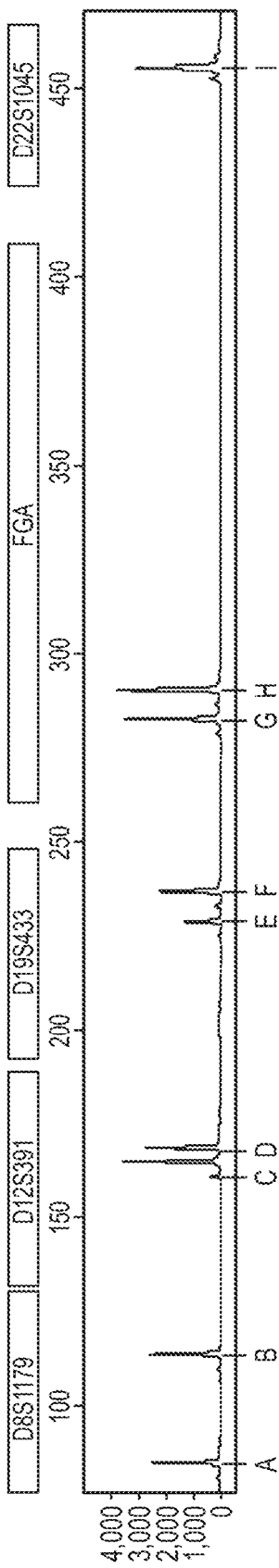
Figure 26B:
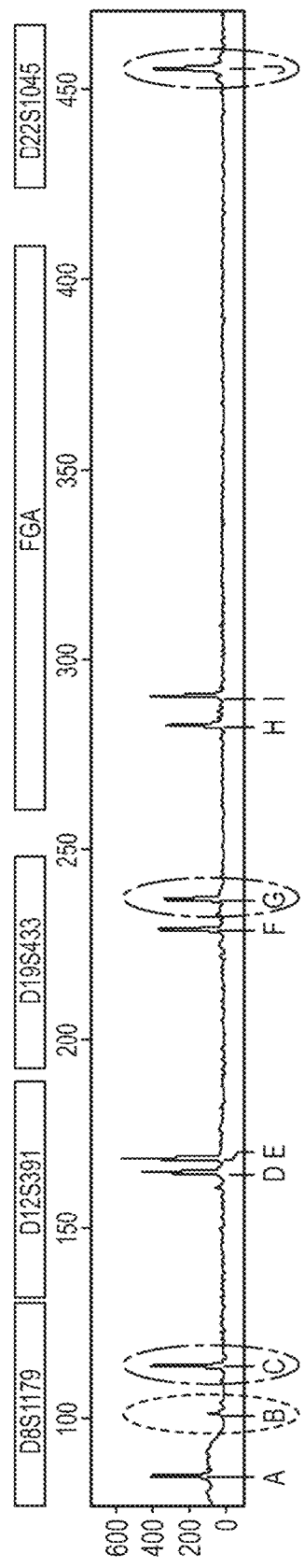
Figure 26C:
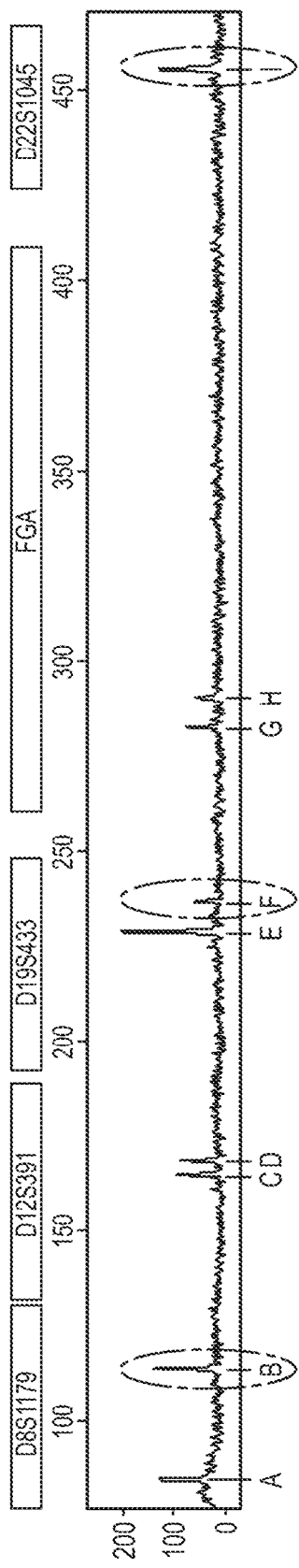
Figure 26D:
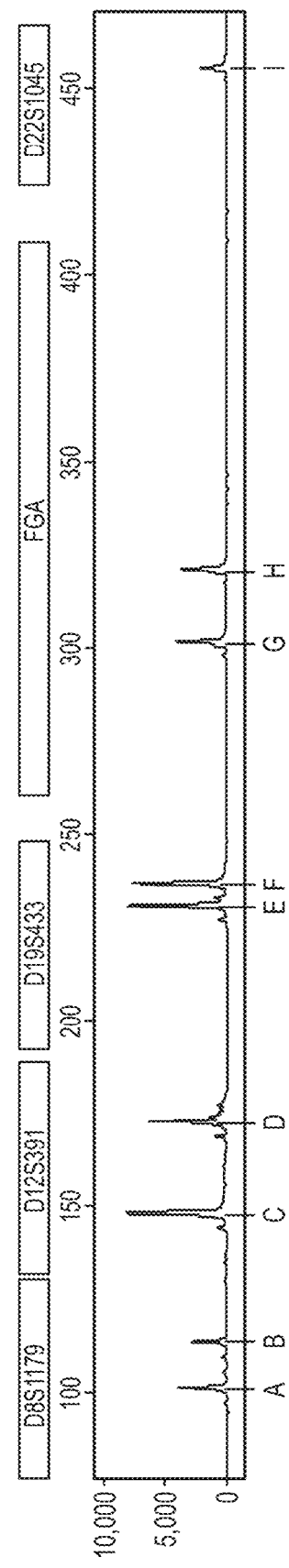

FIGS. 26A-D: Capillary electrophoresis of STR products from 4B9 cells isolated from peripheral blood of woman 12 weeks pregnant with a male fetus. FIG. 26A shows PET analysis of maternal genomic DNA. FIG. 26B and FIG. 26C each show PET analysis of sample cells. FIG. 26D shows PET analysis of paternal genomic DNA. Circles formed by alternating dashes and dots identify alleles found in both the maternal and paternal profiles. Circles formed by even short dashes identify alleles found only in the paternal profile.

Figure 27:
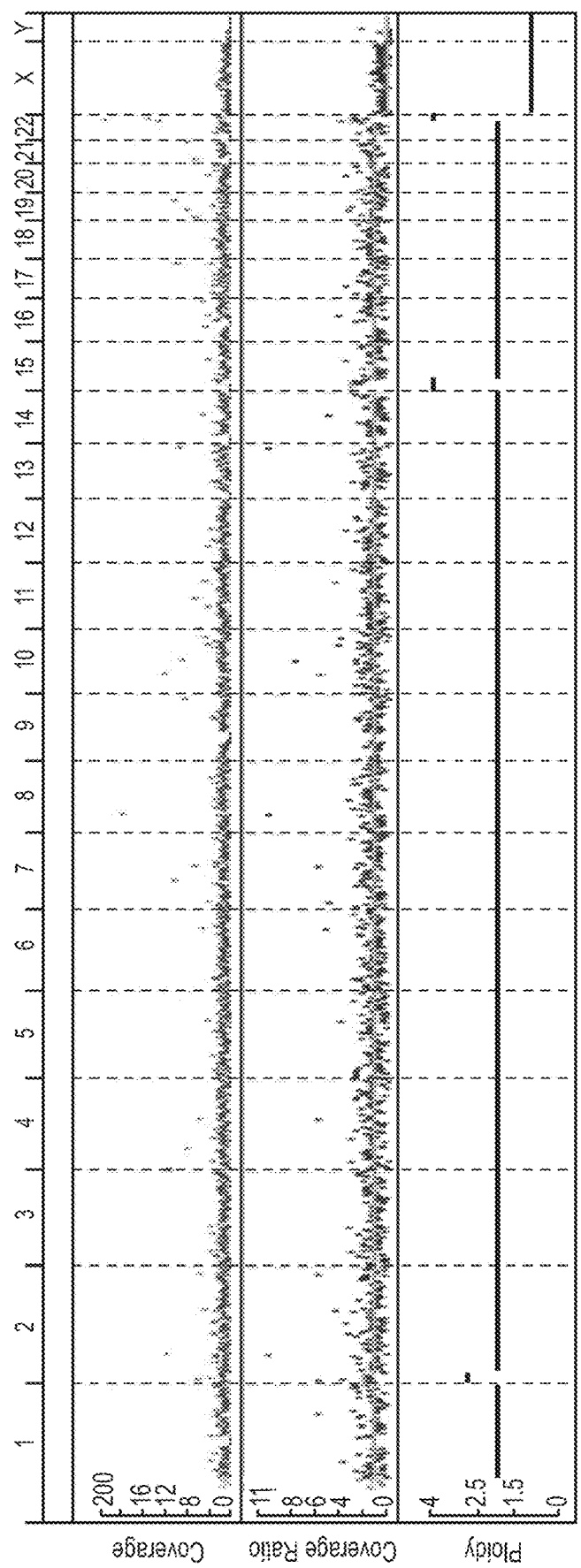

FIG. 27: Whole genome karyogram of a fNRBC isolated from peripheral blood of a woman pregnant with a normal male fetus.

Figure 28:
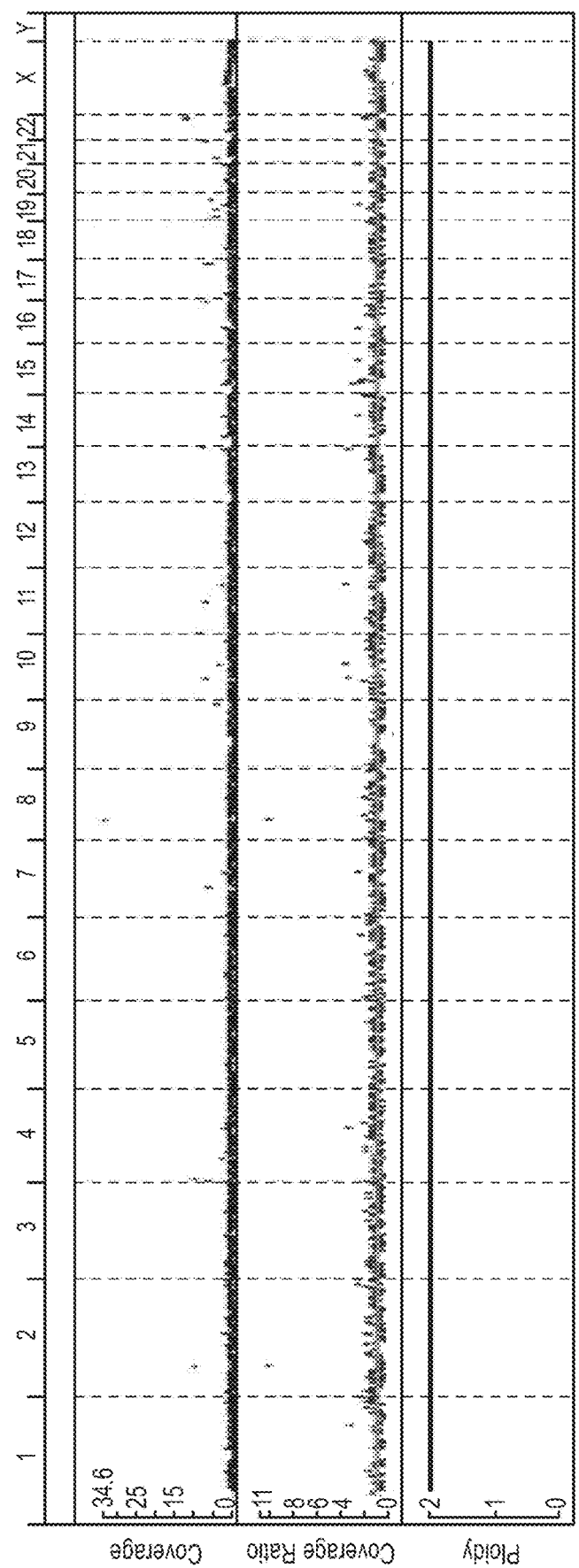

FIG. 28: Whole genome karyogram of a fNRBC isolated from peripheral blood of a woman pregnant with a normal female fetus.

Figure 29:
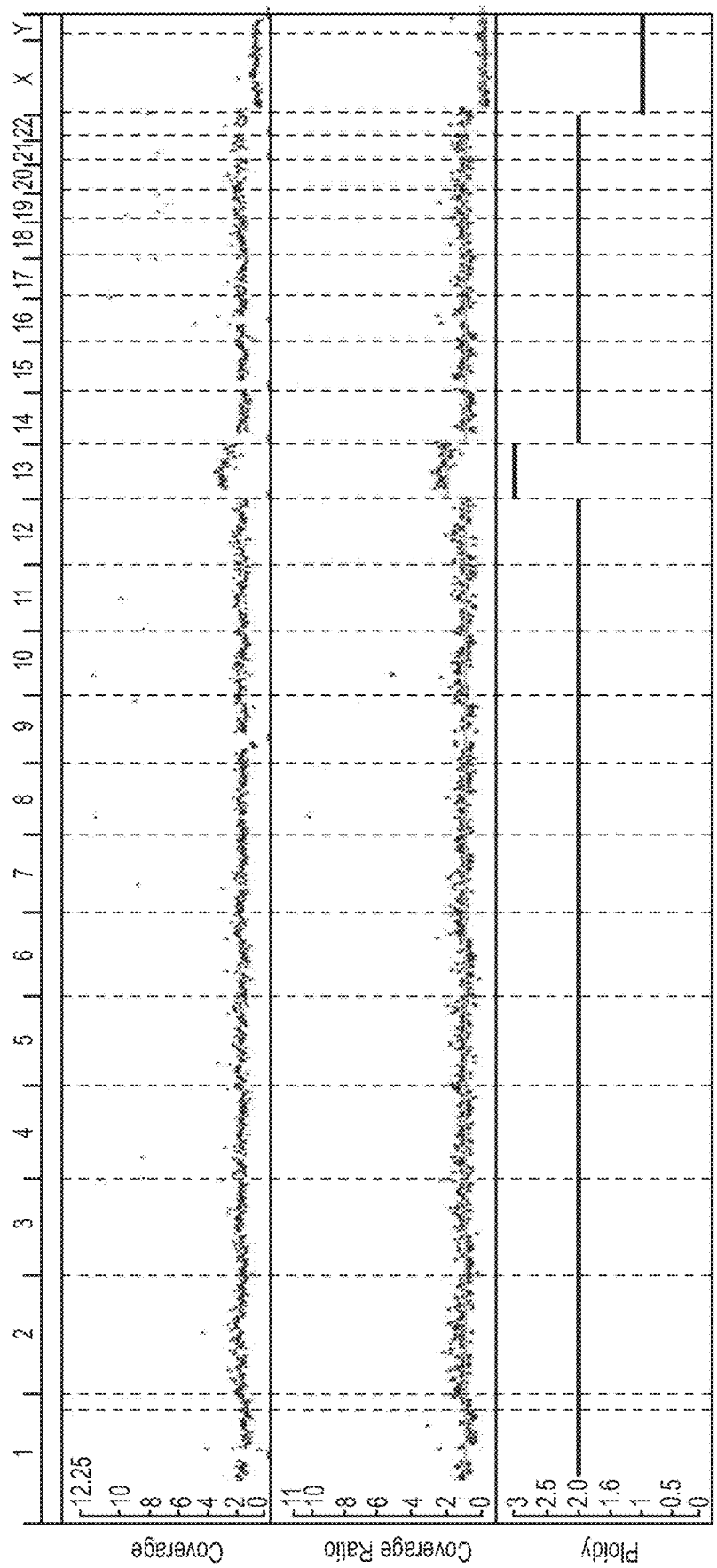

FIG. 29: Whole genome karyogram of a fNRBC isolated from peripheral blood of a woman pregnant with a male fetus having trisomy 13.

Figure 30:
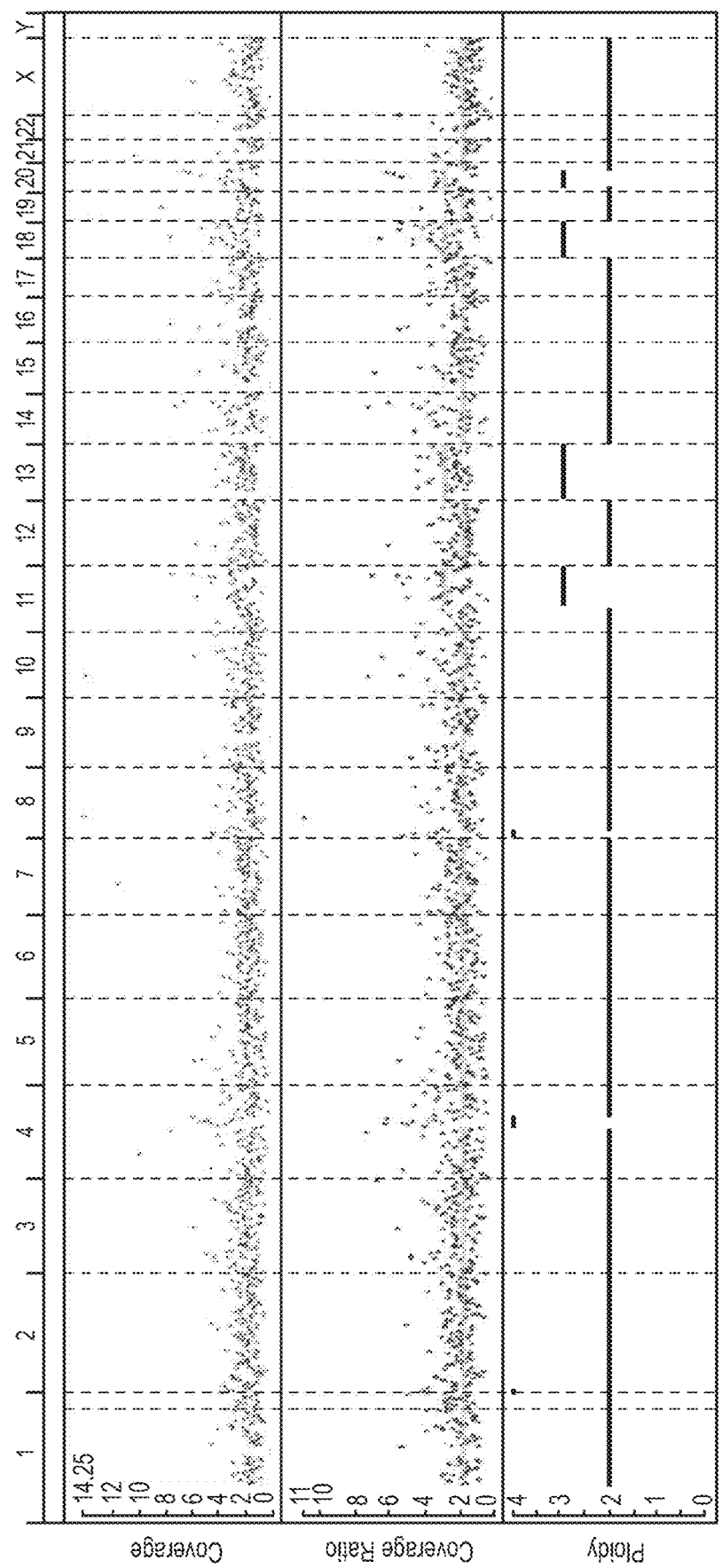

FIG. 30: Whole genome karyogram of a fNRBC isolated from peripheral blood of a woman pregnant with a female fetus having trisomy 13 and trisomy 18.

5. DETAILED DESCRIPTION

5.1. Definitions

An antibody is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also any antigen binding fragment thereof (i.e., "antigen-binding portion") or single chain thereof, fusion proteins comprising an antibody, and any other modified configuration of the immunoglobulin molecule that comprises an antigen recognition site, including, for example without limitation, single chain (scFv) and domain antibodies (e.g., human, camelid, or shark domain antibodies), maxibodies, minibodies, intrabodies, diabodies, triabodies, tetrabodies, vNAR and bis-scFv (see e.g., Hollinger and Hudson, 2005, Nature Biotech 23:1126-1136). An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, and $IgA_2$. "Antibody" also encompasses any of each of the foregoing antibody/immunoglobulin types that has been modified to facilitate sorting and detection, for example as described in Section 5.3.5.

Antigen binding portion of an antibody, as used herein, refers to one or more fragments of an intact antibody that retain the ability to specifically bind to a given antigen (e.g., target X). Antigen binding functions of an antibody can be performed by fragments of an intact antibody. Examples of binding fragments encompassed within the term "antigen binding portion"

Biological sample is a sample in which fNRBCs are present or suspected to be present. In a particular embodiment, the biological sample is maternal blood or a fraction thereof enriched for fNRBCs (e.g., a fraction from which maternal non-nucleated red blood cells have been depleted). The maternal blood is typically drawn at 4 weeks, 5 weeks, 6 weeks, 8 weeks, 10 weeks, 12 weeks, 16 weeks, 20 weeks, 24 weeks, 30 weeks or 38 weeks of gestation, or one or more times during a time period ranging between any two of the foregoing embodiments, e.g., 4-38 weeks, 4-10 weeks, 4-16 weeks, 4-24 weeks, 5-16 weeks, 5-24 weeks, 5-38 weeks, 6-12 weeks, 6-16 weeks, 6-30 weeks, 6-20 weeks, 8-38 weeks, and so on and so forth. The optimal period of gestation for drawing maternal blood for fNRBC enrichment is about 6 weeks to about 20 weeks of gestation. During this period, both primitive and definitive fetal red blood cells are present in the maternal circulation, thereby maximizing the quantities of fNRBCs enriched by the methods of the disclosure. The maternal blood can be from a single or multiple pregnancy (e.g., twins, triplets, quadruplets) and can include fNRBCs of a single gender (male or female) or both genders. Other types of biological samples are plasma, cells from a chorionic villus sampling (CVS) biopsy or cells from a percutaneous umbilical cord blood sampling, or a fraction thereof. As used herein, a "biological sample" can include reagents used in the enrichment or isolation of fNRBCs, such as buffers, antibodies and nuclear stains.

Compete, as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present disclosure.

Negative selection refers to depletion of cells other than a target cell of interest from mixed cell population. Negative selection can be based on a marker that is absent from (or undetectable in or on) the target cell. Negative selection can also be based on other criteria, e.g., size, morphology, or other physical characteristics.

Negative immunoselection refers to depletion of cells utilizing an antibody, e.g., an antibody that selectively binds to one or more cell types other than the target cells of interest but does not specifically bind to the target cells.

A negative immunoselective antibody is an antibody that can be used in negative immunoselection, e.g., is an antibody that binds to a marker that is present on or in one or more cell types other than the target cells but is absent from the target cell. The antibody can bind to a marker on the cell surface or an internal marker, but the marker is preferably a surface marker to avoid the need for fixation.

Positive selection refers to selection of cells (e.g., for enrichment and/or isolation purposes) containing a target cell of interest from a mixed cell population. Positive selection can be based on a marker that is present on or in the target cell. In some embodiments, the marker absent from (or undetectable in or on) one or more cell types (other than the target cell) in the population (e.g., biological sample) from which the target cell is to be isolated or enriched (for example, maternal blood or a fraction of maternal blood when the target cell is an fNRBC). In further embodiments, the marker absent from (or undetectable in or on) any cell type other than the target cell of interest in the population from which the target cell is to be isolated or enriched. Positive selection can also be based on other criteria, e.g., size, morphology, or other physical characteristics.

Positive immunoselection refers to selection of cells utilizing an antibody, e.g., an antibody that binds to a marker that is present on or in the target cell of interest and which is therefore useful for positive selection.

A positive immunoselective antibody is an antibody that can be used in positive immunoselection, e.g., is an antibody that binds to a marker that is present on or in the target cell. In some embodiments, the antibody selectively binds to the target cell but does not specifically bind to one or more other cell types that may be present in a population of cells in which the target cell is present. The antibody can bind to a marker on the cell surface or an internal marker, but the marker is preferably a surface marker to avoid the need for fixation.

Selective binding with respect to a particular cell refers to the specific or preferential binding of an antibody to a marker present in or on at least one cell type in a mixed cell population (e.g., a biological sample) but absent from (or undetectable in or on) at least one other cell type in the population. By way of example, if in a mixed cell population containing cell types A, B, C, D, and E, an antibody only specifically binds to cell type A or cell types A and E, the antibody is said to selectively bind to cell types A or cell types A and E, respectively.

An antibody specifically binds or preferentially binds to a target if it binds with greater affinity, avidity, more readily, and/or with greater duration than it binds to other substances. For example, an antibody that specifically or preferentially binds to a marker present on fNRBCs is an antibody that binds this marker with greater affinity, avidity, more readily, and/or with greater duration than it binds to other markers. Specific binding or preferential binding does not necessarily require (although it can include) exclusive binding. Generally, but not necessarily, reference to "binding" means preferential binding.

5.2. Pre-Enrichment

To improve enrichment for fNRBCs, a pre-enrichment step prior to the positive and optional selection steps described below can be performed. Exemplary pre-enrichment processes are described below.

Density separation is a technique that allows the separation of cells depending on their size, shape and density. A density gradient is created in a centrifuge tube by layering solutions of varying densities with the dense end at the bottom of the tube. Cells are usually separated on a shallow gradient of sucrose or other inert carbohydrates even at relatively low centrifugation speeds.

Discontinuous density gradient centrifugation is commonly used to isolate peripheral blood mononuclear cells from granulocytes and erythrocytes. For example in a so called Ficoll density separation whole blood is layered over FICOLL-PAQUE® and then centrifuged. The erythrocytes, granulocytes and a portion of the mononuclear cells settle to the cell pellet while the remaining mononuclear cells settle to the Ficoll plasma interface. Exemplary density separation processes utilizing Ficoll are described in Section 7.1.

Alternatively, adult red blood cells can be aggregated for depletion from a biological sample, permitting enrichment of a mononuclear cell fraction containing fNRBCs. If anticoagulated blood is allowed to settle in a tube, erythrocytes sediment ahead of white blood cells, and a leukocyte-rich plasma layer may be removed after 1.5 hours or more. The erythrocytes sediment more rapidly than leukocytes because of the spontaneous tendency of erythrocytes to agglomerate. It is possible to accelerate the sedimentation of erythrocytes by adding an aggregation reagent. Exemplary aggregation reagents are nonionic polymers such as polysaccharides and synthetic polymers. In some embodiments, the polymers are dextrans of molecular weights 60,000-500,000, polyvinylpyrrolidone of molecular weigh 360,000, and polyoxyethylene (POE) of molecular weight 20,000. The aggregation reagents can be added to a biological sample containing buffer.

5.3. fNRBC Enrichment

The methods of the disclosure entail one or more positive selection processes for enrichment and/or isolation of fNRBCs and typically entail at least one positive immunoselection step using antibodies that bind to fNRBCs. Positive immunoselection can be used in conjunction with negative selection (e.g., negative immunoselection) to deplete one or more cell types other than fNRBCs, e.g., maternal lymphocytes, from the biological sample.

To practice positive immunoselection, a positive immunoselective antibody is added to a biological sample. The amount of antibody necessary to bind NRBCs can be empirically determined by performing a test separation and analysis. The cells and antibody are incubated for a period of time sufficient for complexes to form, usually at least about 5 minutes, more usually at least about 10 minutes, and usually not more than one hour, more usually not more than about 30 minutes.

The biological sample may additionally be incubated with additional positive selection and/or negative selection reagents as described herein, simultaneously or serially.

The cells are separated in accordance with the specific antibody preparation. Fluorochrome-labeled antibodies are useful for FACS separation, magnetic particles for immunomagnetic selection, particularly high gradient magnetic selection (HGMS), etc. Exemplary magnetic separation devices are described in WO 90/07380, PCT/US96/00953, and EP 438,520.

The selection and/or negative selection can be performed using other automated methods, such as ultrafiltration or microfluidic separation.

5.3.1. Positive Selection

A positive selection reagent of the disclosure can be any reagent that can be used to distinguish fNRBCs in a biological sample from at least one other type of cell in the sample.

A preferred approach for fNRBC enrichment is the use of positive immunoselection methods carried out in a fluid medium. Typically, the positive immunoselection methods utilize a positive immunoselective antibody. In certain aspects, a plurality of positive immunoselective antibodies are used in a positive immunoselection procedure.

Accordingly, in some aspects, the present disclosure provides a method for preparing fNRBCs, comprising subjecting a biological sample comprising fNRBCs to positive immunoselection, said positive immunoselection comprising the steps of: (a) contacting the biological sample with a positive immunoselective antibody in a fluid medium, wherein the positive immunoselective antibody selectively binds to fNRBCs relative to one or more other cell types in the biological sample; and (b) selecting cells bound to said positive immunoselective antibody.

5.3.2. Positive Selection Markers and Antibodies

Positive selection markers for fNRBCs include glycophorin A (also known as CD235a), "i" antigen, CD36, CD71, and nuclear markers. Where the downstream analysis permits cell fixation (e.g., FISH), fetal hemoglobin can be a positive selection marker.

Cells expressing the markers glycophorin A, "i" antigen, CD36, CD71 and fetal hemoglobin can be selected (e.g., sorted or enriched for) using antibodies against the markers.

In contrast to maternal erythrocytes, fNRBCs are nucleated and can be selected using nuclear dyes, such as Hoechst 33342, LDS751, TO-PRO, DC-Ruby, and DAPI.

In some embodiments, fNRBCs are selected for using the monoclonal antibody 4B9. The hybridoma producing the antibody 4B9 is deposited at the Deutsche Sammlung von Mikroorganismen and Zelkulturen GmbH under accession number DSM ACC 2666 fNRBCs (see U.S. Pat. Nos. 7,858,757 B2 and 8,563,312 B2 of Hollmann et al.). In other embodiments, fNRBCs are selected for using an antibody that competes with 4B9 for binding to the surface of fNRBCs. By way of example, monoclonal antibody 4B8 competes with 4B9 for binding to fNRBCs (see U.S. Pat. Nos. 7,858,757 B2 and 8,563,312 B2 of Hollmann et al.).

Further antibodies that bind to fNRBCs can be generated using the methods described in Hollmann et al. The ability to compete with 4B9 for binding to fNRBCs be tested using a competition assay. In one example of a competition assay, 4B9 antibody is used to isolate its target antigen (e.g., from fetal liver cells) and the target antigen is adhered onto a solid surface, e.g., a microwell plate. A mixture of sub-saturating amount of biotinylated and unlabeled 4B9 or candidate competing antibody (the "test" antibody) in serial dilution in ELISA buffer is added to wells and plates are incubated for 1 hour with gentle shaking. The plate is washed, HRP-conjugated Streptavidin diluted in ELISA buffer is added to each well and the plates incubated for 1 hour. Plates are washed and bound antibodies are detected by addition of substrate (e.g., TMB, Biofx Laboratories Inc., Owings Mills, Md.). The reaction is terminated by addition of stop buffer (e.g., Bio FX Stop Reagents, Biofx Laboratories Inc., Owings Mills, Md.) and the absorbance is measured at 650 nm using microplate reader (e.g., VERSAmax, Molecular Devices, Sunnyvale, Calif.). Alternatively, instead of isolating the antigen, whole fNRBCs can be used. In one approach, 1 microgram/ml of 4B9 conjugated to a first fluorescent dye (e.g., FITC) is added to microtiter wells containing $1 \times 10^5$ fetal liver cells. The test antibody conjugated to a second fluorescent dye (e.g., phycoerythrin) is titrated at concentration from 10 microgram/ml to going down to 0.001 micrograms/ml (five 1 to 2 serial dilutions). Mean fluorescent intensities are measured for both antibodies. A test antibody is said to compete with 4B9 if the MFI of the reference antibody is reduced by at least 50% when the test antibody is added at same concentration as the reference antibody or at a lower concentration. In some embodiments, the MFI is reduced by at least 60%, at least 70% or at least 80%. Other formats for competition assays are known in the art and can be employed.

5.3.3. Negative Selection

Typically, the negative selection methods of the disclosure utilize one or more reagents that do not recognize fNRBCs. In certain aspects, the reagent is a negative immunoselective antibody.

Accordingly, the negative immunoselection can comprise the steps of: (a) contacting a biological sample with a negative immunoselective antibody in a fluid medium, wherein the negative immunoselective antibody selectively binds other cells in the biological sample relative to fNRBCs; and (b) selecting cells not bound to said negative immunoselective antibody. The negative selection, if carried out, can be performed before, after, or concurrently with the positive immunoselection.

5.3.4. Negative Selection Markers and Antibodies

The negative selection reagent can be any reagent that can be used to separate cells other than fNRBCs in a biological sample from fNRBCs.

The reagent is preferably an antibody that binds an antigen present on the cell surface of maternal cells, i.e. mature cells, but not present on the cell surface of fNRBCs. In another embodiment, the negative immunoselective antibody comprises an anti-CD45 antibody. One or more negative immunoselective antibodies can be used, preferably against one or more haematopoietic cell surface markers. Exemplary cell surface markers include: (a) a T-lymphocyte cell surface marker such as CD3, CD4 or CD8; (b) a B-lymphocyte cell surface marker such as CD19, CD20, or CD32; (c) a pan lymphocyte marker such as CD45; (d) an NK cell surface marker such as CD56; (e) a dendritic cell surface marker such as CD11c or CD23; and (f) a macrophage or monocyte cell surface marker such as CD14 or CD33. In particular embodiments, at least two, three, four, or five negative immunoselective antibodies are used.

5.3.5. Antibody Labeling

Conveniently, the antibodies and nuclear stains used in the positive and negative selection processes of the disclosure can be modified to permit selection and separation of the fNRBCs from other cells types. The modified antibodies can comprise any molecule or substance that allows sorting and detection, e.g., a magnetic bead or fluorochrome. In particular embodiments, the antibodies are couple to a colorimetric molecule, a fluorescent moiety, a chemiluminescent moiety, an antigen, an enzyme, a detectable bead (such as a magnetic or electrodense (e.g., gold) bead), or a molecule that binds to another molecule (e.g., biotin or streptavidin)).

Fluorochromes can be used with a fluorescence activated cell sorter. Multi-color analyses can be employed with the FACS or in a combination of immunomagnetic separation and flow cytometry. Multi-color analysis is of interest for the separation of cells based on multiple surface antigens. Fluorochromes which find use in a multi-color analysis include phycobiliproteins, e.g., phycoerythrin and allophycocyanins; fluorescein and Texas red. A negative designation indicates that the level of staining is at or below the brightness of an isotype matched negative control. A dim designation indicates that the level of staining may be near the level of a negative stain, but may also be brighter than an isotype matched control. A positive immunoselective antibody of the disclosure preferably gives rise to a "bright" designation with respect to fNRBCs and a "negative" or "dim" designation with respect to one or more other cell types that can be present in a biological sample in which the fNRBCs are present, such as maternal blood. A negative immunoselective antibody of the disclosure preferably gives rise to a "negative" or "dim" designation with respect to fNRBCs and a "bright" designation with respect to one or more other cell types that can be present in a biological sample in which the fNRBCs are present, such as maternal blood.

In one embodiment, an immunoselective antibody is directly or indirectly conjugated to a magnetic reagent, such as a superparamagnetic microparticle (microparticle). Direct conjugation to a magnetic particle is achieved by use of various chemical linking groups, as known in the art. The antibody can be coupled to the microparticles through side chain amino or sulfhydryl groups and heterofunctional cross-linking reagents. A large number of heterofunctional compounds are available for linking to entities. A preferred linking group is 3-(2-pyridyidithio)propionic acid N-hydroxysuccinimide ester (SPDP) or 4-(N-maleimidomethyl)-cyclohexane-1-carboxylic acid N-hydroxysuccinimide ester (SMCC) with a reactive sulfhydryl group on the antibody and a reactive amino group on the magnetic particle.

Alternatively, an immunoselective antibody is indirectly coupled to the magnetic particles. The antibody is directly conjugated to a hapten, and hapten-specific, second stage antibodies are conjugated to the particles. Suitable haptens include digoxin, digoxigenin, FITC, dinitrophenyl, nitrophenyl, avidin, biotin, etc. Methods for conjugation of the hapten to a protein are known in the art, and kits for such conjugations are commercially available.

Fluorescent labels may include rhodamine, lanthanide phosphors, fluorescein and its derivatives, fluorochrome, GFP (GFP for "Green Fluorescent Protein"), dansyl, umbelliferone, phycoerythrin, phycocyanin, allophycocyanin, o-phthaldehyde, and fluorescamine.

Enzymatic labels may include horseradish peroxidase, β galactosidase, luciferase, alkaline phosphatase, glucose-6-phosphate dehydrogenase ("G6PDH"), alpha-D-galactosidase, glucose oxidase, glucose amylase, carbonic anhydrase, acetylcholinesterase, lysozyme, malate dehydrogenase and peroxidase.

Chemiluminescent labels or chemiluminescers, such as isoluminol, luminol and the dioxetanes.

Other detectable moieties include molecules such as biotin, digoxygenin or 5-bromodeoxyuridine.

In some embodiments, an immunoselective antibody is not directly modified for selection or detection but used as a primary antibody. A secondary antibody that is modified, e.g., by attachment to a magnetic bead or a fluorescent dye, can be used to select for or detect cells bound to the primary antibody.

5.3.6. Selection Techniques

The immunoselection step can utilize magnetic separation, e.g., using antibody-coated magnetic beads, or flow cytometry. Flow cytometric techniques can provide accurate separation via the use of, e.g., fluorescence activated cell sorters, which can have varying degrees of sophistication, such as multiple color channels, low angle and obtuse light scattering detecting channels, impedance channels, etc.

In various aspects, both magnetic separation (e.g., MACS) and flow cytometry (e.g., FACS) are used to enrich for fNRBCs. Each of MACS and FACS can be used for negative selection, positive selection, or both. In some embodiments, positive and/or negative selection with MACS is utilized prior to negative selection and/or positive selection with FACS. Accordingly, the present disclosure provides methods for enriching for fNRBCs comprising any combination of (A) negative selection with MACS, (B) positive selection with MACS, (C) negative selection with FACS; and (D) positive selection with FACS. Exemplary combinations of embodiments are (1) A then B then D; (2) A then D; (3) A then B then C+D simultaneously; (4) A then C+D simultaneously; (5) B then D; and (6) B then C+D simultaneously. Each of the foregoing selection step can utilize one, two, three or more reagents, e.g., antibodies and, in the case of positive selection, nuclear stains.

Conveniently, the antibodies are conjugated with labels, e.g., magnetic beads and fluorochromes, to allow for ease of separation of the fNRBCs from other cells types. Fluorochromes can be used with a fluorescence activated cell sorter. Multi-color analyses can be employed with the FACS or in a combination of immunomagnetic separation and flow cytometry. Multi-color analysis is of interest for the separation of cells based on multiple surface antigens. Fluorochromes which find use in a multi-color analysis include phycobiliproteins, e.g., phycoerythrin and allophycocyanins; fluorescein and Texas red. A negative designation indicates that the level of staining is at or below the brightness of an isotype matched negative control. A dim designation indicates that the level of staining may be near the level of a negative stain, but may also be brighter than an isotype matched control. A positive immunoselective antibody of the disclosure preferably gives rise to a "bright" designation with respect to fNRBCs and a "negative" or "dim" designation with respect to one or more (and in some embodiments all) other cell types that can be present in a biological sample in which the fNRBCs are present, such as maternal blood. A negative immunoselective antibody of the disclosure preferably gives rise to a "negative" or "dim" designation with respect to fNRBCs and a "bright" designation with respect to one or more other cell types that can be present in a biological sample in which the fNRBCs are present, such as maternal blood.

In one embodiment, an immunoselective antibody is directly or indirectly conjugated to a magnetic reagent, such as a superparamagnetic microparticle (microparticle). Direct conjugation to a magnetic particle is achieved by use of various chemical linking groups, as known in the art. The antibody can be coupled to the microparticles through side chain amino or sulfhydryl groups and heterofunctional cross-linking reagents. A large number of heterofunctional compounds are available for linking to entities. A preferred linking group is 3-(2-pyridyidithio)propionic acid N-hydroxysuccinimide ester (SPDP) or 4-(N-maleimidomethyl)-cyclohexane-1-carboxylic acid N-hydroxysuccinimide ester (SMCC) with a reactive sulfhydryl group on the antibody and a reactive amino group on the magnetic particle.

Alternatively, an immunoselective antibody is indirectly coupled to the magnetic particles. The antibody is directly conjugated to a hapten, and hapten-specific, second stage antibodies are conjugated to the particles. Suitable haptens include digoxin, digoxigenin, FITC, dinitrophenyl, nitrophenyl, avidin, biotin, etc. Methods for conjugation of the hapten to a protein are known in the art, and kits for such conjugations are commercially available.

To practice the positive immunoselection method, a positive immunoselective antibody is added to a biological sample. The amount of antibody necessary to bind NRBCs can be empirically determined by performing a test separation and analysis. The cells and antibody are incubated for a period of time sufficient for complexes to form, usually at least about 5 minutes, more usually at least about 10 minutes, and usually not more than one hour, more usually not more than about 30 minutes.

The biological sample may additionally be incubated with additional positive and/or negative immunoselective antibodies as described herein. The labeled cells are separated in accordance with the specific antibody preparation. Fluorochrome-labeled antibodies are useful for FACS separation, magnetic particles for immunomagnetic selection, particularly high gradient magnetic selection (HGMS), etc. Exemplary magnetic separation devices are described in WO 90/07380, PCT/US96/00953, and EP 438,520.

The positive immunoselection and/or negative immunoselection can be performed using other automated methods, such as ultrafiltration or microfluidic separation.

The methods of the disclosure are preferably performed with one or more positive immunoselection steps in a fluid phase and one or more positive immunoselective antibodies in soluble format, i.e., not immobilized on a solid surface. The methods of the disclosure can be adapted to incorporate one or more steps in which a positive and/or immunoselective antibody is bound to a solid surface. Immobilizing 4B9 on a solid surface for cell capture is, for example, described in U.S. application Ser. No. 13/295,532, filed Nov. 14, 2011 and published as US 2013/0122492 on May 16, 2013, the contents of which are incorporated by reference in their entireties herein.

5.4. Downstream Isolation Techniques

Following positive selection (and the optional negative selection), fNRBCs can be isolated by capture on a solid surface (e.g., with a positive immunoselective antibody such as 4B9 or a secondary antibody to capture positive immunoselective antibody-bound cells) or a physical technique such as micromanipulation.

A detectable moiety attached to the positive immunoselective antibody can be used to identify and isolate the fetal NRBCs. Micromanipulation may be performed under a microscope or through other visual enhancement or assistance. Micromanipulation may be performed through an automated process or by using manual micromanipulation equipment. For instance, micromanipulation may select or isolate a single fNRBC or multiple fNRBCs. For example, groups of 1, 5, 10 or 20 cells may be isolated by micromanipulation and placed in individual sample tubes of 1, 5, 10 or 20 cells. In some embodiments, one, two, three, four or five groups of 1-20 cells, e.g., 1-5 cells, 1-10 cells, 5-20 cells, or 5-10 cells are isolated by micromanipulation.

In some embodiments, the additional isolation techniques (e.g., micromanipulation) can take advantage of the fluorescent labels utilized to enrich the cells, the presence of hemoglobin in the fNRBCs (detectable by a Soret band filter) and fNRBC morphological features (Huang et al., 2011, J Cell Biochem. 112:1475-85; Choolani et al., 2003, Mol Hum Repro 9:227-35).

5.5. Populations of fNRBCs

The present disclosure further provides preparations of fNRBCs prepared or obtainable by the methods described herein. Exemplary preparations include populations of cells comprising fNRBCs.

In some embodiments, the populations of cells are obtained or obtainable from maternal blood, e.g., maternal blood drawn between about 4 and about 38 weeks of pregnancy or between about 6 weeks and about 20 weeks of pregnancy, by any of the work flows described in Section 6. In some embodiments, the workflows entail density gradient separation and flow cytometry (e.g., FACS), with or without an intervening MACS step for positive and/or negative enrichment.

In certain aspects, the populations comprise approximately 10, 25, 50, 100, 200, 300, 500, or 1,000 cells or FACS "events", or a population comprising a number of cells or FACS "events" ranging between any pair of the foregoing values, e.g., approximately 25-200, approximately 50-500, approximately 10-300, approximately 50-1, 000 cells or FACS "events", and so on and so forth. Preferably, at least 1%, at least 2%, at least 3%, at least 4%, at least 5%, at least 10%, at least 15% or at least 20% of the cells are fNRBCs, or at least 1%, at least 2%, at least 3%, at least 4%, at least 5%, at least 10%, at least 15% or at least 20% of the FACS "events" correspond to fNRBCs. In some embodiments, the percentage of fNRBCs or FACS "events" corresponding to fNRBCs in the population ranges between any two of the foregoing values, e.g., 2%-20%, 5%-10%, 5%-20%, 3%-15%, and so on and so forth.

The fNRBCs can be primitive fNRBCs, definitive fNRBCs, or a mixture of both. In some embodiments, the ratio of primitive and definitive fNRBCs is a ratio found in maternal blood about 6 weeks to about 20 weeks of gestation. The fNRBCs can be bound to antibody, e.g., one or more of the positive immunoselective antibodies described herein, or free of antibody. Such antibody-free fNRBCs can be prepared, for example, by stripping a positive immunoselective antibody from the cells.

When the fNRBCs are prepared from a maternal blood sample, the remaining cells in the population are typically one or more cell types present in maternal blood during gestation. The maternal cells can be bound to antibody, e.g., one or more of the negative immunoselective antibodies described herein or even bound to one or more of the positive immunoselective antibodies, or free of antibody. Such antibody-free maternal cells can be prepared, for example, by stripping any bound antibody from the cells.

5.6. Validation of fNRBCs

Genetic fingerprinting methods that involve, for example, generating a genetic profile using Short Tandem Repeat (STR) analysis, Restriction Fragment Length Polymorphism (RFLP) analysis or Single Nucleotide Polymorphism (SNP) analysis can be used to validate an fNRBC or fNRBCs isolated by the methods described herein as a fetal cell(s). By comparing the profile generated from the isolated cell(s) to a profile generated from maternal and optionally, paternal cells, the identity of the isolated cell(s) as a fetal cell(s) can be verified. Suitable kits for generating genetic profiles are commercially available. For example, the PowerPlex® Fusion STR kit from Promega and the Genome-Wide Human SNP Array 6.0 from Affymetrix can be used to generate STR and SNP profiles, respectively, which can be used to validate the identity of fNRBCs. In some embodiments, whole genome amplification (WGA) is used to increase the amount of genetic material available for analysis.

5.7. Downstream Analysis

The preparations can be used in fetal diagnostic testing, e.g., for determining the presence of a multiple pregnancy or a fetal abnormality. Examples of abnormalities that can be tested for include trisomy 13, trisomy 18, trisomy 21, Down syndrome, neuropathy with liability to pressure palsies, neurofibromatosis, Alagille syndrome, achondroplasia, Huntington's disease, alpha-mannosidosis, beta-mannosidosis, metachromatic leucodystrophy, von Recklinghausen's disease, tuberous sclerosis complex, myotonic dystrophy, cystic fibrosis, sickle cell disease, Tay-Sachs disease, beta-thalassemia, mucopolysaccharidoses, phenylketonuria, citrullinuria, galactosemia, galactokinase and galactose 4-epimerase deficiency, adenine phosphoribosyl, transferase deficiency, methylmalonic acidurias, proprionic acidemia, Farber's disease, fucosidosis, gangliosidoses, gaucher's disease, I cell disease, mucolipidosis Ill, Niemann-Pick disease, sialidosis, Wolman's disease, Zellweger syndrome, cystinosis, factor X deficiency, ataxia telangiectasia, Bloom's syndrome, Robert's syndrome, xeroderma pigmentosum, fragile (X) syndrome, sex chromosome aneuploidy, Klinefelter's Syndrome, Turner's syndrome, XXX syndrome, steroid sulfatase deficiency, microphthalmia with linear skin defects, Pelizaeus-Merzbacher disease, testis-determining factor on Y, ornithine carbamoyl transferase deficiency, glucose 6-phosphate dehydrogenase deficiency, Lesch-Nyhan syndrome, Anderson-Fabry disease, hemophilia A, hemophilia B, Duchenne type muscular dystrophy, Becker type muscular dystrophy, dup(17)(p11.2p11.2) syndrome, 16p11.2 deletion, 16p11.2 duplication, Mitochondrial defect, dup(22)(q11.2q11.2) syndrome, Cat eye syndrome, Cri-du-chat syndrome, Wolf-Hirschhorn syndrome, Williams-Beuren syndrome, Charcot-Marie-Tooth disease, chromosome rearrangements, chromosome deletions, Smith-Magenis syndrome, Velocardiofacial syndrome, DiGeorge syndrome, 1p36 deletion, Prader-Willi syndrome, Azospermia (factor a), Azospermia (factor b), Azospermia (factor c), spina bifida, anencephaly, neural tube defect, microcephaly, hydrocephaly, renal agenesis, Kallmann syndrome, Adrenal hypoplasia, Angelman syndrome, cystic kidney, cystic hygroma, fetal hydrops, exomphalos and gastroschisis, diaphragmatic hernia, duodenal atresia, skeletal dysplasia, cleft lip, cleft palate, argininosuccinicaciduria, Krabbe's disease, homocystinuria, maple syrup urine disease, 3-methylcrotonyl coenzyme A, carboxylase deficiency, Glycogenoses, adrenal hyperplasia, hypophosphatasia, placental steroid sulphatase deficiency, severe combined immunodeficiency syndrome, T-cell immunodeficiency, Ehlers-Danlos syndrome, osteogenesis imperfect, adult polycystic kidney disease, Fanconi's anemia, epidermolysis bullosa syndromes, hypohidrotic ectodermal dysplasia, congenital nephrosis (Finnish type) and multiple endocrine neoplasia.

The diagnostic assay can be a nucleic acid (e.g., DNA or RNA) assay, a protein (e.g., antibody-based) assay, or a histology assay, or a combination thereof. Examples of DNA assays include FISH, PCR and DNA sequencing assays. Examples of RNA assays include RT-PCR assay and FISH assays. To facilitate access to the nucleic acid, the fNRBCs can be lysed or permeabilized prior to carrying out the diagnostic test. The DNA, RNA and protein assays can be performed on a microarray. Illustrative methods are described below.

In some embodiments, single cells or groups of two to four or more cells can be amplified by whole genome amplification (WGA) to provide sufficient nucleic acid for analysis. Groups of cells containing 5 or more fetal NRBCs can be analyzed without the use of whole genome amplification (WGA). WGA refers to amplification of the entire genome of a cell or group of cells of an individual. For example, a whole genome can be amplified using the genetic material of a single cell (i.e., single cell whole genome amplification (SCWGA)).

Chromosomal abnormalities, single gene abnormalities, allelic variants and single nucleotide polymorphisms (SNPs) are detectable using the chromosomes or nucleic acid from lysed fetal NRBCs produced by the methods of the present disclosure by any of a variety of methods, including fluorescence in situ hybridization (FISH), polymerase chain reaction (PCR), multiple annealing and looping based amplification cycles (MALBAC), restriction fragment length polymorphism (RFLP) analysis and DNA sequencing. The PCR technique can be a simple PCR amplification technique or a quantitative PCR, a real-time PCR or a reverse transcriptase PCR technique. Other useful genetic analysis techniques include array comparative genomic hybridization (CGH) and analysis in a DNA microarray. For instance, the fetal NRBCs can be analyzed in a prenatal chromosomal microarray.

A haplotype is a combination of alleles that occur together and at adjacent locations on a chromosome. A haplotype may be found on a single locus or on several loci. Haplotypes may occur throughout an entire chromosome. Haplotypes may include any number of recombination events. A haplotype may also refer to a set of associated single nucleotide polymorphisms.

A single nucleotide polymorphism (SNP) occurs where there is a variation from a normal (e.g., wild type) nucleotide sequence in a single nucleotide (e.g., A, T, C or G). For example, a single nucleotide polymorphism may result in an allelic variant. A given allele may be defined by a single nucleotide polymorphism or by multiple nucleotide changes.

Restriction Fragment Length Polymorphisms (RFLPs) are differences in homologous sequences of DNA. They may be detected by differences in fragment lengths found after digestion of DNA using a particular restriction endonuclease or combination of restriction endonucleases. RFLP may be determined by gel electrophoresis or southern blots.

Fluorescence in situ hybridization (FISH) is performed by binding fluorescent probes to a portion of a fixed nucleic acid sequence complement to that of the fluorescent probe. FISH can be used to fluorescently tag a target nucleic acid sequence in RNA or DNA at the specific position where a nucleic acid sequence occurs within a larger nucleic acid sequence. For example, FISH may be used to tag a target sequence on a chromosome. The fluorescent probe may be viewed using fluorescence microscopy.

PCR is used to amplify one or more copies (i.e., amplicons) of a particular nucleic acid sequence by using two primers. PCR methods are readily available and are commonly used to diagnose hereditary diseases.

Quantitative PCR (qPCR) is based on a polymerase chain reaction (PCR) and is used to both amplify and simultaneously quantify the total number of copies or the relative number of copies of a nucleic acid sequence. One example of qPCR is Real-Time PCR. In Real-Time PCR, the number or relative number of nucleic acid copies resulting from PCR are detected in real time. The number or relative number of copies produced by qPCR may be detected and quantified using a signal generated by fluorescent dyes.

Reverse Transcription Polymerase Chain Reaction (RT-PCR) is a method which can be used to detect RNA molecules or to determine the expression levels of a specific RNA sequence (e.g., mRNA) by transcribing the RNA molecule(s) into DNA copies (cDNA) and amplifying the DNA. RT-PCR may be performed by a one-step or two-step process.

Array Comparative Genomic Hybridization (array CGH) is a microarray technique used to determine chromosome copy number variations that occur on a genome-wide scale. Array CGH compares a test genome with a normal (e.g., wild type) genome to detect even relatively small (e.g., 200 base pairs) structural variations. For example, array CGH may detect deletions, amplifications, breakpoints or aneuploidy. Array CGH may also be used to detect a predisposition for developing a cancer.

Multiple Annealing and Looping Based Amplification Cycles (MALBAC) is a whole genome amplification method. MALBAC can be used for single cell, whole genome amplification. MALBAC can be used to amplify a genome in a quasi-linear fashion and avoid preferential amplification of certain DNA sequences. In MALBAC, amplicons may have complementary ends, which form loops in the amplicon and therefore prevent exponential copying of the amplicon. Amplicon loops may prevent amplification bias. MALBAC can be applied to diagnosing fetal abnormalities using a single fNRBC, or may be used to identify a fetal predisposition for developing a cancer using a single fNRBC.

Next Generation Sequencing (NGS) is a group of high-throughput sequencing technologies that can be used for detecting a fetal abnormality. NGS (e.g., massively parallel sequencing) uses a cell sample as small as a single cell to sequence large stretches of nucleic acid sequences or an entire genome. For example, in NGS many relatively small nucleic acid sequences may be simultaneously sequenced from a genomic DNA (gDNA) sample from a library of small segments (i.e., reads). The reads can then be reassembled to identify a large nucleic acid sequence or a complete nucleic acid sequence of a chromosome. For instance, in NGS, as many as 500,000 sequencing operations may be run in parallel. NGS is a form of single cell, whole genome amplification (WGA). For instance, MALBAC may be used for NGS when followed by traditional PCR.

Massively Parallel Signature Sequencing (MPSS) is one example of an NGS. MPSS identifies mRNA transcripts from 17-20 base pair signature primer sequences. MPSS can be utilized to both identify and quantify mRNA transcripts in a sample (Brenner et al., 2000, Nature biotechnology 18(6): 630-634, 2000).

Polony Sequencing is another example of NGS. Polony sequencing can be used to read millions of immobilized DNA sequences in parallel. Polony sequencing is a multiplex sequencing technique that has been found to be extremely accurate (low error rate) (Shendure et al., 2004. Nature Reviews Genetics 5(5): 335-344, 2004; Shendure et al., 2008, Nature Biotech 26(10): 1135-1145).

454 Pyrosequencing is another example of NGS. 454 pyrosequencing utilizes luciferase to detect individual nucleotides added to a nascent DNA. 454 pyrosequencing amplifies DNA contained in droplets of water in an oil solution. Each droplet of water contains one DNA template attached to a primer-coated bead (Vera et al., 2008, Molecular Ecology 17(7): 1636-1647).

Illumine Sequencing is another example of NGS. In Illumine Sequencing DNA molecules and primers are attached to a slide. The DNA molecules are amplified by a polymerase and DNA colonies (DNA clusters) are formed (Shendure et al., 2008, Nature Biotech 26(10): 1135-1145; Meyer et al., 2010, Cold Spr Hbr Protocols 2010(6): pdb-prot 5448).

Sequencing by Oligonucleotide Ligation and Detection (SOLID Sequencing) is another example of NGS. SOLID sequencing is a method of sequencing by ligation. SOLID sequencing randomly generates thousands of small sequence reads simultaneously and immobilizes the DNA fragments on a solid support for sequencing (Shendure et al., 2008, Nature Biotech 26(10): 1135-1145; Meyer et al., 2009, New Biotechnology 25(4):195-203).

Ion Torrent Semiconductor Sequencing is another example of NGS. Ion Torrent Semiconductor Sequencing is a sequencing-by-synthesis method that detects hydrogen ions released during DNA polymerization. A deoxyribonucleotide triphosphate is introduced into a microwell containing a template DNA strand to be sequenced. When the dNTP is complementary to a leading template nucleotide, the dNTP is incorporated into the complementary DNA strand and a hydrogen ion is released (Quail et al., 2012, BMC Genomics 13(1): 341).

DNA Nanoball Sequencing is another example of NGS. DNA Nanoball Sequencing can be used to determine an entire genomic sequence of an organism, such as, for instance, a newly discovered organism. Small fragments of genomic DNA are amplified using rolling circle replication to form DNA nanoballs. DNA sequences can then be ligated by using fluorescent probes as guides (Ansorge et al., 2009, New Biotechnology 25(4): 195-203; Drmanac et al., 2010, Science 327(5961):78-81).

Heliscope Single Molecule Sequencing is another example of NGS. Heliscope Single Molecule Sequencing is a direct-sequencing approach that does not require ligation or PCR amplification. DNA is sheared, tailed with a poly-A tail and then hybridized to the surface of a flow cell with oligo(dT). Billions of molecules may be then sequenced in parallel (Pushkarev et al., 2009, Nature Biotechnology 27(9): 847-850).

Single Molecule Real Time (SMRT) Sequencing is another example of NGS. SMRT sequencing is a sequencing-by-synthesis approach. DNA is synthesized in small well-like containers called zero-mode wave-guides (ZMWs). Unmodified polymerases attached to the bottom of the ZMWs are used to sequence the DNA along with fluorescently labeled nucleotides which flow freely in the solution. Fluorescent labels are detached from the nucleotides as the nucleotide is incorporated into the DNA strand (Flusberg et al., 2010, Nature methods 7(6): 461-465).

Ultra-Deep Sequencing refers to the number of times that a nucleic acid sequence is determined from many template copies. Ultra-Deep Sequencing may be used to identify rare genetic mutations by amplifying a relatively small target nucleic acid sequence which may contain a rare mutation.

DNA Microarray can be used to measure the expression levels of multiple genes simultaneously. DNA Microarray can also be used to genotype multiple regions of a genome. For example, Prenatal Chromosomal Microarray (CMA)—can be used to detect copy-number variations, such as aneuploidies in a chromosome. Prenatal CMA may detect deletions or duplications of all or part of a chromosome.

In certain aspects, a single fNRBC or a small group of fNRBCs can be subject to DNA fingerprinting, for example on a SNP microarray using the principles described by Treff et al., 2010, Fertility and Sterility 94(2):477-484, which is incorporated by reference herein in its entirety. The SNP microarrays to be used in these methods are preferably genome-wide SNP arrays. In various embodiments, the SNP fingerprint comprises at least 50,000, at least 100,000, at least 150,000, at least 200,000 or at least 250,000 SNPs. The SNP fingerprint can be generated from a single microarray or multiple microarrays. Using comparative DNA fingerprinting, a fNRBC can be distinguished from a maternal cell. In preferred embodiment, the determination of a match with the maternal cell (e.g., that the cell under examination is a maternal, rather than fetal, cell) is based on at least 1,000, more preferably at least 1,500 and yet more preferably at least 2,000 informative SNPs. The maternal fingerprint can be based on a historical maternal sample or a maternal sample run in parallel with the fNRBC. The DNA fingerprinting can be preceded by WGA of the fNRBC and optionally the maternal sample. The SNP fingerprint can also be used to fetal abnormalities or other characteristics. Microarrays can be adapted to include a combination of SNPs and markers of fetal characteristics and/or possible fetal cell abnormalities, such as those described above. In particular embodiments, the microarrays include at least 5, at least 10, at least 15, at least 20, at least 30 or at least 50 markers of possible fetal cell abnormalities and/or markers of fetal sex, such as Y chromosome markers.

5.8. KITS

The present disclosure further provides kits comprising one or more antibodies useful in the positive immunoselection methods of the disclosure, such the antibodies described in Section 5.3.2 above. In some embodiments, the kits comprise the antibody 4B9. The antibodies can be attached to a detectable moiety, e.g., biotin or a fluorescent moiety. If the antibodies are biotinylated, the kit can also include an avidin-conjugated detection reagent (i.e., antibody).

The kits can also include one or more negative immunoselective antibodies, such as antibodies against the targets described in Section 5.3.4 above. The negative immunoselective antibodies are preferably attached to a detectable moiety that is distinguishable from a detectable moiety attached to the positive immunoselective antibody.

The kits can also include a nuclear stain for better selection of fNRBCs.

Buffers and the like useful for using the antibodies for enrichment of fNRBCs are well-known in the art and may be prepared by the end-user or provided as a component of the kit. The kit may also include a solid support containing positive- and negative-control tissue samples, e.g., fetal liver cells as positive controls and/or adult blood or cellular components of adult blood as negative controls.

The kits can also include one or more reagents suitable for fetal cell diagnostics, such as reagents suitable for carrying out the diagnostic methods described in Section 5.7 above. In an exemplary embodiment, the reagents include primers, e.g., for PCR or sequencing, and/or optionally probes, e.g., for detection of fetal cell abnormalities.

6. EXEMPLARY WORKFLOWS

FIG. 1 and FIG. 2 illustrate some exemplary workflows for fNRBC enrichment and/or isolation. The methods of the disclosure can entail one entire workflow depicted in FIG. 1 or FIG. 2 or a combination of steps from the workflow that is suitable for enriching for or isolating fNRBCs.

Referring to FIG. 1, an exemplary work flow begins with a pre-enrichment step (3) followed by enrichment (4). The pre-enrichment can be performed in accordance with the methods of Section 5.2 or Section 7.1. The enrichment can entail positive and/or negative selection using magnetic cell sorting, for example as described in Sections 5.3, 7.2 and 7.3. The resulting populations of cells can be (i) directly sorted (4b) and analyzed (7), (ii) micromanipulated to isolated individual fNRBCs or pools of fNRBCs (4a) and analyzed (7), (iii) fluorescently stained (5), subject to flow cytometry (6), directly sorted (6b) and analyzed (7), or (iv) subject to flow cytometry (6), micromanipulated to isolate individual fNRBCs or pools of fNRBCs (6a) and analyzed (7). Micromanipulation can be performed as described in Section 7.6. The analysis can entail testing validating the fNRBCs as fetal (e.g., as described in Section 5.6) and/or downstream analysis, for instance testing for multiple pregnancies or fetal abnormalities (e.g., as described in Section 5.7). The fNRBC genome can be subject to whole genome amplification prior for validation and/or downstream analysis. The same nucleic acid sample (directly extracted from the cell or following amplification such as whole genome amplification) can be used for both validation and downstream analysis. The pre-enrichment (3) and enrichment (4) can make use of any of exemplary protocol combinations #1-#18 as set forth in Section 7. For workflows that entail flow cytometry, the enriched (e.g., magnetically sorted) cell population can be fluorescently stained, for example as described in Section 7, prior to flow cytometry. The staining can utilize directly labeled immunoselective antibodies and/or nuclear dyes (e.g., as described in Section 5.3.5), or secondary antibodies that are labeled. In some embodiments, a secondary antibody is used to label a primary antibody used in magnetic sorting. In some embodiments, the primary antibody is 4B9. In some embodiments, flow cytometry utilizes at least two or at least three reagents for the selection of fNRBCs, e.g., any two or all three of: 4B9 antibody, anti-CD235a antibody, and a nuclear stain. If positive selection is used, the monoclonal antibody 4B9 can be used as a positive selection reagent. If negative selection is used, an anti-CD45 antibody can be used as a negative selection reagent.

Also referring to FIG. 1, another exemplary work flow begins with a pre-enrichment step (3) followed by fluorescent staining (5) and flow cytometry (6). The flow cytometry can be followed by direct sorting (6b) and analysis (7), or micromanipulation to isolate individual fNRBCs or pools of fNRBCs (6a) and analysis (7). Micromanipulation can be performed as described in Section 7.6. The analysis can entail testing validating the fNRBCs as fetal (e.g., as described in Section 5.6) and/or downstream analysis, for instance testing for multiple pregnancies or fetal abnormalities (e.g., as described in Section 5.7). The fNRBC genome can be subject to whole genome amplification prior for validation and/or downstream analysis. The same nucleic acid sample (directly extracted from the cell or following amplification such as whole genome amplification) can be used for both validation and downstream analysis. Prior to flow cytometry, the pre-enriched cell population can be fluorescently stained, for example as described in Section. The staining can utilize directly labeled immunoselective antibodies and/or nuclear dyes (e.g., as described in Section 5.3.5), or secondary antibodies that are labeled. In some embodiments, flow cytometry utilizes at least two or at least three reagents for the selection of fNRBCs, e.g., any two or all three of: 4B9 antibody, anti-CD235a antibody, and a nuclear stain.

Referring to FIG. 2, an exemplary work flow begins with a Ficoll separation step, for example as described in Section 7.1, followed by magnetic cell sorting (negative and/or positive), for example as described in Sections 5.3, 7.2 and 7.3, followed by (A) FISH, (B) micromanipulation to isolate individual fNRBCs or pools of fNRBCs, or (C) FACS to sort for fNRBCs. FACS can be followed by micromanipulation. Micromanipulation (B) can be performed as described in Section 7.6. Following micromanipulation, the selected fNRBCs can be validated as fetal (e.g., as described in Section 5.6) and/or subject downstream analysis, for instance testing for multiple pregnancies or fetal abnormalities (e.g., as described in Section 5.7). The fNRBC genome can be subject to whole genome amplification prior for validation and/or downstream analysis. The same nucleic acid sample (directly extracted from the cell or following amplification such as whole genome amplification) can be used for both validation and downstream analysis. The Ficoll separation and magnetic cell sorting steps can utilize any of exemplary protocol combinations #1-#18 as set forth in Section 7. For workflows that entail FACS sorting, the magnetically sorted cell population can be fluorescently stained, for example as described in Section 7, prior to the FACS. The staining can utilize directly labeled immunoselective antibodies and/or nuclear dyes (e.g., as described in Section 5.3.5), or secondary antibodies that are labeled. In certain aspects, a secondary antibody is used to label a primary antibody used in magnetic sorting for FACS analysis. In some embodiments, the primary antibody is 4B9. In some embodiments, FACS sorting utilizes at least two or at least three reagents for the selection of fNRBCs, e.g., any two or all three of: 4B9 antibody, anti-CD235a antibody, and a nuclear stain. If magnetic sorting is used for positive selection, the monoclonal antibody 4B9 can be used as a positive selection reagent. If magnetic sorting is used for negative selection, an anti-CD45 antibody can be used as a negative selection reagent.

In the foregoing workflows, the conditions of a separation or sorting step (e.g., a Ficoll separation step, a magnetic cell sorting step, or a FACS sorting step) are preferably selected to achieve at least a 10-fold enrichment of fNRBCs. In some particular embodiments:

(a) a Ficoll separation step can enrich fNRBCs in a cell preparation by two, three or four orders of magnitude, or by a magnitude ranging between any two of the foregoing values, e.g., by 3-4 orders of magnitude, by 2-4 orders of magnitude, or by 2-3 orders of magnitude; and/or (b) a magnetic cell sorting step can enrich fNRBCs by two, three or four orders of magnitude, or by a magnitude ranging between any two of the foregoing values, e.g., by 3-4 orders of magnitude, by 2-4 orders of magnitude, or by 2-3 orders of magnitude; and/or (c) a FACS sorting step can enrich fNRBCs by one, two or three orders of magnitude, or by a magnitude ranging between any two of the foregoing values, e.g., by 1-3 orders of magnitude, by 1-2 orders of magnitude, or by 2-3 orders of magnitude.

In one particular combination of embodiments of the foregoing workflows, a Ficoll separation step can enrich fNRBCs in a cell preparation by approximately three orders of magnitude (e.g., reducing a fNRBC-containing population from billions to millions of cells), a magnetic cell sorting step can enrich fNRBCs by approximately another three orders of magnitude (e.g., reducing a fNRBC-containing population from millions to the thousands of cells), and a FACS sorting step can enrich fNRBCs by approximately an another order of magnitude (e.g., reducing a fNRBC-containing population from thousands to hundreds of cells).

Optionally, following any of the foregoing embodiments or combinations of embodiments for enrichment of fNRBCs, individual fNRBCs are selected (e.g., via micromanipulation) for analysis.

In some embodiments of each of the foregoing workflows that entails analysis of fNRBCs, the fNRBC genome is analyzed for chromosome copy number. Chromosome copy number can be analyzed by FISH or by quantitation of DNA amplified from the cell, e.g., by whole genome amplification or quantitative PCR.

7. EXEMPLARY PROTOCOLS

Various combinations of the density separation protocols of Section 7.1, the negative selection protocols of Section 7.2, and/or positive selection protocols of Section 7.3 are used to enrich NRBCs from a sample comprising fNRBCs and maternal cells, e.g., maternal blood. For example, the following combinations of the protocols are within the scope of the disclosure. Following enrichment, the enriched NRBCs can be subject to fluorescent staining, for example as described in Section 7.4, for further analysis. Prior to analysis, the NRBCs can be further enriched by FACS, for example utilizing the work flows illustrated in FIG. 1 and FIG. 2.

Combination #1: density separation protocol #1 and positive selection protocol #1
Combination #2: density separation protocol #1 and positive selection protocol #2.
Combination #3: density separation protocol #2 and positive selection protocol #1
Combination #4: density separation protocol #2 and positive selection protocol #2.
Combination #5: density separation protocol #3 and positive selection protocol #1
Combination #6: density separation protocol #3 and positive selection protocol #2.
Combination #7: density separation protocol #1, negative selection protocol #1, and positive selection protocol #1.
Combination #8: density separation protocol #1, negative selection protocol #1, and positive selection protocol #2.
Combination #9: density separation protocol #2, negative selection protocol #1, and positive selection protocol #1.
Combination #10: density separation protocol #2, negative selection protocol #1, and positive selection protocol #2.
Combination #11: density separation protocol #3, negative selection protocol #1, and positive selection protocol #1.
Combination #12: density separation protocol #3, negative selection protocol #1, and positive selection protocol #2.
Combination #13: density separation protocol #1 and positive selection protocol #3.
Combination #14: density separation protocol #2 and positive selection protocol #3.
Combination #15: density separation protocol #3 and positive selection protocol #3.
Combination #16: density separation protocol #1, negative selection protocol #1, and positive selection protocol #3.
Combination #17: density separation protocol #2, negative selection protocol #1, and positive selection protocol #3.
Combination #18: density separation protocol #3, negative selection protocol #1, and positive selection protocol #3.

7.1. Density Separation

7.1.1. Density Separation Protocol #1

The following exemplary density separation protocol #1 is suitable for use in the methods of the disclosure:

1. Add an amount of density separation media to a centrifuge tube having a porous barrier positioned within the tube, e.g., a Leucosep® tube. Centrifuge the tube to fill the tube below the porous barrier with media, e.g., at 230×g for 1 minute. The amount of medium added to the tube should be an amount sufficient to fill the section of the tube below the porous barrier after centrifugation. After centrifugation, discard any medium, if any, remaining above the porous barrier. While a centrifuge tube lacking a porous barrier can be used for density separation in the methods of the disclosure, the use of a centrifuge tube having a porous barrier prevents the mixing of sample with the media, maintaining a discontinuous gradient and improving separation.
2. Add an amount of blood to the centrifuge tube. Treating the blood, e.g., diluting the blood with a buffer such as phosphate buffered saline containing 2 mM EDTA, pH 7.2, can help improve separation. Thus, the blood added to the centrifuge tube can be treated, for example diluted with buffer.
3. Centrifuge the tube to form a plasma layer and an enriched cell fraction above the porous barrier, e.g., by centrifuging the tube at 1000×g for 20 minutes.
4. Transfer everything above the porous barrier (plasma, PBMCs, etc.) to a second centrifuge tube.
5. Add a wash buffer, e.g., PBS+2 mM EDTA, pH 7.2, to the second centrifuge tube and mix. Then, centrifuge the second centrifuge tube to pellet the cells, e.g., at 450×g for 10 minutes.
6. Aspirate the supernatant completely without disturbing the pellet.
7. Resuspend the pellet with a wash buffer.
8. Centrifuge the resuspended pellet to again pellet the cells.
9. Aspirate the supernatant completely without disturbing the pellet.

Washing steps 5-9 remove the density separation media and plasma from the enriched cells and can improve the yield of subsequent processing steps.

7.1.2. Density Separation Protocol #2

Density separation protocol #1 modified by adding rinsing step 2.1 following step 2 provides density separation protocol #2:
  2.1 Add a wash buffer to the container that contained the blood added to the centrifuge tube in step 2, then add the wash buffer to the centrifuge tube.

This rinsing step 2.1 can increase yield of fNRBCs.

7.1.3. Density Separation Protocol #3

Density separation protocol #2 modified by replacing step 4 with the following step 4 provides density separation protocol #3:
  4. Remove the plasma layer from the centrifuge tube and discard. Transfer the remaining liquid above the porous barrier to a second centrifuge tube.

Removing the plasma layer prior to washing steps 5-9 can provide a more pure population of enriched cells.

7.2. Negative Selection

In some embodiments of the present disclosure, a sample comprising fNRBCs and maternal cells is subject to negative selection to deplete the sample of maternal cells. In some embodiments, the negative selection employs magnetic activated cell sorting (MACS) with microbeads coupled to anti-CD45 antibody.

7.2.1. Negative Selection Protocol #1

The following exemplary negative selection protocol #1 is suitable for use in the methods of the disclosure:
  1. Resuspend the final pellet from any one of density separation protocols #1-3 with a MACS running buffer, e.g., autoMACS® Running Buffer (Miltenyi Biotec).
  2. Centrifuge the sample to pellet the cells, e.g., at 450×g for 10 minutes.
  3. Aspirate the supernatant completely.
  4. Resuspend the cell pellet in a MACS running buffer.
  5. Add CD45 microbeads microbeads attached to anti-CD45 antibody) to the sample, mix and incubate to allow the CD45 microbeads to bind to maternal cells.
  6. Add a MACS running buffer to the sample and mix. Then, centrifuge the sample to pellet the cells, e.g., at 450×g for 10 minutes. Aspirate the supernatant completely.
  7. Resuspend the pellet in a MACS running buffer.
  8. Magnetically sort the cells using a MACS column according to manufacturer instructions to obtain a CD45 negative fraction and a CD45 positive cell fraction.

Steps 1-3 remove residual wash buffer from the cells. Washing step 6 removes unbound CD45 microbeads from the sample.

7.3. Positive Selection

In some embodiments of the present disclosure, a sample comprising fNRBCs and maternal cells is subject to positive selection using the antibody 4B9.

7.3.1. Positive Selection Protocol #1

The following exemplary positive selection protocol #1 is suitable for use in the methods of the disclosure:
  1. If starting with a suspension comprising fNRBCs obtained by negative selection protocol #1, centrifuge the suspension to pellet cells, e.g., at 450×g for 10 minutes, and aspirate the supernatant completely. If starting with a cell pellet from any of density separation protocol #1-3, begin at step 2.
  2. Resuspend the pellet in a MACS running buffer.
  3. Add an FcR blocking reagent, e.g., FcR Blocking Reagent (Miltenyi Biotec), and mix well. The FcR blocking reagent blocks non-specific Fc receptor-mediated antibody binding.
  4. Add biotinylated 4B9; incubate to allow the biotinylated 4B9 to bind to fNRBCs.
  5. Add MACS running buffer to the sample; centrifuge to pellet the cells, e.g., at 300×g for 10 minutes.
  6. Aspirate the supernatant completely.
  7. Add MACS running buffer to the sample and centrifuge the sample to pellet the cells, e.g., at 450×g for 10 minutes.
  8. Aspirate the supernatant completely.
  9. Resuspend the pellet in a MACS running buffer.
  10. Add an FcR blocking reagent to the sample to block non-specific Fc receptor-mediated antibody binding in step 11.
  11. Add anti-biotin microbeads to the sample; incubate to allow microbeads to bind to biotinylated-4B9.
  12. Add MACS running buffer to the sample and mix. Then, centrifuge the sample to pellet the cells, e.g., at 450×g for 10 minutes. Aspirate the supernatant completely.
  13. Add MACS running buffer to the sample.
  14. Magnetically sort the cells using a MACS column according to manufacturer instructions to obtain a 4B9 positive fraction and a 4B9 negative fraction.

Steps 5-8 remove unbound biotinylated-4B9 from the sample. Washing step 12 removes unbound anti-biotin microbeads from the sample.

7.3.2. Positive Selection Protocol #2

Positive selection protocol #1 modified by replacing biotinylated-4B9 with unconjugated 4B9 and replacing anti-biotin microbeads with anti-IgM microbeads provides positive selection protocol #2.

7.3.3. Positive Selection Protocol #3

4B9$^+$ cells are selected by incubating with unconjugated 4B9 (IgM monoclonal antibody), washing to remove unbound 4B9 antibody, binding the 4B9 coated cells with goat-anti-mouse-IgM microbeads, and then washing, resuspending and centrifuging the resulting cells. Following centrifugation, the supernatant is discarded and the pellet resuspended in a buffer such as PBS.

7.4. Staining

In some embodiments of the present disclosure, a sample comprising fNRBCs prepared according to the disclosure is fluorescently stained to allow for visualization, sorting, e.g., by FACS, and/or picking of isolated fNRBCs.

7.4.1. Staining Protocol #1

The following exemplary staining protocol #1 can be used to fluorescently stain a sample comprising fNRBCs:
1. Centrifuge the 4B9 positive fraction prepared according to any one of combinations #1-18, above, to pellet the cells, e.g., at 400×g for 10 minutes.
2. Aspirate the supernatant.
3. Add a fluorescent master mix to the sample and incubate, where the master mix contains a suitable labeled marker for detecting fNRBCs enriched according to any of the protocols described above, e.g., streptavidin Alexa 488 and/or goat anti-mouse IgM Alexa 488, and a nuclear marker, e.g., Hoechst.
4. Add a buffer to the sample, e.g., 1×PBS with 0.5% BSA, to wash the cells.
5. Centrifuge the sample to pellet the cells, e.g., at 400×g for 10 minutes.
6. Aspirate the supernatant.
7. Resuspend the pellet in an appropriate buffer, e.g., 1×PBS.

7.4.2. Staining Protocol #2

The following exemplary staining protocol #2 can also be used to fluorescently stain a sample comprising fNRBCs:
1. Centrifuge the 4B9 positive fraction prepared according to any one of combinations #1-18, above, to pellet the cells, e.g., at 400×g for 10 minutes.
2. Resuspend the pellet in a buffer, e.g., 1×PBS.
3. Add an FcR blocking reagent to block non-specific Fc receptor-mediated antibody binding in step 4.
4. Add unconjugated 4B9 to the sample; incubate the sample to allow the 4B9 to bind to fNRBCs.
5. Add a fluorescent master mix to the sample and incubate, where the master mix contains a suitable labeled marker for detecting fNRBCs, e.g., CD235a-PE and/or goat anti-mouse IgM Alexa 488, and a nuclear marker, e.g., DC-Ruby.
6. Add a buffer to the sample, e.g., 1×PBS, to wash the cells.
7. Centrifuge the sample to pellet the cells, e.g., at 300×g for 5 minutes.
8. Aspirate the supernatant.
9. Resuspend the pellet in an appropriate buffer, e.g., 1×PBS.

Appropriate volumes and concentrations of reagents, temperatures, mixing times, centrifugation times, centrifugation forces, and specific reagents used in the above protocols can be selected by those having ordinary skill in the art. Similarly, persons having skill in the art will appreciate that washing steps can be added or omitted from the above protocols without changing the basic operation of the protocols.

7.5. Preparation for Downstream Analysis

Original biological samples containing fNRBCs or samples enriched for fNRBCs by any of the method steps described above, can be subject to further processing to enrich or isolate steps fNRBCs.

Automated cell separation techniques are suitably used. Examples of such techniques include, without limitation, fluorescence activated cell sorting (FACS), flow cytometry, ultrafiltration, microfluidics or any combination of two or more of these methods. FACS can be performed using standard procedures and instructions provided by the FACS instrument manufacturer to further enrich for or isolate fNRBCs. Exemplary FACS gating that can be used to isolate fNRBCs according to the methods described herein and the resulting datasets are shown in FIG. 3 and FIG. 7.

fNRBCs can also be isolated by manual methods such as micromanipulation. Using micromanipulation techniques known in the art or described in the Section 7.6 below, individual fNRBCs can be picked and isolated.

Following enrichment, the cells can be subject to downstream analysis, for example Short Tandem Repeat (STR) analysis of their genomic DNA, DNA fingerprinting, chromosome copy number analysis, and/or other methods for verification of fetal cell identity, diagnosis of fetal abnormality or disease, and testing of fetal characteristics.

7.6. Cell Picking by Micromanipulation

For isolation of cells a commercial micromanipulator is mounted onto an inverse phase contrast microscope. The microscope is equipped with various objectives, fluorescent filters, a camera, monitor, and joystick operated micromanipulator platform. Micromanipulation is composed in three linear axes—X, Y, and Z directions.

Cells obtained from the positively selected fraction and fluorescently stained with various antibodies are placed onto a pre-cleaned microscope slide and isolated with a sterile capillary tube with a diameter of the opening on the capillary tip configured to the size of the fNRBCs. The fluorescent stains can correspond to one or more antibodies that recognize fetal cells, selected from 4B9 (Zimmermann et al., 2013, Exp Cell Res 319:2700-2707), anti-CD34, anti-CD71, anti-glycophorin-A, and anti-i-antigen (Huang et al., 2011, J Cell Biochem. 112:1475-85; Choolani et al., 2003, Mol Hum Repro 9:227-35; Calabrese et al., 2012, Clin Genet. 82(2): 131-9). If the cells are fixed, e.g., in order to perform FISH, anti-epsilon globin, reportedly a highly specific primitive fetal erythroblast identifier (Choolani et al., 2003, Mol Hum Repro 9:227-35; Choolani et al., 2001, Blood 98:554-7), can be used.

Each antibody used during the fluorescent staining step(s) corresponds to its own specific fluorescent filter on the microscope and visualized either through the eye piece and/or monitor depending on the wavelengths.

In addition to fluorescent markers, selection criteria for fNRBCs can be hemoglobin content (detectable by a Soret filter) and morphological features. Primitive fNRBCs have distinguishing morphological features of having a high cytoplasmic to nuclear ratio and a comparatively larger size (Huang et al., 2011, J Cell Biochem. 112:1475-85; Choolani et al., 2003, Mol Hum Repro 9:227-35).

Cells with the desired morphology, nucleus to cell ratio, and fluorescent staining pattern(s) are manually picked with the micromanipulator and placed in 0.2ml PCR tubes for downstream analysis purposes.

The exemplary protocols described were used to obtain enriched cell populations containing fNRBCs as shown in Table 1, below.

TABLE 1

| Sample | Sample volume (mL) | Isolation Protocol[1] | Staining Protocol[2] | Number of FACS events | Number of 4B9 + FACS events | Single cells picked by micro-manipulation | Multiple cells picked by micro-manipulation[3] |
|---|---|---|---|---|---|---|---|
| 1 | 19 | DS #2, PS #2 | SP#2 | 202,370 | 60 | | |
| 2 | 18 | DS #3, PS #2 | SP#2 | 135,626 | 240 | | 2 × 5 |
| 3 | 15 | DS #3, PS #2 | SP#2 | 1,077,876 | | | 1 × 5, 1 × 6 |
| 4 | 19 | DS #3, PS #2 | SP#2 | 1,423,135 | | | |
| 5 | 12 | DS #3, PS #2 | SP#2 | 135,093 | 14 | | |
| 6 | 17 | DS #3, PS #2 | SP#2 | 336,668 | 105 | 6 | |
| 7 | 19 | DS #3, PS #2 | SP#2 | 803,085 | 130 | 7 | |
| 8 | 19 | DS #3, PS #2 | SP#2 | 102,029 | 50 | | |
| 9 | 19 | DS #3, PS #2 | SP#2 | 504,344 | 249 | | |
| 10 | 15 | DS #3, PS #2 | SP#2 | 488,828 | 100 | | |
| 11 | 21 | DS #3, PS #2 | SP#2 | 46,148 | 42 | 15 | 1 × 3 |

[1]DS is density separation protocol; NS is negative selection protocol; PS is positive selection protocol
[2]SP is staining protocol
[3]A × B means A sets of B cells were picked

8. EXAMPLE 1: FISH ANALYSIS OF fNRBCS ISOLATED FROM MATERNAL BLOOD BY DENSITY SEPARATION+MACS

Samples of maternal peripheral blood obtained from 40 women 5 to 16 weeks pregnant with a male fetus were processed according to density separation protocol #3 and positive selection protocol #2 to provide a magnetic cell separation "soup" (MCSS) containing fNRBCs. Cells were fixed to a slide and analyzed using FISH to identify X and Y chromosomes.

At least 5 cells with a Y chromosome per sample were manually counted when the slides were viewed under a microscope. 10 of the 40 samples were randomly selected in an effort to determine the average number of cells with a Y chromosome present in each sample. The whole slide was scanned under a microscope and each Y probe was manually counted. The number of fNRBCs counted in each of the 10 samples is shown in Table 2. On average, 24 fNRBCs were counted per sample.

TABLE 2

| Sample | Gestational Age (weeks) | Number of fNRBCs identified |
|---|---|---|
| 1 | 10 | 59 |
| 2 | 11 | 20 |
| 3 | 10 | 35 |
| 4 | 9 | 29 |
| 5 | 14 | 24 |
| 6 | 7 | 22 |
| 7 | 12 | 20 |
| 8 | 11 | 14 |
| 9 | 9 | 12 |
| 10 | 5 | 8 |

A photomicrograph of cells from sample 8 probed for X and Y chromosomes is shown in FIG. 4.

Other illustrative FISH images of fetal cells isolated from maternal blood using density separation and MACS are shown in FIGS. 5 and 6.

9. EXAMPLE 2: CHARACTERIZATION OF fNRBCs IN FETAL LIVER

Fresh or frozen mononuclear fetal liver cells were obtained from various donors with a range of gestational ages and stored in liquid nitrogen. Cells were processed by an outside source under an approved IRB donor program with corresponding certificate of analysis.

Fresh mononuclear male cells were obtained from various donors as negative controls.

The fetal liver mononuclear cells and the male mononuclear cell were processed using density gradient separation. In some studies, the density gradient fraction containing fNRBCs was followed by positive selection with 4B9 using MACS, and the MACS-sorted 4B9 positive fraction was sorted by FACS. In other studies, the density gradient fraction containing fNRBCs was sorted by FACS without an intervening MACS selection process. Prior to the FACS sorting, the cells were fluorescently stained using 4B9 and a goat-anti mouse IgM secondary antibody, anti-CD235a, and DC-Ruby.

The FACS sorting analyzed the number of events, % parent, and % total for the different gated regions (lymphocytes and monocytes, CD235a+, and triple positive (DC-Ruby+, 4B9+, CD235a+ cells). The number of triple positive events observed for both sample types are as follows: fetal liver cells ranged between 20-45 percent and male cells ranged between 0.02-0.10 percent of the total events sorted.

Cells were sorted and visualized on a microscope with corresponding fluorescent filters. Analysis of fetal liver and male mononuclear cells permitted the characterization of cells based on cell morphology, nucleus to cell ratio, and fluorescent staining pattern(s) and establishment of quality control measures for FACS sorted cell populations containing fNRBCs.

10. EXAMPLE 3: STR ANALYSIS OF FETAL LIVER fNRBCS ISOLATED FROM MIXED CELL POPULATION BY DENSITY SEPARATION+MACS+FACS

This example demonstrates via a spike-in experiment that the methods of the disclosure permit the enrichment of fNRBCs.

10.1. Preparation of a 4B9$^+$ Enriched Cell Population from a Mixed Cell Population Four thousand female fetal liver cells were added into 25 mL of normal male blood from an unrelated male subject prior to mononuclear cell isolation via density gradient centrifugation.

PBMCs were prepared by density gradient centrifugation protocol #2. The resulting cell population was subject to positive selection according to positive selection protocol #2.

The cells were stained with goat anti-mouse IgM Alexa Flour 488 and DC-Ruby, and then sorted by fluorescence activated cell sorting (FACS) using a Sony SH800 cell sorter.

FIG. 8A shows correlated measurements of FSC and BSC of the 4B9 negative cell fraction demonstrating the differentiation of cell types. FIG. 8B shows the cell subpopulation of the lymphocyte gate based on FSC vs. BSC from the 4B9 negative cell fraction, observing nucleated and 4B9 cell types. The 4B9 positive cell fraction is represented in FIG. 9A and FIG. 9B. FIG. 9B demonstrates nucleated, 4B9 positive cells in the top right quadrant. Non-nucleated 4B9 positive cells are located in the bottom right quadrant.

The events gated in the top square (4B9 Positive: 43.53%) in FIG. 9B were sorted into a 0.2ml PCR tube for STR analysis to identify the cell types located in this region.

10.2. Downstream Analysis of the 4B9+ Cell Fraction

STR (Short tandem Repeat) analysis of the 4B9+ fraction was performed using the Powerflex® Fusion (Promega, WI) five color kit for fluorescent detection of 23 STR loci and the sex-specific amelogenin polymorphic gene locus.

FIGS. 10-13 are electropherograms of the male genomic DNA, fetal liver genomic DNA, and 4B9 positive sorted fraction showing the peaks of the labeled loci for FAM, VIC, NED and PET.

In each channel shown in FIGS. 10-13 (FAM, VIC, NED and PET, respectively) a STR profile was generated for the male genomic DNA, fetal liver genomic DNA, and 4B9 positive fraction.

The 4B9 positive fraction (bottom panels) in FIGS. 10-13 demonstrates that after isolation, enrichment and FACS sorting, the majority of the cells isolated were of fetal origin. The profile for the 4B9 positive fraction was composed of both the male and fetal liver profiles; however, the major contributor was the fetal profile.

The profile of this mixed population of cells contained major and minor peaks resulting from two different contributors. Based on the presence of alleles and subsequent heights of those peaks the major and minor contributor was determined.

FIG. 14 represents two markers from the FAM channel from the 4B9 positive fraction. Here it was observed that marker D10S1248 contains 4 alleles (A, B, C, and D). Alleles A and C are the highest of the four peaks and are of fetal origin, whereas alleles B and D are the lowest of the four peaks and are of male origin (see, FIG. 10). Marker D13S317 contains only 3 alleles (E, F, and G). Here the male and fetal liver cells shared a common allele at F, resulting in the highest peak. The second highest peak is G, from fetal origin, and the lowest peak is E, of male origin. FIG. 14 thus demonstrates that the fetal profile was the major contributor to the profile from the 4B9 positive fraction.

Additionally, FIG. 10 contains the sex-specific loci amelogenin (AMEL), which contains a single X for female samples and an X and Y for male samples. The 4B9 fraction did not indicate a Y loci present, reiterating that the majority of the 4B9 positive fraction was fetal cells and not male cells.

This example demonstrates that when a small number of fetal liver cells are spiked into a significantly larger number of male cells, the majority of the cells recovered using the isolation and enrichment methods described herein are fetal cells.

11. EXAMPLE 5: STR ANALYSIS OF fNRBCS ISOLATED FROM MATERNAL BLOOD BY VARIOUS PROTOCOLS

11.1. STR Analysis of fNRBCs Isolated from Maternal Blood by Density Separation+MACS Samples of maternal peripheral blood obtained from 40 women 4 to 14 weeks pregnant, with either a male or female fetus, were processed according to density separation protocol #1, negative selection protocol #1, and positive selection protocol #1 to provide a MCSS for each sample. Samples were stained according to staining protocol #1. 4B9 tagged cells were then picked from each MCSS, pooled, and analyzed using the PowerPlex® Fusion (Promega, WI) STR kit for fluorescent detection of 23 STR loci and the sex-specific amelogenin polymorphic gene locus to confirm fetal identity. Fetal alleles were identified in 100% of samples.

FIGS. 15-18 show the STR analysis of a sample processed from maternal peripheral blood obtained from a female pregnant with a male fetus at 7 weeks gestational age. Cells were fluorescently stained following positive selection with goat anti-mouse IgM AF 488, Streptavidin 488, and Hoechst. Two sets of 10 pooled cells manually picked were used for STR analysis. In each of the four channels of the electropherograms shown in FIGS. 15-18, there are four STR profiles. From top to bottom, the four profiles are: isolated 4B9 positive fraction A and B (respectively), maternal genomic DNA, and paternal genomic DNA. The circles formed by alternating dashes and dots indicate alleles found in the isolated 4B9 positive fraction that are shared between the mother's and father's profiles. The circles formed by even short dashes indicate alleles found in the isolated 4B9 positive fraction that are only found in the father's profile.

11.2. STR Analysis of fNRBCs Isolated from Maternal Blood by Density Separation+MACS+FACS

11.2.1. fNRBCs Isolated by Density Separation Protocol #2, Positive Selection Protocol #2, and FACS STR analysis was performed on samples of maternal blood from pregnant females that were processed by density separation protocol #2, positive selection protocol #2 and FACS, and without negative selection. FIGS. 19-22 show STR analysis of a sample processed from maternal peripheral blood obtained from a female pregnant with a male fetus at 9 weeks gestational age. Cells were fluorescently stained following positive selection with goat anti-mouse IgM, CD235a, and DC-Ruby, FACS sorted, manually picked, and pooled together for STR analysis. A total of 8 cells were picked. From top to bottom of FIGS. 19-22, three profiles are shown: maternal genomic DNA, isolated 4B9 positive fraction, and paternal genomic DNA. The circles formed by alternating dashes and dots indicate alleles found in the isolated 4B9 positive fraction that are shared between the mother's and father's profiles. The circles formed by even short dashes indicate alleles found in the isolated 4B9 positive fraction that are only found in the father's profile.

11.2.2. fNRBCs Isolated by Density Separation Protocol #3, Positive Selection Protocol #2, and FACS STR analysis was performed on samples of maternal blood from pregnant females that were processed by density separation protocol #3, positive selection protocol #2, and FACS, and without negative selection. FIGS. 23-26 show STR analysis of a sample processed from maternal peripheral blood obtained from a female pregnant with a male fetus at 12 weeks gestational age. Cells were fluorescently stained following positive selection with goat anti-mouse IgM, CD235a, and DC-Ruby, and FACS sorted directly into 0.2m1 PCR tubes for STR analysis. A total of 35 events were sorted. Tubes A-C contained 10 events and tube D contained 5 events. From top to bottom of FIGS. 23-26, four profiles are shown: maternal genomic DNA, two separate reactions isolated from the 4B9 positive fraction (tube C and D, respectively), and paternal genomic DNA. The circles formed by alternating dashes and dots indicate alleles found in the isolated 4B9 positive fraction that are shared between the mother's and father's profiles. The circles formed by even short dashes indicate alleles found in the isolated 4B9 positive fraction that are only found in the father's profile.

12. EXAMPLE 6: FINGERPRINTING ANALYSIS OF ISOLATED NRBCS 100 samples of maternal peripheral blood were processed according to density separation protocol #3 and positive selection protocol #2 to provide a MCSS. The cells of the MCSS were stained according to staining protocol #2. 4B9 tagged cells were then isolated from other cells and debris by FACS. Cells triple positive for DC-Ruby, CD235a, and 4B9 were sorted onto a slide. Single cells were picked by micromanipulation and graded based on morphology and fluorescence.

Altogether, 235 cells were selected from the 100 maternal blood samples for WGA and fingerprinting analysis based on their single nucleotide polymorphism profiles. Maternal cells were also subject to WGA and fingerprinting analysis. The fingerprinting analysis validated 230 out of the 235 cells isolated from maternal blood (i.e., 97.3% of the cells) as fetal cells, and there was at least one confirmed fetal cell isolated from each maternal blood sample.

13. EXAMPLE 7: ANALYSIS OF fNRBCS ISOLATED FROM MATERNAL BLOOD BY ION TORRENT™ SEMICONDUCTOR SEQUENCING

Approximately 30 samples of maternal peripheral blood from females pregnant with a male fetus (identified by analyzing cell free fetal (cff) DNA present in maternal plasma by RT-PCR with SRY/DYS primers and probes) and several samples of maternal peripheral blood from females pregnant with a female fetus were processed using the exemplary density separation, positive selection, and staining protocols described in Section 7. The samples were then sorted by FACS. Single 4B9 tagged cells were then picked by micromanipulation.

To each cell was added 8 µl of distilled water followed by 1 µl of a lysis solution comprising 200 mM KOH and 50 mM dithiothreitol. Each sample was then incubated at 65° C. for 10 minutes. The samples were then cooled to 4° C., and 1 µL of a neutralization buffer comprising Tris-HCl, pH 8.3 and 300 mM KCl was then added to each sample. Each sample was then vortexed for 1 minute. Samples were then centrifuged for 1 minute and then stored at −20° C. prior to whole genome amplification.

Whole genome amplification was performed on each sample using the GenomePlex® Single Cell Whole Genome Amplification Kit (Sigma, catalog no. WGA4). WGA products were cleaned using the GenElute™ PCR Clean-Up Kit (Sigma, catalog no. NA1020) and eluted in 50 µl of 10 mM Tris, pH 8.0. The DNA concentrations of the cleaned samples were determined using a Qubit® 2.0 fluorometer (Life Technologies).

DNA libraries were then constructed for Ion Torrent™ semiconductor sequencing using DNA library preparation kits (ThermoFisher Scientific or Kapa Biosystems). The DNA concentrations of the libraries were determined using a Qubit® 2.0 fluorometer (Life Technologies). A quality control assay was run on each library using an Agilent TapeStation™ system (Agilent Technologies). Ion Torrent™ semiconductor sequencing was then performed on each library using an Ion OneTouch™ System and Ion Personal Genome Machine™ (ThermoFisher Scientific) according to the manufacturer's instructions. The sequencing data was analyzed using Ion Reporter™ software (ThermoFisher Scientific) and whole genome karyograms were generated using the Integrative Genomics Viewer (Broad Institute) by aligning the sequenced DNA segments against a reference genome. Exemplary whole genome karyograms are shown in FIG. 27-30.

Ion Torrent™ semiconductor sequencing detected an X and a Y chromosome in each of the libraries made from cells isolated from peripheral blood of females pregnant with a male fetus, thus confirming the fetal identity of each of the cells. In addition to confirming the fetal origin of the cells used to make the libraries, the Ion Torrent™ semiconductor sequencing was also able to identify trisomies when present, e.g., trisomy 13 as shown in FIG. 29. Ion Torrent™ semiconductor sequencing detected two X and no Y chromosomes in each of the libraries made from cells isolated from females pregnant with a female fetus, and in one case also detected trisomy 13 and trisomy 18 (see FIG. 30).

14. SPECIFIC EMBODIMENTS

The present disclosure is exemplified by the specific embodiments below.

1. A method for preparing fetal nucleated red blood cells (NRBCs), comprising subjecting a biological sample comprising fNRBCs to positive immunoselection, said positive immunoselection comprising the steps of:
    (a) contacting the biological sample with a first antibody in a fluid medium, wherein the first antibody selectively binds to fNRBCs relative to other cells (e.g., one or more other cell types) in the biological sample; and
    (b) selecting cells bound to said first antibody.
2. The method of embodiment 1, which further comprises subjecting the biological sample to negative immunoselection, said negative immunoselection comprising the steps of:
    (a) contacting the biological sample with a second antibody in a fluid medium, wherein the second antibody selectively binds other cells in the biological sample relative to fNRBCs; and
    (b) selecting cells not bound to said second antibody.
3. The method of embodiment 2, wherein the positive immunoselection is performed prior to the negative immunoselection.
4. The method of embodiment 2, wherein the negative immunoselection is performed prior to the positive immunoselection.
5. The method of embodiment 2, wherein the positive immunoselection and negative immunoselection are performed concurrently.

6. The method of any one of embodiments 1 to 5, wherein the first antibody binds an antigen present on the surface of fNRBC nucleated precursor cells but does not bind CD71 or other surface antigens present on adult erythroid cells.

7. The method of embodiment 6, wherein the first antibody is 4B9 or an antibody that competes with 4B9 for binding to the surface of fNRBC nucleated precursor cells.

8. The method of any one of embodiments 1 to 7, in which a plurality of first antibodies are used.

9. The method of any one of embodiments 1 to 8, wherein the positive immunoselection is performed using an automated method.

10. The method of embodiment 9, wherein the automated method is cell sorting, ultrafiltration or microfluidic separation.

11. The method of any one of embodiments 2 to 10, wherein the second antibody is against a cell surface marker selected from:
    (a) a T-lymphocyte cell surface marker, optionally CD3, CD4 or CD8;
    (b) a B-lymphocyte cell surface marker, optionally CD19, CD20 or CD32;
    (c) a pan lymphocyte marker, optionally CD45;
    (d) an NK cell surface marker, optionally CD56;
    (e) a dendritic cell surface marker, optionally CD11c or CD23; and
    (f) a macrophage or monocyte cell surface marker, optionally CD14 or CD33.

12. The method of any one of embodiments 2 to 11, in which a plurality of second antibodies are used.

13. The method of embodiment 12, wherein the plurality of second antibodies includes antibodies against at least one, two, three, four, or five of the following cell surface markers: CD3, CD4, CD8, CD19, CD20, CD45, CD56, CD11c, CD23, CD14, CD32 and CD33.

14. The method of any one of embodiments 2 to 13, wherein the negative immunoselection is performed using an automated method.

15. The method of embodiment 11, wherein the automated method is cell sorting, ultrafiltration or microfluidic separation.

16. The method of any one of embodiments 1 to 15, which further comprises enriching for fNRBCs using a density separation method.

17. The method of embodiment 16, wherein the density separation method is performed prior said positive immunoselection.

18. The method of any one of embodiments 1 to 17, which further comprises isolating fNRBCs by micromanipulation.

19. The method of embodiment 18, wherein the micromanipulation is performed after the positive immunoselection.

20. The method of any one of embodiments 1 to 19, wherein the biological fluid comprises blood, plasma, urine or a suspension of cells from a chorionic villus sampling (CVS) biopsy or a percutaneous umbilical cord blood sampling.

21. The method of embodiment 20, wherein the biological sample comprises maternal blood.

22. The method of embodiment 21, wherein the maternal blood is from a maternal blood sample taken from a pregnant subject from about 5 weeks to about 38 weeks of gestation 23. A preparation of fNRBCs prepared or obtainable by the method of any one of embodiments 1 to 22.

24. The method of any one of embodiments 1 to 22, which further comprises performing a diagnostic assay on the fNRBCs.

25. A method for diagnosing fNRBCs, comprising performing a diagnostic assay on the preparation of fNRBCs of embodiment 23.

26. The method of embodiment 24 or embodiment 25, wherein the diagnostic assay is for determining the presence of a multiple pregnancy.

27. The method of embodiment 24 or embodiment 25, wherein the diagnostic assay is for determining the presence of a fetal abnormality.

28. The method of embodiment 27, wherein the fetal abnormality is trisomy 13, trisomy 18, trisomy 21, Down syndrome, neuropathy with liability to pressure palsies, neurofibromatosis, Alagille syndrome, achondroplasia, Huntington's disease, alpha-mannosidosis, beta-mannosidosis, metachromatic leucodystrophy, von Recklinghausen's disease, tuberous sclerosis complex, myotonic dystrophy, cystic fibrosis, sickle cell disease, tay-sachs disease, beta-thalassemia, mucopolysaccharidoses, phenylketonuria, citrullinuria, galactosemia, galactokinase and galactose 4-epimerase deficiency, adenine phosphoribosyl, transferase deficiency, methylmalonic acidurias, proprionic acidemia, Farber's disease, fucosidosis, gangliosidoses, gaucher's disease, I cell disease, mucolipidosis Ill, Niemann-Pick disease, sialidosis, Wolman's disease, Zellweger syndrome, cystinosis, factor X deficiency, ataxia telangiectasia, Bloom's syndrome, Robert's syndrome, xeroderma pigmentosum, fragile (X) syndrome, sex chromosome aneuploidy, Klinefelter's Syndrome, Turner's syndrome, XXX syndrome, steroid sulfatase deficiency, microphthalmia with linear skin defects, Pelizaeus-Merzbacher disease, testis-determining factor on Y, ornithine carbamoyl transferase deficiency, glucose 6-phosphate dehydrogenase deficiency, Lesch-Nyhan syndrome, Anderson-Fabry disease, hemophilia A, hemophilia B, Duchenne type muscular dystrophy, Becker type muscular dystrophy, dup(17)(p11.2p11.2) syndrome, 16p11.2 deletion, 16p11.2 duplication, Mitochondrial defect, dup(22)(q11.2q11.2) syndrome, Cat eye syndrome, Cri-du-chat syndrome, Wolf-Hirschhorn syndrome, Williams-Beuren syndrome, Charcot-Marie-Tooth disease, chromosome rearrangements, chromosome deletions, Smith-Magenis syndrome, Velocardiofacial syndrome, DiGeorge syndrome, 1p36 deletion, Prader-Willi syndrome, Azospermia (factor a), Azospermia (factor b), Azospermia (factor c), spina bifida, anencephaly, neural tube defect, microcephaly, hydrocephaly, renal agenesis, Kallmann syndrome, Adrenal hypoplasia, Angelman syndrome, cystic kidney, cystic hygroma, fetal hydrops, exomphalos and gastroschisis, diaphragmatic hernia, duodenal atresia, skeletal dysplasia, cleft lip, cleft palate, argininosuccinicaciduria, Krabbe's disease, homocystinuria, maple syrup urine disease, 3-methylcrotonyl coenzyme A, carboxylase deficiency, Glycogenoses, adrenal hyperplasia, hypophosphatasia, placental steroid sulphatase deficiency, severe combined immunodeficiency syndrome, T-cell immunodeficiency, Ehlers-Danlos syndrome, osteogenesis imperfect, adult polycystic kidney disease, Fanconi's anemia, epidermolysis bullosa syndromes, hypohidrotic ectodermal dysplasia, congenital nephrosis (Finnish type) and multiple endocrine neoplasia.

29. The method of any one of embodiments 24 to 28, wherein the diagnostic assay is a nucleic acid assay.

30. The method of embodiment 29, wherein the nucleic acid assay is a DNA assay, optionally where the DNA assay is carried out on a microarray.

31. The method of embodiment 29 or embodiment 30, wherein the nucleic acid assay is a FISH, PCR or DNA sequencing assay.

32. The method of embodiment 29, wherein the nucleic acid assay is an RNA assay, optionally where the RNA assay is carried out on a microarray.

33. The method of embodiment 32, wherein the RNA assay is an RT-PCR assay or a FISH assay.

34. The method of any one of embodiments 29 to 33, which further comprises lysing or permeabilizing the fNRBC prior to carrying out the diagnostic test.

35. The method of any one of embodiments 24 to 28, wherein the diagnostic assay is a protein detection assay, optionally where the protein detection assay is carried out on a microarray.

36. The method of embodiment 35, wherein the protein is detected using an antibody.

37. The method of any one of embodiments 24 to 28, wherein the diagnostic assay is a histological assay.

38. A method of preparation of fetal nucleated red blood cells (NRBCs) for diagnostic testing, the method comprising:
  (a) optionally, providing a biological fluid comprising one or more fNRBCs each having a fetal cell surface, and a plurality of maternal cells each having a maternal cell surface;
  (b) enriching the one or more fNRBCs from a first portion of the plurality of maternal cells by a density separation method, thereby producing a first suspension comprising the one or more fNRBCs and a first number of remaining maternal cells;
  (c) incubating the first suspension with a first antibody bound to a first separable particle wherein the first antibody binds a first antigen present on the maternal cell surface of the maternal cells but not on the fetal cell surface of the fNRBCs under conditions wherein the first antibody binds the first antigen to produce a first particle-cell complex, and separating and removing the first particle-cell complex from the first suspension and, thereby producing a second suspension comprising the one or more fNRBCs and a second number of remaining maternal cells;
  (d) adding a second antibody to the second suspension, wherein the second antibody binds a second antigen present on the fetal cell surface of the fNRBCs, and wherein the second antigen is not present on the maternal cell surface, incubating the second suspension under conditions wherein the second antibody binds the second antigen to produce a second antibody-cell complex, and separating the second antibody-cell complex from the second suspension; and thereby producing a third suspension comprising one or more fNRBCs for diagnostic testing.

39. The method of preparation of fNRBCs according to embodiment 38, wherein the first antibody comprises an anti-CD45 antibody.

40. The method of preparation of fNRBCs according to embodiment 38, wherein the second antibody binds a surface antigen present on a cell surface of a fNRBC nucleated precursor cell but does not bind CD71 or other surface antigens present on adult erythroid cells.

41. The method of preparation of fNRBCs according to embodiment 40, wherein the second antibody is 4B9.

42. The method of preparation of fNRBCs according to embodiment 38, further comprising staining a cell component of the fNRBCs.

43. The method of preparation of fNRBCs according to embodiment 42, wherein the cell component of the fNRBCs are directly or indirectly stained.

44. The method of preparation of fNRBCs according to embodiment 38, further comprising isolating one or more fNRBCs by micromanipulation.

45. The method of preparation of fNRBCs according to embodiment 38, further comprising isolating or further enriching the fNRBCs by an automated separation technique.

46. The method of preparation of fNRBCs according to embodiment 45, wherein the automated separation is performed by a method selected from the group consisting of cell sorting, ultrafiltration and a microfluidic separation technique.

47. The method of preparation of fNRBCs according to embodiment 38, wherein the fNRBCs include one or more primitive erythroblasts.

48. The method of preparation of fNRBCs according to embodiment 38, wherein the fNRBCs include one or more definitive erythroblasts.

49. The method of preparation of fNRBCs according to embodiment 38, wherein the biological fluid comprises blood, plasma, urine or a suspension of cells from a chorionic villus sampling (CVS) biopsy or a percutaneous umbilical cord blood sampling.

50. The method of preparation of fNRBCs according to embodiment 44, wherein the biological fluid comprises maternal blood.

51. The method of preparation of fNRBCs according to embodiment 50, wherein the maternal blood is from a maternal blood sample taken from a pregnant subject at from about 5 weeks to about 38 weeks gestation.

52. The method of preparation of fNRBCs according to embodiment 38, wherein the second antibody is labeled with a detectable label.

53. The method of preparation of fNRBCs according to embodiment 52, wherein the detectable label comprises a fluorescent label, an enzyme label, a radioisotopic label, or a chemically reactive linking agent.

54. The method of preparation of fNRBCs according to embodiment 40, further comprising lysing the enriched fNRBC producing a lysed fNRBC comprising one or more nucleic acids, and analyzing the one or more nucleic acid sequences and thereby determining the presence or absence of a nucleic acid sequence indicative of a fetal abnormality or allelic variant.

55. The method of preparation of fNRBCs according to embodiment 40, further comprising determining the presence of a multiple pregnancy.

56. The method of preparation of fNRBCs according to embodiment 54, wherein analyzing the one or more nucleic acid sequences comprises detecting a chromosomal abnormality.

57. The method of preparation of fNRBCs according to embodiment 54, wherein the fetal abnormality includes a single gene abnormality.

58. The method of preparation of fNRBCs according to embodiment 54, wherein the fetal abnormality includes a single nucleotide polymorphism (SNP).

59. The method of preparation of fNRBCs according to embodiment 54, wherein analyzing the one or more nucleic acid sequences is performed by FISH, PCR or DNA sequencing.

60. The method of preparation of fNRBCs according to embodiment 59, wherein analyzing the one or more nucleic acid sequences is performed by quantitative PCR, real-time PCR or reverse transcriptase PCR.

61. The method of preparation of fNRBCs according to embodiment 54, wherein analyzing the one or more extracted nucleic acids is performed by array comparative genomic hybridization (CGH).

62. The method of preparation of fNRBCs according to embodiment 54, wherein analyzing the one or more extracted nucleic acids is performed by multiple annealing and looping based amplification cycles (MALBAC).

63. The method of preparation of fNRBCs according to embodiment 54, wherein the fetal abnormality is selected from the group consisting of trisomy 13, trisomy 18, trisomy 21, Down syndrome, neuropathy with liability to pressure palsies, neurofibromatosis, Alagille syndrome, achondroplasia, Huntington's disease, alpha-mannosidosis, beta-mannosidosis, metachromatic leucodystrophy, von Recklinghausen's disease, tuberous sclerosis complex, myotonic dystrophy, cystic fibrosis, sickle cell disease, tay-sachs disease, beta-thalassemia, mucopolysaccharidoses, phenylketonuria, citrullinuria, galactosemia, galactokinase and galactose 4-epimerase deficiency, adenine phosphoribosyl, transferase deficiency, methylmalonic acidurias, proprionic acidemia, Farber's disease, fucosidosis, gangliosidoses, gaucher's disease, I cell disease, mucolipidosis Ill, Niemann-Pick disease, sialidosis, Wolman's disease, Zellweger syndrome, cystinosis, factor X deficiency, ataxia telangiectasia, Bloom's syndrome, Roberts syndrome, xeroderma pigmentosum, fragile (X) syndrome, sex chromosome aneuploidy, Klinefelter's Syndrome, Turner's syndrome, XXX syndrome, steroid sulfatase deficiency, microphthalmia with linear skin defects, Pelizaeus-Merzbacher disease, testis-determining factor on Y, ornithine carbamoyl transferase deficiency, glucose 6-phosphate dehydrogenase deficiency, Lesch-Nyhan syndrome, Anderson-Fabry disease, hemophilia A, hemophilia B, Duchenne type muscular dystrophy, Becker type muscular dystrophy, dup(17)(p11.2p11.2) syndrome, 16p11.2 deletion, 16p11.2 duplication, Mitochondrial defect, dup(22)(q11.2q11.2) syndrome, Cat eye syndrome, Cri-du-chat syndrome, Wolf-Hirschhorn syndrome, Williams-Beuren syndrome, Charcot-Marie-Tooth disease, chromosome rearrangements, chromosome deletions, Smith-Magenis syndrome, Velocardiofacial syndrome, DiGeorge syndrome, 1p36 deletion, Prader-Willi syndrome, Azospermia (factor a), Azospermia (factor b), Azospermia (factor c), spina bifida, anencephaly, neural tube defect, microcephaly, hydrocephaly, renal agenesis, Kallmann syndrome, Adrenal hypoplasia, Angelman syndrome, cystic kidney, cystic hygroma, fetal hydrops, exomphalos and gastroschisis, diaphragmatic hernia, duodenal atresia, skeletal dysplasia, cleft lip, cleft palate, argininosuccinicaciduria, Krabbe's disease, homocystinuria, maple syrup urine disease, 3-methylcrotonyl coenzyme A, carboxylase deficiency, Glycogenoses, adrenal hyperplasia, hypophosphatasia, placental steroid sulphatase deficiency, severe combined immunodeficiency syndrome, T-cell immunodeficiency, Ehlers-Danlos syndrome, osteogenesis imperfect, adult polycystic kidney disease, Fanconi's anemia, epidermolysis bullosa syndromes, hypohidrotic ectodermal dysplasia, congenital nephrosis (Finnish type) and multiple endocrine neoplasia.

64. The method of preparation of fNRBCs according to embodiment 38, further comprising detecting a presence or absence of a protein or a metabolite in the isolated fNRBC.

65. The method of preparation of fNRBCs according to embodiment 38, further comprising detecting a level of a protein or a metabolite in the isolated fNRBC.

66. The method of preparation of fNRBCs according to embodiment 54, wherein the analyzing the one or more nucleic acids includes a Next-Generation Sequencing technique or ultra-deep sequencing.

67. The method of preparation of fNRBCs according to embodiment 54, wherein the one or more nucleic acids are analyzed in a DNA microarray.

68. The method of preparation of fNRBCs according to embodiment 54, wherein the one or more nucleic acids are analyzed in a prenatal chromosomal microarray.

69. The method of preparation of fNRBCs according to embodiment 54, wherein the fetal abnormality is detected by a restriction fragment length polymorphism (RFLP).

70. The method of preparation of fNRBCs according to embodiment 54, wherein the fetal abnormality includes a microdeletion or a microduplication.

71. The method of preparation of fNRBCs according to embodiment 54, wherein the fNRBC comprises a telomere of increased or decreased length compared with a normal range of telomere lengths.

72. The method of preparation of fNRBCs according to embodiment 54, wherein analyzing the one or more nucleic acids comprises sequencing a stretch of a nucleic acid of the fNRBC.

73. The method of preparation of fNRBCs according to embodiment 72, wherein the stretch of the nucleic acid of the fNRBC is sequenced by next-generation sequencing technology or massively parallel sequencing.

74. The method of preparation of fNRBCs according to embodiment 54, wherein the fetal abnormality is a predisposition for developing a cancer.

75. The method of preparation of fNRBCs according to embodiment 54, wherein the cancer selected from the group consisting of breast cancer, brain cancer, liver cancer, acute lymphoblastic leukemia, acute promyelocytic leukemia, adenocarcinoma, adenoma, adrenal cancer, basal cell carcinoma, bone cancer, bronchi cancer, acute or chronic lymphocytic or granulocytic tumor, acute myeloid leukemia, cervical dysplasia, chronic myelogenous leukemia, colon cancer, epidermoid carcinoma, islet cell tumor, Kaposi's sarcoma, kidney cancer, larynx cancer, leiomyoma tumor, malignant hypercalcemia, malignant melanomas, marfanoid habitus tumor, Ewing's sarcoma, gallbladder cancer, gallstone tumor, giant cell tumor, glioblastoma multiforme, hairy-cell tumor, head cancer, hyperplasia, teratoma, hyperplastic corneal nerve tumor, in situ carcinoma, intestinal ganglioneuroma, medullary carcinoma, metastatic skin carcinoma, lung cancer, lymphomas, malignant carcinoid, mucosal neuromas, mycosis fungoide, myelodysplastic syndrome, myeloma, neck cancer, neuroblastoma, osteogenic sarcoma, osteosarcoma, ovarian tumor, pancreas cancer, neural tissue cancer, thyroid cancer, topical skin lesion, parathyroid cancer, pheochromocytoma, polycythemia vera, primary brain tumor, prostate cancer, rectum cancer, renal cell tumor, retinoblastoma, rhabdomyosarcoma, seminoma, skin cancer, small-cell lung tumor, soft tissue sarcoma, squamous cell carcinoma, stomach cancer, veticulum cell sarcoma and Wilm's tumor.

76. A method of isolating a fetal nucleated red blood cell (NRBC), comprising:
    (a) optionally, providing a biological fluid comprising one or more fNRBCs each having a fetal cell surface, and a plurality of maternal cells each having a maternal cell surface;
    (b) enriching the one or more fNRBCs from a first portion of the plurality of maternal cells by a density separation method, thereby producing a first suspension comprising the one or more fNRBCs and a first number of remaining maternal cells;
    (c) incubating the first suspension with a first antibody bound to a first retrievable particle wherein the first antibody binds a first antigen present on the cell surface of maternal cells but not on the cell surface of fNRBCs under conditions wherein the first antibody binds the first antigen to produce a first particle-cell complex, and separating and removing the first particle-cell complex from the first suspension and, thereby producing a second suspension comprising the one or more fNRBCs and a second number of remaining maternal cells;
    (d) adding a second antibody bound to a second retrievable particle to the second suspension, wherein the second antibody binds a second antigen present on the cell surface of fNRBCs, and wherein the antigen is not present on the cell surface of the maternal cells, and incubating the second suspension under conditions wherein the second antibody binds the second antigen to produce a second particle-cell complex, separating the second particle-cell complex from the second suspension and releasing and resuspending the cells from the second particle-cell complex and thereby producing one or more fNRBCs; and
    (e) isolating one or more of the fNRBCs by a physical technique.

77. The method of isolating a fetal nucleated red blood cell (NRBC) according to embodiment 76, wherein the second antibody binds a surface antigen present on a cell surface of a fNRBC nucleated precursor cell but does not bind CD71 or other surface antigens present on adult erythroid cells.

78. The method of isolating a fetal nucleated red blood cell (NRBC) according to embodiment 76, wherein the second antibody is 4B9.

79. The method of isolating a fetal nucleated red blood cell (NRBC) according to embodiment 76, wherein the first antibody comprises an anti-CD45 antibody.

80. The method of isolating a fetal nucleated red blood cell (NRBC) according to embodiment 76, further comprising staining a cell component of the fNRBCs.

81. The method of isolating a fetal nucleated red blood cell (NRBC) according to embodiment 76, wherein the physical technique is micromanipulation.

82. A method of detecting a fetal abnormality, comprising:
    (a) optionally, providing a biological fluid comprising one or more fNRBCs each having a fetal cell surface, and a plurality of maternal cells each having a maternal cell surface;
    (b) enriching the one or more fNRBCs from a first portion of the plurality of maternal cells by a density separation method, thereby producing a first suspension comprising the one or more fNRBCs and a first number of remaining maternal cells;
    (c) incubating the first suspension with a first antibody bound to a first retrievable particle wherein the first antibody binds a first antigen present on the cell surface of maternal cells but not on the cell surface of fNRBCs under conditions wherein the first antibody binds the first antigen to produce a first particle-cell complex, and separating and removing the first particle-cell complex from the first suspension and, thereby producing a second suspension comprising the one or more fNRBCs and a second number of remaining maternal cells;
    (d) adding a second antibody bound to a second retrievable particle to the second suspension, wherein the second antibody binds a second antigen present on the cell surface of fNRBCs, and wherein the second antigen is not present on the cell surface of the maternal cells, and incubating the second suspension under conditions wherein the second antibody binds the second antigen to produce a second particle-cell complex, separating the second particle-cell complex from the second suspension, releasing and resuspending the cells from the second particle-cell complex, and thereby producing a third suspension comprising one or more fNRBCs; and
    (e) analyzing the one or more fNRBCs, and thereby determining a presence or absence of a fetal abnormality.

83. The method of detecting a fetal abnormality according to embodiment 82, wherein the second antibody binds a surface antigen present on a cell surface of a fNRBC nucleated precursor cell but does not bind CD71 or other surface antigens present on adult erythroid cells.

84. The method of detecting a fetal abnormality according to embodiment 82, wherein the second antibody is 4B9.

85. The method of detecting a fetal abnormality according to embodiment 82, wherein the first antibody comprises an anti-CD45 antibody.

86. The method of detecting a fetal abnormality according to embodiment 82, further comprising staining a cell component of the fNRBCs.

87. The method of detecting a fetal abnormality according to embodiment 82, wherein the fetal abnormality is selected from the group consisting of trisomy 13, trisomy 18, trisomy 21, Down syndrome, neuropathy with liability to pressure palsies, neurofibromatosis, Alagille syndrome, achondroplasia, Huntington's disease, alpha-mannosidosis, beta-mannosidosis, metachromatic leucodystrophy, von Recklinghausen's disease, tuberous sclerosis complex, myotonic dystrophy, cystic fibrosis, sickle cell disease, tay-sachs disease, beta-thalassemia, mucopolysaccharidoses, phenylketonuria, citrullinuria, galactosemia, galactokinase and galactose 4-epimerase deficiency, adenine phosphoribosyl, transferase deficiency, methylmalonic acidurias, proprionic acidemia, Farber's disease, fucosidosis, gangliosidoses, gaucher's disease, I cell disease, mucolipidosis Ill, Niemann-Pick disease, sialidosis, Wolman's disease, Zellweger syndrome, cystinosis, factor X deficiency, ataxia telangiectasia, Bloom's syndrome, Roberts syndrome, xeroderma pigmentosum, fragile (X) syndrome, sex chromosome aneuploidy, Klinefelter's Syndrome, Turner's syndrome, XXX syndrome, steroid sulfatase deficiency, microphthalmia with linear skin defects, Pelizaeus-Merzbacher disease, testis-determining factor on Y, ornithine carbamoyl transferase deficiency, glucose 6-phosphate dehydrogenase deficiency, Lesch-Nyhan syndrome, Anderson-Fabry disease, hemophilia A, hemophilia B, Duchenne type muscular dystrophy, Becker type muscular dystrophy, dup(17)(p11.2p11.2) syndrome, 16p11.2 deletion, 16p11.2 duplication, Mitochondrial defect, dup(22)(q11.2q11.2) syndrome, Cat eye syndrome, Cri-du-chat syndrome, Wolf-Hirschhorn syndrome, Williams-Beuren syndrome, Charcot-Marie-Tooth disease, chromosome rearrangements, chromosome deletions, Smith-Magenis syndrome, Velocardiofacial syndrome, DiGeorge syndrome, 1p36 deletion, Prader-Willi syndrome, Azospermia (factor a), Azospermia (factor b), Azospermia (factor c), spina bifida, anencephaly, neural tube defect, microcephaly, hydrocephaly, renal agenesis, Kallmann syndrome, Adrenal hypoplasia, Angelman syndrome, cystic kidney, cystic hygroma, fetal hydrops, exomphalos and gastroschisis, diaphragmatic hernia, duodenal atresia, skeletal dysplasia, cleft lip, cleft palate, argininosuccinicaciduria, Krabbe's disease, homocystinuria, maple syrup urine disease, 3-methylcrotonyl coenzyme A, carboxylase deficiency, Glycogenoses, adrenal hyperplasia, hypophosphatasia, placental steroid sulphatase deficiency, severe combined immunodeficiency syndrome, T-cell immunodeficiency, Ehlers-Danlos syndrome, osteogenesis imperfect, adult polycystic kidney disease, Fanconi's anemia, epidermolysis bullosa syndromes, hypohidrotic ectodermal dysplasia, congenital nephrosis (Finnish type) and multiple endocrine neoplasia.

88. A method of enriching for fetal nucleated red blood cells (fNRBCs) from a biological sample, comprising:
    (a) subjecting the biological sample to density separation to obtain a fNRBC-containing cell fraction;
    (b) subjecting the fNRBC-containing cell fraction obtained in step (a) to magnetic activated cell sorting (MACS) using at least one fNRBC positive selection reagent to obtain a MACS-sorted cell population;
    (c) fluorescently labeling cells in the MACS-sorted cell population obtained in step (b) with at least one fNRBC positive selection reagent to obtain a fluorescently labeled cell population; and
    (d) sorting the fluorescently labeled cell population obtained in step (c) by flow cytometry to select for fNRBCs, thereby obtaining a population of cells enriched for fNRBCs;
    the method of embodiment 88 optionally further comprising steps (e) and/or (f):
    (e) optionally, isolating individual fNRBCs or groups of fNRBCs by a physical method such as micromanipulation; and
    (f) optionally, validating the fetal identity of the fNRBCs, for example by genetic fingerprinting.
89. The method of embodiment 88, wherein step (b) utilizes at least one fNRBC positive selection agent and step (c) utilizes at least two fNRBC positive selection reagents, optionally wherein at least one fNRBC positive selection reagent in step (b) selects for the same target as at least one fNRBC positive selection reagent in step (c) (e.g., where both are antibodies against the same target).
90. The method of embodiment 88, wherein step (b) utilizes at least one fNRBC positive selection reagent and step (c) utilizes at least three fNRBC positive selection reagents, optionally wherein at least one fNRBC positive selection reagent in step (b) selects for the same target as at least one fNRBC positive selection reagent in step (c) (e.g., where both are antibodies against the same target).
91. The method of any one of embodiments 88 to 90, wherein at least one fNRBC positive selection reagent of step (b) comprises monoclonal antibody 4B9.
92. The method of any one of embodiments 88 to 91, wherein the at least one fNRBC positive selection reagent of step (b) comprises an anti-CD235a antibody.
93. The method of any one of embodiments 88 to 92, wherein at least one fNRBC positive selection reagent of step (c) comprises monoclonal antibody 4B9.
94. The method of any one of embodiments 88 to 93, wherein at least one fNRBC positive selection reagent of step (b) comprises an anti-CD235a antibody.
95. The method of any one of embodiments 88 to 94, wherein at least one fNRBC positive selection reagent of step (b) comprises a nuclear stain.
96. The method of any one of embodiments 88 to 95, which further comprises micromanipulation to isolate individual fNRBCs or groups of fNRBCs.
97. The method of any one of embodiments 88 to 96, which does not comprise a negative selection step.
98. The method of any one of embodiments 88 to 96, wherein the fNRBC-containing cell fraction obtained in step (a) is subject to negative selection prior to step (b).
99. The method of any one of embodiments 88 to 96, wherein the MACS-sorted cell population obtained in step (b) is subject to negative selection prior to step (c).
100. The method of embodiment 98 or embodiment 99, wherein the negative selection is negative immunoselection.
101. The method of embodiment 100, wherein the negative immunoselection utilizes one or more antibodies against one or more cell surface markers selected from:
    (a) a T-lymphocyte cell surface marker, optionally CD3, CD4 or CD8;
    (b) a B-lymphocyte cell surface marker, optionally CD19, CD20 or CD32;
    (c) a pan lymphocyte marker, optionally CD45;
    (d) an NK cell surface marker, optionally CD56;
    (e) a dendritic cell surface marker, optionally CD11c or CD23; and
    (f) a macrophage or monocyte cell surface marker, optionally CD14 or CD33.
102. A method of enriching for fNRBCs from a biological sample, comprising:
    (a) subjecting the biological sample to density separation to obtain a fNRBC-containing cell fraction;
    (b) subjecting the fNRBC-containing cell fraction obtained in step (a) to MACS using at least two fNRBC positive selection reagents to obtain a MACS-sorted cell population;
    (c) performing micromanipulation on the MACS-sorted cell population obtained in step (b) to isolate individual fNRBCs or groups of fNRBCs.
103. The method of embodiment 102, wherein at least one fNRBC positive selection reagent of step (b) comprises monoclonal antibody 4B9.
104. The method of embodiment 102 or embodiment 103, wherein at least one fNRBC positive selection reagent of step (b) comprises an anti-CD235a antibody.
105. The method of any one of embodiments 102 to 104, which does not comprise a negative selection step.

106. The method of any one of embodiments 102 to 104, wherein the fNRBC-containing cell fraction obtained in step (a) is subject to negative selection prior to step (b).
107. The method of any one of embodiments 102 to 104, wherein the MACS-sorted cell population obtained in step (b) is subject to negative selection prior to step (c).
108. The method of embodiment 106 or embodiment 107, wherein the negative selection is negative immunoselection.
109. The method of embodiment 108, wherein the negative immunoselection utilizes one or more antibodies against one or more cell surface markers selected from:
 (a) a T-lymphocyte cell surface marker, optionally CD3, CD4 or CD8;
 (b) a B-lymphocyte cell surface marker, optionally CD19, CD20 or CD32;
 (c) a pan lymphocyte marker, optionally CD45;
 (d) an NK cell surface marker, optionally CD56;
 (e) a dendritic cell surface marker, optionally CD11c or CD23; and
 (f) a macrophage or monocyte cell surface marker, optionally CD14 or CD33.
110. The method of any one of embodiments 88 to 109, wherein the biological sample is maternal blood.
111. The method of embodiment 110, wherein the maternal blood is drawn between about four weeks and about thirty eight weeks of gestation.
112. The method of embodiment 111, wherein the maternal blood is drawn between about six weeks and about twenty weeks of gestation.
113. A cell population enriched in fNRBCs obtained or obtainable by the method of any one of embodiment 88 to 112.
114. A FACS-sorted cell population containing (a) at least 2, at least 5 or at least 10 and/or (b) up to 15, up to 25, or up to 35 fNRBCs enriched from maternal blood.
115. The FACS-sorted cell population of embodiment 114, which contains (a) at least 20, at least 50 or at least 100 and/or (b) up to 150, up to 250, or up to 350 FACS events.
116. The cell population of any one of embodiments 113 to 115 which is not fixed.
117. A method of detecting a fetal abnormality, comprising analyzing at least one fNRBC from the cell population of any one of embodiments 113 to 116 for a fetal abnormality.
118. The method of embodiment 117, which further comprises enriching for fNRBCs according to the method of any one of embodiments 1 to 112 prior to said analyzing.
119. The method of embodiment 117 or embodiment 118, which comprises analyzing a single fNRBC for the fetal abnormality.
120. The method of embodiment 117 or embodiment 118, which comprises analyzing a group of fNRBCs for the fetal abnormality.
121. The method of embodiment 119 or embodiment 120 which comprises performing whole genome amplification prior to said analyzing.
122. The method of embodiment 119 or embodiment 120, which comprises amplifying a subset of the genome prior to said analyzing.
123. The method of any one of embodiments 117 to 122, wherein the analysis comprises quantitative PCR.
124. The method of any one of embodiments 117 to 122, wherein the analysis is performed on a microarray.
125. The method of any one of embodiments 117 to 124, which further comprises validating the fNRBC or fNRBCs as fetal cells.
126. The method of embodiment 125, wherein validation comprises performing short tandem repeat (STR) analysis, genetic fingerprinting or single nucleotide polymorphism (SNP) analysis.
127. The method of embodiment 125 or embodiment 126, wherein validation comprises comparing fNRBC DNA to maternal DNA.
128. The method of embodiment 125 or embodiment 126, wherein validation comprises comparing fNRBC DNA to both maternal and paternal DNA.

While various specific embodiments have been illustrated and described, it will be appreciated that various changes can be made without departing from the spirit and scope of the disclosure(s).

15. CITATION OF REFERENCES

All publications, patents, patent applications and other documents cited in this application are hereby incorporated by reference in their entireties for all purposes to the same extent as if each individual publication, patent, patent application or other document were individually indicated to be incorporated by reference for all purposes. In the event that there is an inconsistency between the teachings of one or more of the references incorporated herein and the present disclosure, the teachings of the present specification are intended.

What is claimed is:
1. A method of enriching for fetal nucleated red blood cells (fNRBCs) from a whole maternal blood sample from a woman, comprising:
 (a) subjecting a volume of 21 milliliters (mL) or less of the whole maternal blood sample comprising billions of cells per mL to pre-enrichment by performing a density gradient separation procedure to obtain a pre-enrichment sample comprising a volume with millions of cells comprising up to 100 fNRBCs;
 (b) subjecting the pre-enrichment sample obtained in step (a) to a further enrichment step comprising:
  (i) contacting the pre-enrichment sample with at least one fNRBC positive selection reagent immobilized to magnetic particles or beads, wherein the fNRBC positive selection reagent is monoclonal antibody (mAb) 4B9 or an antibody that competes with mAb 4B9 for binding to the same binding epitope or determinant on the surface of the fNRBCs bound by mAb 4B9 to obtain a magnetic activated cell sorting (MACS) sorted cell population, wherein the MACS-sorted cell population comprises thousands of cells comprising up to 100 fNRBCs, thereby further enriching the fNRBCs; or
  (ii) contacting the pre-enrichment sample with at least one fNRBC positive selection reagent conjugated to a fluorescent label, wherein the fNRBC positive selection reagent is mAb 4B9 or an antibody that competes with mAb 4B9 for binding to the same binding epitope or determinant on the surface of the fNRBCs bound by mAb 4B9 to obtain a fluorescence activated cell sorting (FACS)-sorted cell population, wherein the FACS-sorted cell population comprises thousands of cells comprising up to 100 fNRBCs, thereby further enriching the fNRBCs; and
 (c) performing micromanipulation on the MACS- or FACS-sorted cell population obtained in step (b) with at least one fNRBC positive selection reagent immobilized to a magnetic particle or bead, or conjugated to a fluorescent label, wherein said fNRBC positive selection reagent is mAb 4B9 or an antibody that competes with mAb 4B9 for binding to the same binding epitope or determinant on the surface of the fNRBCs bound by mAb 4B9, to prepare an enriched fNRBC cell population comprising at least 10% fNRBCs, wherein at least 1 fNRBC is present in the population, wherein the hybridoma producing mAb 4B9 is deposited under Deutsche Sammlung van Mikroorganismen and Zelkulturen GmbH (DSM) accession number ACC 2666.

2. The method of claim 1, wherein:
(i) step (b)(ii) further comprises contacting the pre-enrichment sample with using at least one, two, or three additional fNRBC positive selection reagents selected from the group consisting of a nuclear stain, anti-CD235a antibody, and anti-CD71 antibody to obtain the FACS-sorted cell population and/or step (c) further comprises contacting the MACS- or FACS-sorted cell population with at least one, two, or three additional fNRBC positive selection reagents selected from the group consisting of a nuclear stain, anti-CD235a antibody, and anti-CD71 antibody to prepare the enriched fNRBC cell population; and/or
(ii) prior to step (c), the method further comprises performing a negative selection step comprising contacting the MACS or FACS-sorted cell population obtained in step (b) to a monoclonal antibody against CD45.

3. The method of claim 2, wherein the negative selection is negative immunoselection, wherein optionally the negative immunoselection utilizes one or more antibodies against one or more cell surface markers selected from the group consisting of:
(a) a T-lymphocyte cell surface marker selected from the group consisting of CD3, CD4, and CD8;
(b) a B-lymphocyte cell surface marker selected from the group consisting of CD19, CD20, and CD32;
(c) an NK cell surface marker, wherein the NK cell surface marker is CD56;
(d) a dendritic cell surface marker selected from the group consisting of CD11c and CD23; and
(e) a macrophage or monocyte cell surface marker selected from the group consisting of CD14 and CD33.

4. The method of claim 1, wherein the whole maternal blood sample is drawn between about four weeks and about thirty-eight weeks of gestation.

5. The method of claim 4, wherein the whole maternal blood sample is drawn between about six weeks and about twenty weeks of gestation.

6. The method of claim 1, wherein the method further comprises validating the identity of at least one said fNRBC as a fetal cell.

7. The method of claim 1, further comprising analyzing at least one said fNRBC from the enriched fNRBC cell population for a fetal abnormality.

8. The method of claim 7, comprising performing whole genome amplification prior to said analyzing or amplifying a subset of a genome of the at least one fNRBC prior to said analyzing.

9. The method of claim 7, wherein the analysis comprises performing quantitative polymerase chain reaction (PCR) or wherein the analysis is performed using a microarray.

10. The method of claim 7, which further comprises validating the fNRBC or fNRBCs as fetal cells.

11. The method of claim 10, wherein the validating comprises performing short tandem repeat (STR) analysis, genetic fingerprinting, microarray, DNA sequencing, or single nucleotide polymorphism (SNP) analysis.

12. The method of claim 10, wherein the validating comprises comparing fNRBC DNA to maternal DNA or comparing fNRBC DNA to both maternal and paternal DNA.

13. The method of claim 1, wherein step (b) comprises performing step (b)(i) and step (b)(ii).

14. An enriched fNRBC-containing cell population obtained from whole maternal blood of a woman, wherein:
(i) fNRBCs obtained from the whole maternal blood are bound by mAb 4B9 or an antibody that competes with mAb 4B9 for binding to the same binding epitope or determinant on the surface of the fNRBCs as that bound by mAb 4B9;
(ii) the enriched fNRBC-containing cell population comprises at least 10% fNRBCs; wherein at least 1 fNRBC is present in the population,
wherein the hybridoma producing mAb 4B9 is deposited under Deutsche Sammlung van Mikroorganismen and Zelkulturen GmbH (DSM) accession number ACC 2666.

15. The cell population of claim 14 comprising approximately 20% fNRBCs, wherein, optionally, the cell population comprises approximately 50 to 1,000 cells.

16. The cell population of claim 14 which is not fixed.

* * * * *

UNITED STATES PATENT AND TRADEMARK OFFICE
CERTIFICATE OF CORRECTION

| | |
|---|---|
| PATENT NO. | : 12,203,946 B2 |
| APPLICATION NO. | : 17/902095 |
| DATED | : January 21, 2025 |
| INVENTOR(S) | : Hassan Bennani et al. |

Page 1 of 1

It is certified that error appears in the above-identified patent and that said Letters Patent is hereby corrected as shown below:

In the Claims

Column 51, Claim 2, Line 16, replace "sample with using at least one, two or three" with --sample with at least one, two or three--.

Signed and Sealed this
Eighteenth Day of November, 2025

John A. Squires
*Director of the United States Patent and Trademark Office*